(12) United States Patent
Kumano et al.

(10) Patent No.: US 10,000,622 B2
(45) Date of Patent: Jun. 19, 2018

(54) GLYCOLURILS HAVING FUNCTIONAL GROUPS AND USE THEREOF

(71) Applicant: SHIKOKU CHEMICALS CORPORATION, Kagawa (JP)

(72) Inventors: Takeshi Kumano, Kagawa (JP); Takuma Takeda, Kagawa (JP); Syozo Miura, Kagawa (JP); Takashi Kashiwabara, Kagawa (JP); Noboru Mizobe, Kagawa (JP)

(73) Assignee: SHIKOKU CHEMICALS CORPORATION, Kagawa (JP)

( * ) Notice: Subject to any disclaimer, the term of this patent is extended or adjusted under 35 U.S.C. 154(b) by 0 days. days.

(21) Appl. No.: 15/038,506

(22) PCT Filed: Nov. 25, 2014

(86) PCT No.: PCT/JP2014/081009
§ 371 (c)(1),
(2) Date: May 23, 2016

(87) PCT Pub. No.: WO2015/076399
PCT Pub. Date: May 28, 2015

(65) Prior Publication Data
US 2016/0297951 A1   Oct. 13, 2016

(30) Foreign Application Priority Data

| Nov. 25, 2013 | (JP) | 2013-242452 |
| Nov. 26, 2013 | (JP) | 2013-243804 |
| Nov. 27, 2013 | (JP) | 2013-245468 |
| Dec. 4, 2013 | (JP) | 2013-251166 |
| Dec. 6, 2013 | (JP) | 2013-252748 |
| Oct. 27, 2014 | (JP) | 2014-218061 |

(51) Int. Cl.
| C08K 5/34 | (2006.01) |
| C08K 5/3445 | (2006.01) |
| C07D 487/04 | (2006.01) |
| C08G 77/388 | (2006.01) |
| C08F 10/00 | (2006.01) |
| C08G 59/50 | (2006.01) |
| C08G 63/00 | (2006.01) |
| C08L 47/00 | (2006.01) |
| C08L 75/04 | (2006.01) |
| H01L 33/56 | (2010.01) |

(52) U.S. Cl.
CPC .......... *C08K 5/3445* (2013.01); *C07D 487/04* (2013.01); *C08F 10/00* (2013.01); *C08G 59/50* (2013.01); *C08G 63/00* (2013.01); *C08G 77/388* (2013.01); *C08L 47/00* (2013.01); *C08L 75/04* (2013.01); *H01L 33/56* (2013.01); *C08G 2190/00* (2013.01)

(58) Field of Classification Search
None
See application file for complete search history.

(56) References Cited

U.S. PATENT DOCUMENTS

| 4,176,027 A | 11/1979 | Gotcher et al. |
| 2013/0041111 A1 | 2/2013 | Yamaura et al. |

FOREIGN PATENT DOCUMENTS

| DE | 1932305 A | * 3/1970 | ............. C08G 59/26 |
| DE | 3003356 A | * 8/1981 | ........... C07D 487/04 |
| FR | 2032087 | 11/1970 | |
| JP | 54-103881 | 8/1979 | |
| JP | 11-171887 | 6/1999 | |
| JP | 2000-51337 | 2/2000 | |
| WO | 2011/102230 | 8/2011 | |

OTHER PUBLICATIONS

International Search Report dated Feb. 17, 2015 in International Application No. PCT/JP2014/081009.
Chuan-Qiang Li, et al., "Poly[μ-aqua-triaqua[μ₆-1,3,4,6-tetrakis(carboxlatometliryl)-7,8-diphenyl-glycoluril]dizinc] monohydrate]", Acta. Cryst., 2011, E67, p. m1818-m1819, supl-sup12, sup-1, Ligand L.
STN International Registry File [Online], Oct. 3, 2013, CAS Registry No. RN:1454838-83-5, Retrieved on Feb. 3, 2015.
STN International Registry File [Online], Oct. 3, 2013, CAS Registry No. RN:1454838-82-4, Retrieved on Feb. 3, 2015.
Julie Rivollier et al., "Extension of the Bambus[n]uril Family: Microwave Synthesis and Reactivity of Allylbambus[n]urils", Organic Letters, Jan. 15, 2013, 15(3), p. 480-483, Scheme 2, Compound 1.

* cited by examiner

*Primary Examiner* — Sanza Mcclendon
(74) *Attorney, Agent, or Firm* — Wenderoth, Lind & Ponack, L.L.P.

(57) ABSTRACT

The invention provides a glycoluril represented by the general formula (Z):

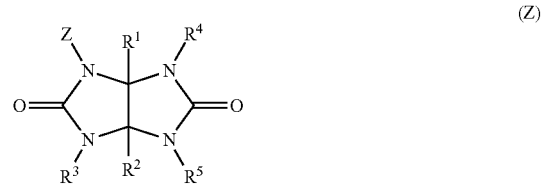

wherein the group Z represents a carboxyalkyl, a glycidyl or an allyl group; $R^1$ and $R^2$ each independently represents a hydrogen atom, a lower alkyl or a phenyl group; $R^3$, $R^4$ and $R^5$ each independently represents a hydrogen atom or the group identical with the group Z; however, when the group Z is a carboxyalkyl group, $R^3$, $R^4$ and $R^5$ are the same carboxyalkyl groups as the group Z; and when the group Z is an allyl group, $R^5$ represents a hydrogen atom. The invention further provides various resin compositions, for example, polyester resin compositions, epoxy resin compositions, and silicone resin compositions each comprising the glycoluril.

17 Claims, 10 Drawing Sheets

GLYCOLURILS HAVING FUNCTIONAL GROUPS AND USE THEREOF

TECHNICAL FIELD

The present invention relates to glycolurils having a functional group and the use thereof. In particular, the invention relates to glycolurils which have at least one carboxyalkyl, glycidyl or allyl group in the molecule as a functional group, and which are accordingly useful as a component for various resin compositions because of the functional group. The invention further relates to various useful resin compositions comprising the above-mentioned glycolurils as use thereof.

BACKGROUND ART

Glycolurils, which are heterocyclic compounds having four urea-based nitrogens in its ring structure, have been used in various applications and for production of new functional compounds, based on the reactivity of the urea-based nitrogens.

On the other hand, compounds having highly reactive functional groups, for example, allyl groups in a plural number in the molecule, such as triallyl isocyanurate, are well known as a crosslinking agent for synthetic resins and rubbers. Similarly, tetraallylglycolurils having four allyl groups in the molecule, which function as a crosslinking agent for synthetic resins and rubbers, are also known.

However, for example, glycoluril compounds of which the hydrogen atoms on all of the four nitrogen atoms are substituted with carboxyalkyl groups are expected to function as a crosslinking agent for epoxy resins and others, but no such compound is hitherto known. In addition, compounds having plural glycidyl groups in the molecule as functional groups, such as triglycidyl isocyanurate that has three glycidyl groups in the molecule, have been well known as a crosslinking agent for epoxy resins.

However, glycoluril compounds of which the hydrogen atom on at least one nitrogen atom is substituted with a glycidyl group, are not hitherto known.

Such glycoluril compounds of which the hydrogen atom on at least one nitrogen atom is substituted with a glycidyl group are useful as synthetic intermediates for oxygen-containing compounds; glycolurils having one epoxy group in the molecule are useful, for example, as reactive diluents for epoxy resins; and glycolurils having two or more epoxy groups in the molecule are expected to be useful, for example, as crosslinking agents for epoxy resins.

As described above, although tetraallylglycolurils are already known, glycolurils having one allyl group in the molecule, which are useful, as they are, for example, as synthetic intermediates, and allylglycolurils having two or three allyl groups in the molecule, which are expected to be useful as crosslinking agents for synthetic resins and rubbers, are not hitherto known.

Thus, the basic invention of the present invention relates to a new glycoluril having a carboxyalkyl, glycidyl or allyl group as the functional group. The present invention further relates to various useful resin compositions comprising a glycoluril having a carboxyalkyl, a glycidyl or an allyl group as the functional group that may partially include already known glycolurils.

Accordingly, the present invention provides the above-mentioned basic invention, and in addition, a first, a second and a third inventions which relate to resin compositions comprising the glycoluril having a carboxyalkyl, a glycidyl or an allyl group as the functional group. Hereinafter, the background of the first, second and third inventions will be described.

First Invention

In particular, the first invention of the present invention relates to the following two inventions:

(1) a new tetrakis(carboxyalkyl)glycoluril and its use, particularly as an epoxy resin composition comprising the tetrakis(carboxyalkyl)glycoluril as a crosslinking agent.

(2) a polyester resin composition for use in powder paints comprising the polyester resin obtained by polycondensation reaction of the above-mentioned tetrakis(carboxyalkyl) glycoluril with glycols.

Powder paints have advantages over solvent-type paints, for example, that they are pollution-free paint generating no organic volatile materials, give thick coated product in one application, permit use of the coated product immediately after coating, are relatively cheap, and can be recovered and reused. Thus, recently there are rapidly increasing demand for them as protective decorative paints for home electrical appliances, building materials, automobile parts and others.

Epoxy resin-, acrylic resin- and polyester resin-based paints have been mainly used as powder paints and, in particular, polyester resin-based powder paints provide coating film with favorably balanced performance.

It is needed for production of a powder paint superior in weather resistance to improve the weather resistance of the main component polyester resin, and normally, polyester resins having higher copolymerization ratios of isophthalic acid as a carboxylic acid component and neopentylglycol as a glycol component are used.

Since isophthalic acid has an absorption region different from the wavelength region of solar light energy and neopentylglycol has no hydrogen atoms at the β-carbons, polyesters containing larger amounts of these components are known to be resistant to photodegradation and show favorable weather resistance.

Isocyanate-based curing agents used in the polyester resin-based powder paints have hydroxyl groups at main terminals, and have a structure which is unreactive at a certain temperature or lower by blocking the highly reactive isocyanate group therein with a blocking agent; however, they contaminate a baking oven as the blocking agent dissociates when they are baked, and thus the use of them is not desired.

Although triglycidyl isocyanurate-based curing agents contain no blocking agent, they show mutagenicity and thus use of them is unfavorable from the point of safety.

Recently, hydroxyalkyl amides are attracting attention as a curing agent, replacing the triglycidyl isocyanurate curing agents. Powder paints containing a hydroxyalkyl amide as a curing agent permit low-temperature baking and give no volatile materials during baking. Thus, they are clean paints that have no load on environment.

However, powder paints containing a hydroxyalkyl amide as a curing agent has a disadvantage that they are lower in the smoothness and substrate adhesiveness of the coated film, in particular, in adhesiveness after water- and humidity-resistance treatments.

Although a powder paint of a polyester resin which is obtained from an aromatic dicarboxylic acid and an aliphatic diol, and has a particular viscosity and a particular acid value is proposed to overcome such disadvantages (see Patent Document 1), the powder paint does not show satisfactory weather resistance, though it is superior in smoothness and substrate adhesiveness of the coated film.

Also proposed is a powder paint comprising a resin which is obtained by depolymerization of a polyester resin from isophthalic acid and neopentylglycol with isophthalic acid as the main component (see Patent Document 2). However, the powder paint is still insufficient in smoothness of the coated film, though it is superior in weather resistance, low-temperature curing efficiency, smoothness of coated film and substrate adhesiveness.

Second Invention

A second invention of the present invention relates to a new glycidylglycoluril of which the hydrogen atom on at least one nitrogen atom is substituted with a glycidyl group and use of the same, particularly as an epoxy resin composition comprising the same.

Thus, the second invention of the present invention relates to the following four inventions:

(1) A New Glycidylglycoluril and a Resin Composition Comprising the Same

Glycolurils having glycidyl groups as functional groups are not hitherto known, and they are expected to be useful because of the reactivity of the glycidyl group.

(2) An Epoxy Resin Composition for Use in Sealing of Optical Semiconductor Elements Generally, epoxy resin compositions obtained by using an epoxy resin such as bisphenol A epoxy resin and a curing agent such as an acid anhydride have been widely used recently as thermosetting resin compositions for sealing optical semiconductor elements such as light-emitting elements and light-receiving sensors because the cured products demand transparency.

However, recently under the trend toward higher brightness of light-emitting elements and use of light-receiving sensors in in-vehicle applications and as blue ray pickup, there is a growing demand for a thermosetting resin composition which provides a transparent sealing material superior in heat resistance or lightfastness to conventional materials.

Such being the case, for the purpose of improving the heat resistance or lightfastness of cured product from a thermosetting resin composition, there are proposed a method of raising the glass transition temperature (Tg) of cured product using a polyfunctional epoxy resin in the thermosetting resin, and also a method of suppressing photodegradation of cured product by light absorption using an alicyclic epoxy resin in the thermosetting resin (see Patent Document 3).

Examples of such epoxy resins used include triglycidyl isocyanurate. However, as the cured product from a thermosetting resin composition comprising triglycidyl isocyanurate is hard and brittle, there is caused a problem that the cured product may be cracked by heat shrinkage when the optical semiconductor element is resin-sealed. In addition, as triglycidyl isocyanurate is high in crystallinity, the thermosetting resin composition in the liquid form comprising triglycidyl isocyanurate has a problem that it inherently has not a sufficient pot life, for example, as the viscosity of the composition is increased by crystallization.

(3) A Thermosetting Resin Composition Comprising a Phenol Compound

Thermosetting resin compositions represented by epoxy resin compositions are superior in processability and the cured products therefrom show favorable electrical properties, heat resistance, adhesiveness, moisture resistance (water resistance) and other properties and thus, thermosetting resin compositions have been used widely in the fields of electric and electronic parts, structural materials, adhesives, paints and others.

However, recently along with the technical advances in the electric and electronic fields, there exists a demand for further improvement in the resins used as raw materials, for example, in purity, moisture resistance, adhesiveness and dielectric properties, and for low viscosity for higher filling efficiency of filler and high reactivity for shortening the molding cycle.

In applications for aerospace materials, leisure and sport devices, for example, light-weight materials superior in mechanical properties are demanded as structural materials.

In particular in the fields of semiconductor sealing and substrates (substrates and the associated materials), as reduction in size and weight and increase in functionality of electronic devices proceed further, LSI and chip components are integrated further more densely and the shape thereof is also changing rapidly toward higher pin count and smaller size. Thus, in the fields of printed wiring board, developments for fine wiring are under progress for improvement in mounting density of electronic parts.

A method of producing a printed wiring board that satisfies these requirements is a build-up method, which is becoming a mainstream method for reduction in weight and size and for finer wiring.

Under increasing environmental consciousness, there is also an activated movement toward establishment of regulations on materials, including electronic parts, possibly discharging hazardous substances during combustion. Bromine compounds have been used as flame retardants for conventional printed wiring boards, but these compounds may generate hazardous substances during combustion. Thus, the use of bromine compounds would be prohibited in the near future.

Lead-free solders are also being commercialized as the solders generally used for connection of electronic parts to printed wiring boards. The lead-free solders have a processing temperature approximately 20° C. to 30° C. higher than that of conventional eutectic solders, and thus, electronic parts should have a heat resistance higher than that of conventional ones.

A low-dielectric layer is formed on the surface of recent silicon chips for high-speed operation thereof and, as a result of the low dielectric layer formed, the silicon chips became very brittle. Conventional printed wiring boards have a thermal expansibility significantly different from that of silicon chips, and it is desired that the thermal expansibility of a printed wiring board is reduced to a value similar to that of a silicon chip for reliable connection of the printed wiring board to the silicon chip.

Generally, a method of decreasing the thermal expansibility of the entire insulation layer by adding a low-thermal expansibility inorganic filler thereto in a greater amount is employed to reduce the thermal expansibility of the printed wiring board (see, for example, Patent Document 4). However, such a method often gives many disadvantages such as deterioration of fluidity, deterioration of insulation reliability and others.

Thus, it is studied to achieve the low thermal expansion by properly selecting a suitable resin or by improving the resin. For example, in the case of an aromatic ring-containing epoxy resin, a resin composition for preparation of a low-thermal expansion insulating layer by pressure molding, which comprises an epoxy resin having a bifunctional naphthalene skeleton or a biphenyl skeleton, is proposed (see Patent Document 5); however, the resin composition comprises a filler in an amount of 80 to 92.5 vol %.

The thermal expansibility of a resin composition for wiring boards is generally reduced by a method of increasing the crosslinking density, raising the glass transition temperature (Tg) and thus lowering the thermal expansibility (see Patent Documents 6 and 7). However, it is needed to shorten molecular chain between functional groups for increase of crosslinking density, but it is difficult to shorten the molecular chain more than a particular length from the points of reactivity, resin strength and others.

In addition, an effort to introduce an imide skeleton, which is considered to be useful for higher heat resistance and lower thermal expansion, is also made and, for example, a build-up thermosetting resin composition comprising an imide group-containing aromatic diamine and an epoxy resin is proposed (see Patent Document 8). However, when a low-molecular weight polyimide compound is used as a curing agent for an epoxy resin, the resulting cured product is frequently not so much different in properties from the cured products of common epoxy resins.

(4) An Alkali-Developing Photocurable/Thermosetting Resin Composition

Generally, in printed wiring boards for use in electric products, a solder resist film is formed as a permanent protective layer on a substrate carrying a circuit of a conductor layer. The solder resist film is formed to prevent adhesion of solder on undesired regions in the soldering process for connecting (mounting) electric and electronic parts onto the printed wiring board and thus to avoid short circuiting of the circuit and protect the conductor layer.

Thus, properties such as adhesiveness to substrate and conductor layer, chemical resistance and insulating property are required for the solder resist film. As the resin composition giving a solder resist film satisfying these properties, a resin composition is known which can be developed with an aqueous alkaline solution (see Patent Document 9). However, the solder resist film obtained by curing the composition is not sufficiently flexible and has a problem that it is cracked during cutting process or during thermal shock test. Such a solder resist film with cracks does not play a role for insulation protection and may cause circuit breaking.

Resin compositions for flexible printed wiring board are also proposed (see Patent Documents 10, 11 and 12). However, solder resist films obtained by curing these compositions do not show sufficient flexibility. They also have a disadvantage that the solder heat resistance is lowered when the flexibility is improved and resin compositions with sufficient properties are yet to be proposed.

As described above, there exists a need for a resin composition giving a solder resist film that shows the basic properties demanded for solder resist film and is yet superior in flexibility and thermal shock resistance.

Third Invention

The third invention of the present invention relates to the following six inventions:

(1) A New Allylglycoluril

Compounds having plural highly reactive allyl groups in the molecule such as triallyl isocyanurate have been well known as a crosslinking agent for synthetic resins and rubbers. Similarly, tetraallylglycolurils having four allyl groups in the molecule, which function as a crosslinking agent for synthetic resins and rubbers, are also known (see Patent Document 13).

However, glycolurils having one allyl group in the molecule are useful, as they are, for example, as synthetic intermediates, and on the other hand, glycolurils having two or three allyl groups in the molecule are expected to be useful as crosslinking agents for synthetic resins and rubbers. However, these compounds are not hitherto known.

(2) An Olefinic Resin Composition

Olefinic resins that have favorable electric insulating property and solvent resistance, the various physical properties of which can be regulated, for example, by properly employing one of various crosslinking means such as radiation ray crosslinking, electron beam crosslinking, peroxide crosslinking, sulfur crosslinking and silane crosslinking with a silane compound, have been used widely in various fields including the fields of electric and electronic materials.

As described above, glycolurils, i.e., heterocyclic compounds having four urea-based nitrogen atoms in the ring structure, have been used in various applications and as intermediated materials for functional compounds, based on the reactivity of the urea-based nitrogen.

In particular, glycolurils having highly reactive allyl groups in the molecule are expected to be useful as a crosslinking agent for olefinic resins, based on the active allyl groups.

(3) A Curable Composition Superior in Adhesiveness

There are growing requirements on reliability against external environments such as light and heat in the fields of electronic and optical materials year by year. Thermosetting resins have been long used in these fields and, in particular, epoxy resins have been used widely, because of their flexibility in use and high adhesiveness to various substrates. However, they are insufficient, for example, as peripheral materials such as high-brightness light-emitting diodes and power semiconductors, from the viewpoints of long-term heat resistance and lightfastness. Glass has long been known as the material satisfying the heat resistance and lightfastness, but it also has a disadvantage that it is inferior in processability and substrate adhesiveness.

To overcome these disadvantages, organic-inorganic hybrid resins that are superior in heat resistance and lightfastness to organic polymer materials such as epoxy resins and superior in processability and adhesiveness to inorganic polymers such as glass have been used widely. In particular, thermosetting resins prepared by making use of hydrosilylation reaction, which is an addition reaction of a hydrosilyl group to a carbon-carbon double bond, are proposed (see, for example, Patent Documents 14, 15 and 16), and these resins are found to show favorable heat resistance, lightfastness and adhesiveness.

However, these resins are all insufficient from the viewpoint of optical transparency. Thus, it is difficult to apply these resins for use in optical material applications such as light-emitting diodes and display devices.

In contrast, in the case of a system having an isocyanuric acid skeleton as the organic component (see, for example, Patent Document 17), a composition which gives a thermosetting resin preserving the properties above and yet showing high transparency is proposed, but the composition has a high glass transition point, and thus has a disadvantage, for example, that, when it is coated on a substrate, the resulting film warps due to the strength of the heat stress and becomes less adhesive to the substrate.

A composition comprising a compound that has epoxy groups such as glycidyl groups as a component is proposed to overcome the problem (see, for example, Patent Document 18). However, it has a problem of trade-off relation that introduction of an epoxy group for expression of adhesiveness leads to deterioration in heat resistance and lightfastness.

Under the circumstances described above, there exists an urgent demand for a thermosetting resin which has favorable heat resistance, lightfastness and transparency, and in addition, shows smaller thermal stress, and is thus resistant to warping and superior in adhesiveness.

(4) A Thermosetting Resin Composition for Sealing Semiconductors, Comprising an Organopolysiloxane-Modified Allylglycoluril Transfer molding using a mold, potting with a liquid sealant resin, screen printing or the like is performed to seal semiconductor devices with a resin. Recently along with reduction in size of semiconductor elements, electronic devices are required to be reduced in size and thickness, and it is needed to seal a thin package carrying silicon dies stacked thereon with a resin at a thickness of 500 μm or less.

In relation to the present invention, various applications of isocyanurate compounds similar to glycolurils are proposed.

Example of the known compositions comprising an isocyanurate ring-containing polymer and an isocyanurate ring-containing terminal hydrogen polysiloxane polymer include: compositions comprising an epoxy group ring-opening polymerizable polysiloxane composition obtained by addition reaction of diallyl monoglycidyl isocyanurate to a Si—H group-containing polysiloxane (see Patent Document 19), compositions comprising the isocyanurate ring-containing polysiloxane above and a Si—H group-containing polysiloxane (see Patent Document 20), addition-curable compositions comprising a triallyl isocyanurate and a Si—H group-containing polysiloxane (see Patent Document 21), addition-curable compositions comprising a polysiloxane having an isocyanurate ring and Si—H groups and an alkenyl group-containing cured product (see Patent Documents 22, 23 and 24) and the like.

However, although the isocyanurate ring-containing polymer composition described above, which contains siloxane bonds in the main agent, is flexible, it is lower in compatibility with a crosslinking agent. In addition, the site of the alkenyl group present is uncertain, and thus, it is difficult to cure the composition by addition reaction and thus to give the favorable characteristic (rapid curing reaction) of the hydrosilylation (addition reaction). The isocyanuric acid-containing polymer composition also has a disadvantage that it leads to high crosslinking density and is rigid and less flexible.

Under these circumstances, there is still no cured product prepared by addition reaction between an isocyanurate ring-containing polysiloxane and a Si—H group-containing polysiloxane that is superior in flexibility, curing properties and compatibility and also in steam permeation resistance.

(5) An Electron Beam-Curable Resin Composition

LED elements that are power saving and have longer lifetime are spreading recently as light sources replacing incandescent lightbulbs and others. Generally, when LED elements are used as a light source, plural elements are mounted on a metal substrate and a reflector is placed around them to improve the illuminance by reflection of light.

However, a device employing such a reflector has a disadvantage that it becomes less bright as the reflectance of the reflector lowers on account of deterioration of the reflector by the heat generated during light emission.

An electron beam-curable resin composition containing triallyl isocyanurate as the crosslinking agent for polyolefin resins has been proposed to overcome the disadvantage, and it is reported that it is possible by using such a resin composition to suppress the degradation of reflector device (see Patent Document 25). However, the triallyl isocyanurate used in the resin composition is highly volatile and has a disadvantage that the amount of crosslinking agent contained is reduced during the heat molding for preparation of the cured product.

(6) A Silicone Resin Composition

Use of an epoxy resin has been proposed as the resin in compositions for sealing optical semiconductors (see, for example, Patent Document 26). However, the sealed products prepared from such epoxy resin-containing composition have a disadvantage, for example, that they turn yellow by the heat generated by a white LED element.

Also having been proposed room temperature-curable organopolysiloxane compositions containing a two silanol group-containing organopolysiloxane, a silane compound having two or more hydrolyzable groups bound to the silicon atom in the molecule or the like, and an organic zirconium compound (see Patent Documents 27 and 28). Also having been proposed adding a condensation catalyst to a mixture of a two silanol group-containing diorganopolysiloxane or the like and a silane or the like having three or more alkoxy groups, and heating the resulting mixture (see Patent Documents 29 and 30).

However, as silicone resins are higher in gas permeability than epoxy resins and thus permit easier permeation of air, they have a disadvantage that the silver plate formed on optical semiconductor package is easily discolored by hydrogen sulfide in the air and, as a result, the optical semiconductor package shows a reduced brightness. Silicone resins are generally cured to increase sulfur resistance, but it leads to disadvantages of curing shrinkage as well as exfoliation thereof from LED package and breakage of wire by the shrinkage.

CITATION LIST

Patent Literatures

Patent Document 1: JP-A No. 2003-119256
Patent Document 2: JP-A No. 2006-37015
Patent Document 3: JP-A No. 2-222165
Patent Document 4: JP-A No. 2004-182851
Patent Document 5: JP-A No. 5-148543
Patent Document 6: JP-A No. 2000-243864
Patent Document 7: JP-A No. 2000-114727
Patent Document 8: JP-A No. 2000-17148
Patent Document 9: JP-A No. 1-141904
Patent Document 10: JP-A No. 7-207211
Patent Document 11: JP-A No. 8-274445
Patent Document 12: JP-A No. 9-5997
Patent Document 13: JP-A No. 11-171887
Patent Document 14: JP-A No. 3-277645
Patent Document 15: JP-A No. 7-3030
Patent Document 16: JP-A No. 9-302095
Patent Document 17: WO 02/053648 pamphlet
Patent Document 18: JP No. 4216512
Patent Document 19: JP-A No. 2008-143954
Patent Document 20: JP-A No. 2008-150506
Patent Document 21: JP-A No. 9-291214
Patent Document 22: JP No. 4073223
Patent Document 23: JP-A No. 2006-291044
Patent Document 24: JP-A No. 2007-9041
Patent Document 25: JP-A No. 2013-166926
Patent Document 26: JP-A No. 10-228249
Patent Document 27: JP-A No. 2001-200161
Patent Document 28: JP-A No. 2-196860
Patent Document 29: JP-A No. 2007-224089
Patent Document 30: JP-A No. 2006-206700

SUMMARY OF INVENTION

Technical Program

An object of the present invention is to provide a new glycoluril having functional groups and various resin compositions comprising the same as the basic invention. Under the technical circumstances described above, the object of the present invention is, in particular, to provide the following first, second and third inventions.

First Invention

An object of the first invention of the present invention is to provide:
(1) a new tetrakis(carboxyalkyl)glycoluril and use thereof, particularly as an epoxy resin composition comprising the tetrakis(carboxyalkyl)glycoluril, and
(2) a polyester resin composition for use in powder paints giving a powder paint that provides a coated film superior in weather resistance, smoothness and low-temperature curing efficiency.

Second Invention

An object of the second invention of the present invention is to provide:
(1) a new glycidylglycoluril and use thereof, particularly as a resin composition comprising the same, and
(2) an epoxy resin composition for use in sealing of optical semiconductor elements.

The inventors have studied intensively to obtain a liquid sealing material for optical semiconductor elements that has a long pot life and is additionally superior in heat resistance and lightfastness. After studies mainly for improvement of the properties of triglycidyl isocyanurate traditionally used, focusing on the epoxy resin component itself, the inventors have found that it is possible to give a cured product improved in heat resistance and lightfastness without deterioration in high transparency when an allylglycoluril, or a liquid epoxy resin, is used, and made the present invention relating to the epoxy resin composition for use in sealing of optical semiconductor elements.

(3) Another object of the second invention of the present invention is to provide a thermosetting resin composition comprising a phenol compound.

After intensive studies to overcome the disadvantages described above, the inventors have found that it is possible to achieve the desired objects by using a glycidylglycoluril as an epoxy compound (resin) and made the present invention.

In other words, an object of the invention is to provide a thermosetting resin composition giving a cured product superior not only in flame resistance but also in heat resistance and toughness that is useful in applications such as insulating materials for electric electronic parts (high-reliability semiconductor sealing materials, etc.), laminated boards (printed wiring board, build-up board, etc.), various composite materials such as CFRPs, adhesives, paints and others.

(4) Still another object of the invention is to provide an alkali-developing photocurable/thermosetting resin composition.

After intensive studies to overcome the disadvantages described above, the inventors have found that it is possible to achieve the desired objects by preparing a photocurable/thermosetting resin composition comprising a glycidylglycoluril as an epoxy compound and made the present invention.

Thus, the object of the invention is to provide a photocurable/thermosetting resin composition giving a cured film superior both in flexibility and thermal shock resistance without deterioration in properties such as solder heat resistance, thermal degradation resistance, and acid resistance and a printed wiring board having a solder resist film (cured film) formed thereon using the same.

Third Invention

An object of the third invention of the present invention is to provide:
(1) a new allylglycoluril and the following various useful resin compositions comprising the same.
(2) An olefinic resin composition An object of the invention is to provide an olefinic resin composition suitable for a raw material for olefinic resin having a crosslinking structure.

(3) A curable composition superior in adhesiveness

An object of the present invention is to provide a curable composition comprising, as an essential component, a tetraallylglycoluril as an alkenyl group-containing organic compound, which gives a cured product showing smaller heat stress and thus superior adhesiveness without deterioration in heat resistance and lightfastness.

(4) A thermosetting resin composition for sealing semiconductors comprising an organopolysiloxane-modified allylglycoluril The inventors have found that a thermosetting resin composition comprising a particular organopolysiloxane polymer blocked with allylglycoluril rings at both terminals (base polymer) and a particular glycoluril ring-containing terminal hydrogen polysiloxane polymer (crosslinking agent), respectively as the main agent (base polymer), and a curing agent (crosslinking agent), and additionally a curing accelerator gives, when used for sealing a semiconductor device, a sealed product that is superior in water resistance and gas transmittance to conventional silicone compounds, resistant to warping and does not have even a slight amount of tacks on the surface of the cured product, and thus that it is highly flexible in use, and made the present invention.

Thus, an object of the present invention is to provide a thermosetting resin composition giving a semiconductor device substantially resistant to warping and superior in heat resistance and moisture resistance when used in sealing a semiconductor element, and a semiconductor device sealed with such a resin composition.

(5) An electron beam-curable resin composition

An object of the present invention is to provide an electron beam-curable resin composition which gives a cured product superior in heat resistance and is suitably used for preparing a reflector.

(6) A silicone resin composition

An object of the present invention is to provide a silicone resin composition which gives a cured product superior in sulfur resistance and transparency.

Solution to Problem

The present invention provides, as the basic invention, a new glycoluril having functional groups represented by the general formula (Z):

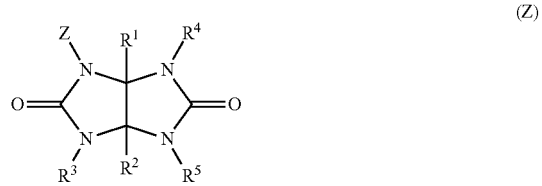

wherein the group Z represents a carboxyalkyl, a glycidyl or an allyl group; $R^1$ and $R^2$ each independently represents a hydrogen atom, a lower alkyl or a phenyl group; $R^3$, $R^4$ and $R^5$ each independently represents a hydrogen atom or a group identical with the group Z; however, when the group Z is a carboxyalkyl group, $R^3$, $R^4$ and $R^5$ each represents the carboxyalkyl group identical with the group Z; and when the group Z is an allyl group, $R^5$ represents a hydrogen atom.

The present invention also provides the following first, second, and third inventions, based on the new glycoluril having the functional groups described above.

First Invention (1) A New Tetrakis(Carboxyalkyl)Glycoluril and an Epoxy Resin Composition Comprising the Same The present invention provides a 1,3,4,6-tetrakis(carboxyalkyl)-glycoluril represented by the general formula (A):

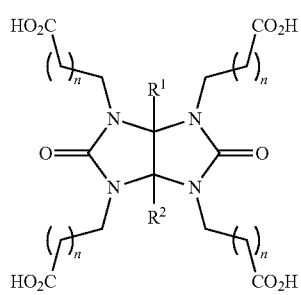

wherein n is 0 or 1; and $R^1$ and $R^2$ each independently represents a hydrogen atom or a lower alkyl group.

The present invention also provides, as an application thereof, a crosslinking agent for epoxy resins comprising the 1,3,4,6-tetrakis-(carboxyalkyl)glycoluril. The invention further provides an epoxy resin composition comprising the curing agent for epoxy resins and an amine as a crosslinking agent.

The 1,3,4,6-tetrakis(carboxyalkyl)glycoluril according to the invention is a new compound wherein the hydrogen atoms on the four nitrogen atoms in the molecule are all substituted by carboxylalkyl groups. Thus, it is a glycoluril having four carboxyl groups in the molecule.

Since the 1,3,4,6-tetrakis(carboxyalkyl)glycoluril according to the invention is a tetrafunctional compound, it gives, for example, when used as a crosslinking agent for epoxy resins, cured epoxy resin products higher in crosslinking density than those obtained by using a conventional bifunctional or trifunctional crosslinking agent, and thus cured epoxy resin products superior, for example, in hardness, heat resistance and moisture resistance. Accordingly, it is useful, for example, as a crosslinking agent for epoxy resins and a solder flux activator.

(2) A Polyester Resin Composition

The polyester resin composition for use in powder paints according to the invention comprises:
(a) a polyester resin obtained by polycondensation reaction of the 1,3,4,6-tetrakis(carboxyalkyl)glycoluril represented by the general formula (A) and a glycol, and
(b) a β-hydroxyalkyl amide as a curing agent.

Such a resin composition for use in powder paints provides a powder paint that gives a coated film superior in weather resistance, smoothness and low-temperature curing efficiency.

Second Invention (1) A New Glycidylglycoluril and an Epoxy Resin Composition Comprising the Same The invention provides a glycidylglycoluril represented by the general formula (B):

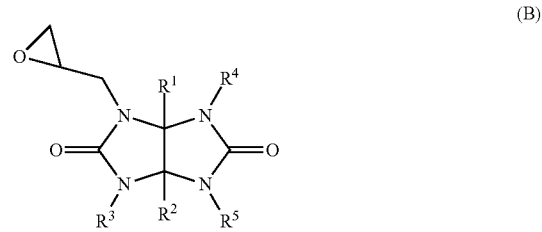

wherein $R^1$ and $R^2$ each independently represents a hydrogen atom, a lower alkyl or a phenyl group; and $R^3$, $R^4$ and $R^5$ each independently represents a hydrogen atom or a glycidyl group.

The invention further provides a crosslinking agent for epoxy resins as use of the glycidylglycoluril. The invention also provides an epoxy resin composition comprising the crosslinking agent for epoxy resins.

The glycidylglycoluril according to the invention is a new compound wherein at least one of the hydrogen atoms bound to the four nitrogen atoms in the glycoluril is replaced with a glycidyl group.

Therefore, such a compound is useful as a synthetic intermediate for new oxygen-containing compounds and those having one glycidyl group in the molecule are useful, for example, as a reactive diluent for epoxy resins. Alternatively, those having two or more glycidyl groups in the molecule are useful, for example, as a crosslinking agent for epoxy resins.

In particular, because the 1,3,4,6-tetraglycidylglycolurils wherein the hydrogen atoms on all nitrogen atoms are replaced by glycidyl groups are tetrafunctional, they give, for example, when used as an crosslinking agent for epoxy resins, a cured epoxy resin product higher in crosslinking density than those obtained by using a conventional bifunctional or trifunctional crosslinking agent, and thus a cured epoxy resin product further superior, for example, in hardness and heat resistance.

(2) An Epoxy Resin Composition for Use in Sealing of Optical Semiconductor Elements The epoxy resin composition for use in sealing of optical semiconductor elements according to the invention comprises an epoxy resin (1) wherein at least one component in the epoxy resin (1) is a glycidylglycoluril represented by the above-mentioned general formula (B).

It is preferred that the epoxy resin composition for use in sealing of optical semiconductor elements according to the invention comprises additionally at least one component selected from glass fillers, curing agents, curing accelerators, curing catalysts, polyester resins, organosiloxanes, rubber particles and additives.

The glycidylglycoluril in the epoxy resin composition for use in sealing of optical semiconductor elements according to the present invention has at least one glycidyl group (epoxy group) in the molecule and is liquid at room temperature. Therefore, the resin composition is resistant to crystallization during storage and, as a result, provides an enough pot life during resin sealing and gives a sealed product with high glass transition temperature (Tg), high strength, superior transparency and lightfastness.

Therefore, it is possible by using the epoxy resin composition for use in sealing of optical semiconductor elements according to the invention, to improve the production efficiency and give an optical semiconductor device with high optical transparency and also with superior heat resistance and lightfastness. Accordingly, it is possible by sealing an optical semiconductor element with the resin composition according to the invention to obtain a high-reliability optical semiconductor device.

Further, the epoxy resin composition according to the invention which is liquid during handling is also superior in handleability during the sealing operation. Thus, the epoxy resin composition according to the invention is used suitably as a resin composition for sealing optical semiconductors.

The epoxy resin composition according to the invention is also used in applications such as adhesives, electric insulating materials, laminated boards, coating, ink, paints, sealants, resists, composite materials, transparent substrates, transparent sheets, transparent films, optical elements, optical lenses, optical parts, optical shaped materials, electronic papers, touch panels, solar cell substrates, optical waveguides, light guides, and holography memories.

(3) A Thermosetting Resin Composition Comprising a Phenol Compound

The thermosetting resin composition of the invention comprises a glycidylglycoluril represented by the general formula (B) mentioned above and a phenol resin as components.

The thermosetting resin composition according to the invention gives a cured product superior in flame resistance, heat resistance and toughness and is thus useful for various composite materials including insulating materials for electric/electronic parts (high-reliability semiconductor sealing material, etc.), laminated boards (printed wiring boards, build-up boards, etc.) and CFRPs, adhesives, paint and others.

(4) An Alkali-Developing Photocurable/Thermosetting Resin Composition

The alkali-developing photocurable/thermosetting resin composition according to the invention comprises:
(a) a glycidylglycoluril represented by the general formula (B) above,
(b) a photosensitive prepolymer having two or more unsaturated double bonds in the molecule and
(c) a photopolymerization initiator.

The alkali-developing photocurable/thermosetting resin composition according to the invention preferably further comprises an epoxy compound or an epoxy resin other than the glycidylglycoluril represented by the general formula (B) above.

The alkali-developing photocurable/thermosetting resin composition according to the invention preferably comprises a diluent, a polybutadiene compound and a polyurethane compound.

The photocurable/thermosetting resin composition according to the invention gives a cured film superior both in flexibility and thermal shock resistance without any deterioration in basic properties required for solder resist films such as solder heat resistance and thermal degradation resistance. Thus, it can be used suitably for preparation of a solder resist film on printed wiring boards for various applications.

In addition, the photocurable/thermosetting resin composition according to the invention gives a cured film superior in flexibility to those prepared by using a known photosensitive resin composition traditionally used for flexible printed wiring board and a cured film superior in thermal shock resistance to those prepared by using a known photosensitive resin composition traditionally used for printed wiring boards for BGA or CSP.

Third Invention (1) A New Allylglycoluril

The new allylglycoluril according to the invention is represented by the general formula (C0):

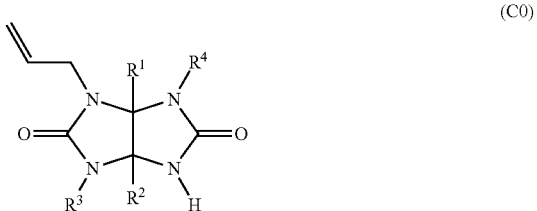

(C0)

wherein $R^1$ and $R^2$ each independently represents a hydrogen atom, a lower alkyl or a phenyl group; and $R^3$ and $R^4$ each independently represents a hydrogen atom or an allyl group.

The allylglycoluril according to the invention is a new compound wherein one to three nitrogen atoms in glycolurils are substituted with allyl groups.

Among the allylglycolurils according to the invention, the glycolurils having one allyl group in the molecule are useful, as they are, for example, as a synthetic intermediate, and the glycolurils having two or three allyl groups in the molecule are expected to be useful as a crosslinking agent for synthetic resins and synthetic rubbers.

(2) An Olefinic Resin Composition

An olefinic resin composition according to the invention comprises an allylglycoluril represented by the general formula (C):

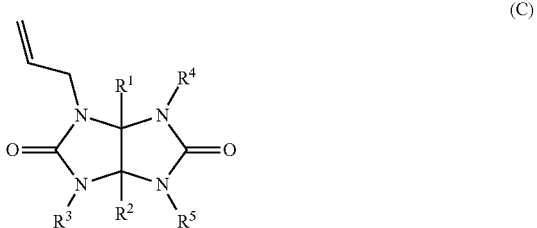

(C)

wherein $R^1$ and $R^2$ each independently represents a hydrogen atom, a lower alkyl or a phenyl group; and $R^3$, $R^4$ and $R^5$ each independently represents a hydrogen atom or an allyl group, and an olefinic polymer.

Various molded products such as films, sheets and cases (containers) that are prepared by preparing a crosslinked product (resin) by crosslinking the olefinic resin composition according to the invention and molding it are superior in transparency, and also in mechanical and physical properties such as resolution, electric insulating properties, heat resistance, low hygroscopicity, hydrolysis resistance, weather resistance, adhesiveness and elasticity.

(3) A Curable Composition Superior in Adhesiveness

The curable composition according to the invention comprises:
(A) an alkenyl group-containing organic compound,
(B) a compound having at least three hydrosilyl groups in the molecule, and
(C) a hydrosilylation catalyst, wherein a tetraallylglycoluril represented by the general formula (C1):

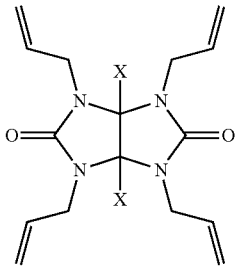

wherein X represents a hydrogen atom, an alkyl or an aryl group is contained as the component (A) as an essential component.

The curable composition according to the invention gives a cured product that is superior in heat resistance and lightfastness, shows a lower heat stress and is thus superior in adhesiveness and resistant to warping.

(4) A Thermosetting Resin Composition for Use in Sealing of Semiconductors Comprising an Organopolysiloxane-Modified Allylglycoluril The thermosetting resin composition according to the invention comprises:

(A) an organopolysiloxane polymer represented by the general formula (C3):

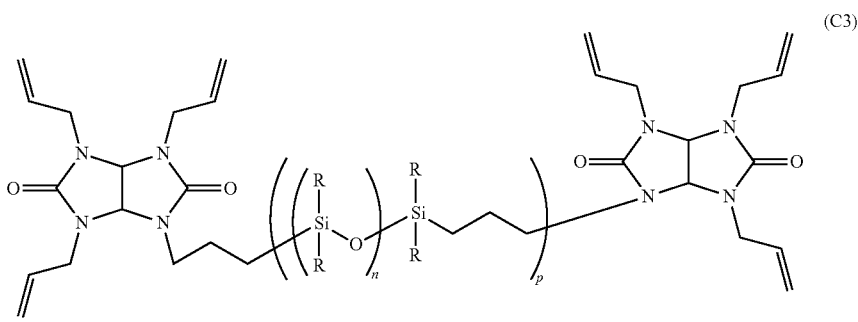

wherein each R independently represents an alkyl or a phenyl group; n is an integer of 1 to 50; and p is an integer of 1 to 30, as an alkenyl group-containing organopolysiloxane, (B) a glycoluril ring-containing organohydrogen polysiloxane polymer represented by the general formula (C4):

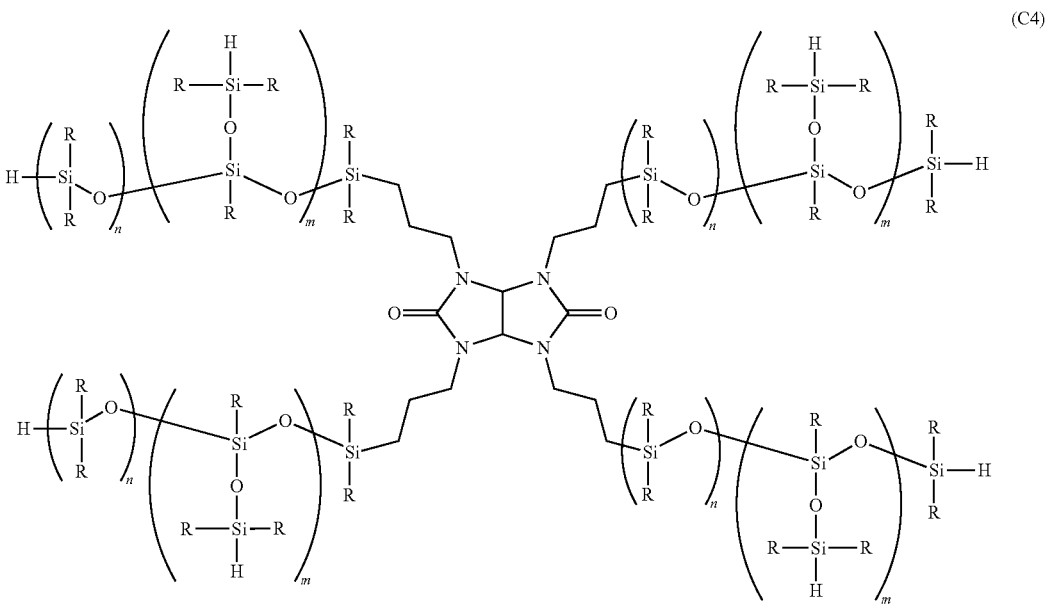

wherein each R independently represents an alkyl or a phenyl group; n is an integer of 1 to 50; m is an integer of 0 to 5; and each siloxane recurring unit in the general formula above may be bound at random, as an organohydrogen polysiloxane, and (C) a curing accelerator.

The thermosetting resin composition according to the present invention preferably further comprises (D) an inorganic filler.

In the thermosetting resin composition according to the present invention above, the ratio of the Si—H group in component (B) to 1 mole of the allyl group in component (A) is 0.8 to 4.0 moles.

The thermosetting resin composition according to the invention gives, when used to seal a semiconductor element, a semiconductor device substantially resistant to warping and also superior in heat resistance and moisture resistance.

(5) An Electron Beam-Curable Resin Composition

The electron beam-curable resin composition according to the invention comprises a polyolefin resin and a crosslinking agent, wherein the crosslinking agent is an isocyanurate compound represented by the general formula (C5):

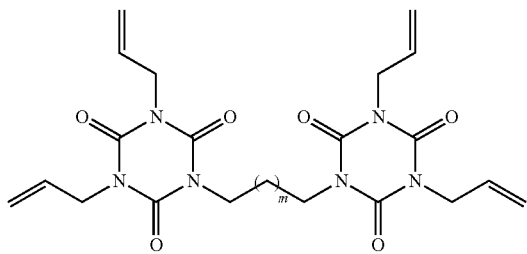

(C5)

wherein m is an integer of 0 to 16, or the general formula (C6)

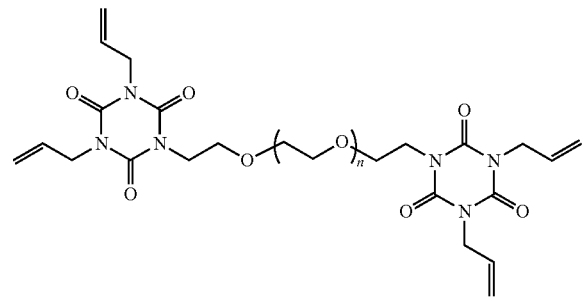

(C6)

wherein n is an integer of 0 or 1.

Further, the electron beam-curable resin composition according to the invention comprises a polyolefin resin and a crosslinking agent, wherein the crosslinking agent is an allylglycoluril represented by the general formula (C) above.

The electron beam-curable resin composition according to the invention is suitably used for preparation of reflectors and gives a cured product superior in heat resistance.

(6) A Silicone Resin Composition

The silicone resin composition according to the invention comprises:

component (A): a polysiloxane having at least two silicon-bound alkenyl groups, component (B): a polysiloxane crosslinking agent having at least two silicon-bound hydrogen groups, component (C): a hydrosilylation reaction catalyst, and component (D): an allylglycoluril represented by the general formula (C) above, wherein the component (D) is contained in an amount of 0.1 to 10 parts by mass with respect to 100 parts by mass of the total amount of the components (A) and (B) above.

It is preferred that the silicone resin composition according to the invention does not substantially contain a silanol group-containing silicon compound.

The alkenyl group in the silicone resin composition according to the invention is preferably a vinyl or a (meth) acryloyl group.

The silicone resin composition according to the invention is suitably used, in particular, as a sealant resin composition for optical semiconductor elements.

The silicone resin composition according to the invention gives a cured product superior in sulfur resistance and transparency.

DESCRIPTION OF EMBODIMENTS

Figure 1:
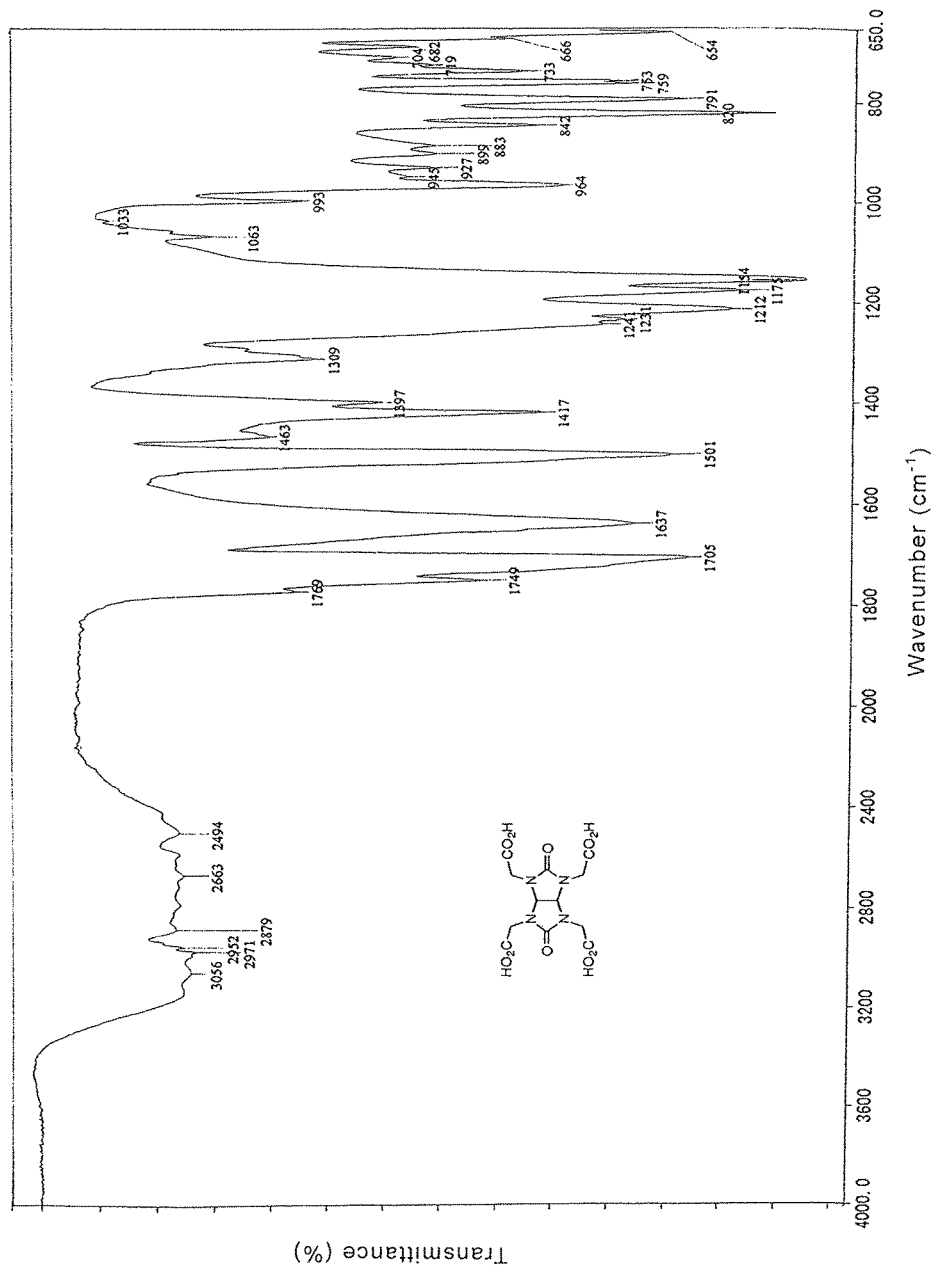
FIG. 1 shows an IR spectrum of 1,3,4,6-tetrakis(carboxymethyl)-glycoluril.

Hereinafter, the basic invention, and the first, second and third inventions of the present invention will be described in detail.

Basic Invention

The basic invention of the present invention relates to a glycoluril represented by the general formula (Z):

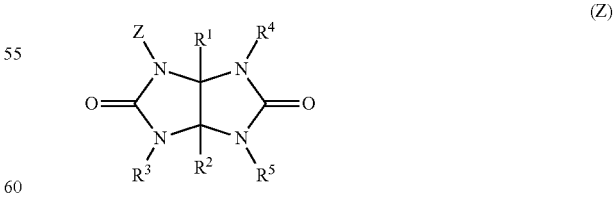

(Z)

wherein the group Z represents a carboxyalkyl, a glycidyl or an allyl group; $R^1$ and $R^2$ each independently represents a hydrogen atom, a lower alkyl or a phenyl group; $R^3$, $R^4$ and $R^5$ each independently represents a hydrogen atom or a group identical with the group Z; however, when the group Z is a carboxyalkyl group, $R^3$, $R^4$ and $R^5$ each represents the carboxyalkyl group identical with the group Z; and when the group Z is an allyl group, $R^5$ represents a hydrogen atom.

Thus, the glycoluril according to the invention relates to: 1,3,4,6-tetrakis(carboxyalkyl)glycoluril when the group Z in the general formula (Z) above is a carboxylalkyl group; mono-, di-, tri- or tetraglycidylglycoluril when the group Z is a glycidyl group; and mono-, di- or triallylglycoluril when the group Z is an allyl group.

Hereinafter, a 1,3,4,6-tetrakis(carboxyalkyl)glycoluril and a resin composition comprising the same will be described in detail as the first invention, a glycidylglycoluril and a resin composition comprising the same as the second invention, and an allylglycoluril and the resin composition comprising the same as the third invention.

First Invention (1) A New 1,3,4,6-Tetrakis(Carboxyalkyl)Glycoluril and an Epoxy Resin Composition Comprising the Same The 1,3,4,6-tetrakis(carboxyalkyl)glycoluril according to the invention is represented by the general formula (A):

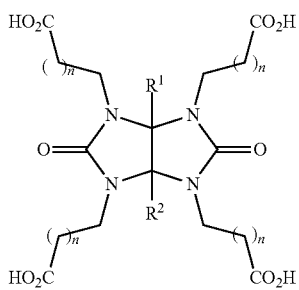

(A)

wherein n is 0 or 1; and $R^1$ and $R^2$ each independently represents a hydrogen atom or a lower alkyl group.

When $R^1$ or $R^2$ is a lower alkyl group in the 1,3,4,6-tetrakis-(carboxyalkyl)glycoluril represented by the general formula (A), the lower alkyl group usually has 1 to 5 carbon atoms, preferably 1 to 3 carbon atoms, most preferably one carbon atom, and thus, the most preferable lower alkyl group is a methyl group.

Accordingly, preferred concrete examples of the 1,3,4,6-tetrakis(carboxyalkyl)glycolurils according to the invention include:
1,3,4,6-tetrakis(carboxylmethyl)glycoluril,
1,3,4,6-tetrakis(2-carboxylethyl)glycoluril,
1,3,4,6-tetrakis(carboxylmethyl)-3a-methylglycoluril,
1,3,4,6-tetrakis(2-carboxylethyl)-3a-methylglycoluril,
1,3,4,6-tetrakis(carboxylmethyl)-3a,6a-dimethylglycoluril,
1,3,4,6-tetrakis(2-carboxylethyl)-3a,6a-dimethylglycoluril and the like.

Among the 1,3,4,6-tetrakis(carboxyalkyl)glycolurils according to the invention wherein n is 0, i.e., 1,3,4,6-tetrakis(carboxymethyl)-glycolurils represented by the following general formula (A1):

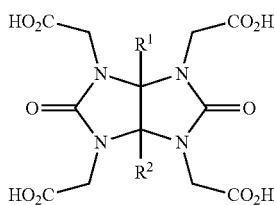

(A1)

wherein $R^1$ and $R^2$ are the same as those described above, can be prepared according to the following formula by reacting a dicarbonyl compound represented by the general formula (a):

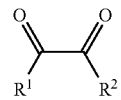

(a)

wherein $R^1$ and $R^2$ are the same as those described above, with a urea derivative (b) represented by the general formula (b):

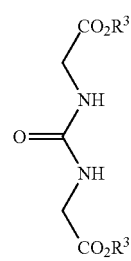

(b)

wherein, $R^3$ represents a lower alkyl group, as needed, in a suitable solvent in the presence of an acid.

The ester group ($—CO_2R^3$) in the urea derivative (b) is an ester group that is hydrolyzed during reaction and the group $R^3$ is preferably an alkyl group having 1 to 3 carbon atoms, more preferably a methyl or an ethyl group. Examples of the urea derivatives (b) preferably used include N,N'-carbonyl-bis(glycine methyl) and N,N'-carbonylbis(glycine ethyl).

The urea derivative (b) is preferably used in an amount of 2 to 10 mole parts, preferably 2 to 4 mole parts, with respect to 1 mole part of the dicarbonyl compound (a).

Examples of the dicarbonyl compounds (a) used include glyoxal, 2-oxopropanal, diacetyl and the like.

Examples of the acids used in the reaction of the dicarbonyl compound (a) with the urea derivative (b) include inorganic acids such as hydrochloric acid and sulfuric acid, and organic acids such as acetic acid. These acids are used usually in an amount of 0.05 to 10 mole parts, preferably 0.1 to 1.0 mole parts, with respect to 1 mole part of the dicarbonyl compound (a).

If a solvent is used in the reaction of the dicarbonyl compound (a) with the urea derivative (b), the solvent is not particularly limited if it does not inhibit the reaction. Examples thereof include water, alcohols such as methanol, ethanol and isopropyl alcohol; aliphatic hydrocarbons such as hexane and heptane; ketones such as acetone and 2-butanone; esters such as ethyl acetate and butyl acetate; aromatic hydrocarbons such as benzene, toluene and xylene; halogenated hydrocarbons such as methylene chloride, chloroform, carbon tetrachloride, chlorotrifluoromethane, dichloroethane, chlorobenzene and dichlorobenzene; ethers such as diethyl ether, diisopropyl ether, tetrahydrofuran, dioxane, dimethoxyethane and diethylene glycol dimethyl ether; amides such as formamide, N,N-dimethylformamide, N,N-dimethylacetamide, N-methyl-2-pyrrolidone, N-methylpyrrolidinone and hexamethylphosphorotriamide; sulfoxides such as dimethylsulfoxide and the like. These solvents are used alone or in combination of two or more in a suitable amount.

The reaction of the dicarbonyl compound (a) with the urea derivative (b) is normally carried out at a temperature in the range of −10° C. to 150° C., and preferably at a temperature in the range of 0° C. to 100° C. Although the reaction time varies according to the reaction temperature, it is normally in the range of 1 to 24 hours, and preferably in the range of 1 to 6 hours.

Desired 1,3,4,6-tetrakis(carboxymethyl)glycoluril can be obtained from the reaction mixture obtained after the reaction of the dicarbonyl compound (a) with the urea derivative (b), for example, by means of an operation such as extraction. The desirable 1,3,4,6-tetrakis-(carboxymethyl)glycoluril may be purified, as needed, additionally, for example, by washing with a solvent such as water or by treatment with activated carbon.

Among the 1,3,4,6-tetrakis(carboxyalkyl)glycolurils according to the invention, the compound wherein n is 1, i.e., 1,3,4,6-tetrakis-(2-carboxyethyl)glycolurils represented by the following general formula (A2):

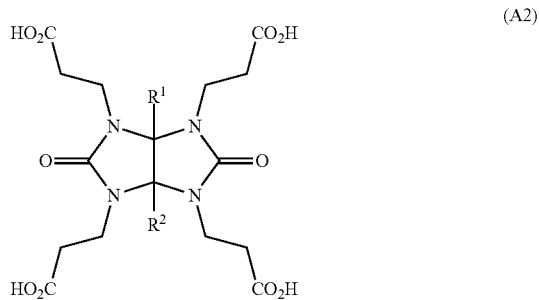

(A2)

wherein $R^1$ and $R^2$ are the same as those described above, can be prepared by a first process of reacting the glycoluril represented by the general formula (c):

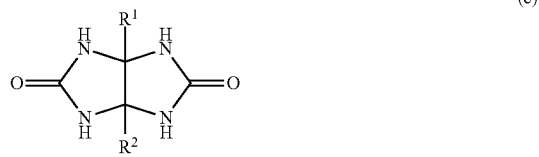

(c)

wherein $R^1$ and $R^2$ are the same as those described above, with acrylonitrile, preferably in a suitable solvent, in the presence of a base, to give 1,3,4,6-tetrakis(2-cyanoethyl) glycoluril represented by the general formula (d):

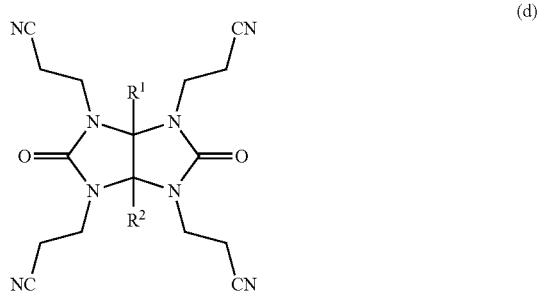

(d)

wherein $R^1$ and $R^2$ are the same as those described above, and by a subsequent second process of hydrolyzing the 1,3,4,6-tetrakis(2-cyanoethyl)-glycoluril obtained, preferably in a suitable solvent, in the presence of an acid.

In the first process, i.e., in the reaction of the glycoluril (c) with acrylonitrile, acrylonitrile is used normally in an amount of 4.0 to 20.0 mole parts, and preferably 4.0 to 8.0 mole parts, with respect to 1 mole part of the glycoluril (c).

Examples of the bases used in the first process include inorganic bases such as sodium hydroxide, potassium hydroxide, sodium carbonate, potassium carbonate, sodium methoxide, sodium ethoxide and sodium tert.-butoxide, and organic bases such as triethylamine, diisopropylethylamine and DBU (1,8-diazabicyclo[5.4.0]undec-7-ene). These bases are used normally in an amount of 0.01 to 5.0 mole parts, and preferably 0.01 to 1.0 mole part, with respect to 1 mole part of the glycoluril (c).

When a solvent is used in the first process, the solvent is not particularly limited if it does not inhibit the reaction and, for example, the solvent identical with the solvent used in the reaction of the dicarbonyl compound (a) with the urea derivative (b) may be used.

The reaction temperature and the reaction time of the first process are also the same as those of the reaction of the dicarbonyl compound (a) with the urea derivative (b).

In synthesis of 1,3,4,6-tetrakis(carboxyethyl)glycoluril in the first and second process described above, acrylonitrile and the solvent present in excess after the first process may be distilled from the reaction mixture obtained and the residue obtained may be hydrolyzed, as it is, in the second process. Alternatively, the 1,3,4,6-tetrakis(2-cyanoethyl)-glycoluril obtained may be separated from the reaction mixture by a suitable means and subjected to hydrolysis in the second process.

Examples of the acids used in the second process, i.e., in the hydrolysis of 1,3,4,6-tetrakis(2-cyanoethyl)glycoluril, include inorganic acids such as hydrochloric acid and sulfuric acid, and organic acids such as acetic acid. These acids are used normally in an amount of 0.1 to 20.0 mole parts, and preferably 1.0 to 3.0 mole parts, with respect to 1 mole part of 1,3,4,6-tetrakis(2-cyanoethyl)glycoluril.

The solvent used in the second process is not particularly limited, if it does not inhibit the reaction and, for example, the solvent identical with the solvent used in the reaction of the dicarbonyl compound (a) with the urea derivative (b) may be used.

The hydrolysis reaction of the 1,3,4,6-tetrakis(2-cyanoethyl)-glycoluril is normally carried out at a temperature in the range of 0° C. to 150° C., and preferably at a temperature in the range of room temperature to 100° C. Although the reaction time varies according to the reaction temperature, it is normally in the range of 1 to 36 hours, and preferably in the range of 1 to 16 hours.

After the hydrolysis reaction of the 1,3,4,6-tetrakis(2-cyanoethyl)-glycoluril for example by means of an operation such as extraction, desired 1,3,4,6-tetrakis(2-carboxyethyl) glycoluril can be obtained from the reaction mixture obtained. The desired 1,3,4,6-tetrakis(2-carboxyethyl)-glycoluril may be purified additionally, as needed, for example, by washing with a solvent such as water or by treatment with activated carbon.

The 1,3,4,6-tetrakis(carboxyalkyl)glycoluril according to the invention has four carboxyl groups in the molecule, as described above, and is thus useful, for example, as a crosslinking agent for epoxy resins.

The epoxy resin composition according to the invention contains the 1,3,4,6-tetrakis(carboxyalkyl)glycoluril represented by the general formula (A) as a crosslinking agent and additionally an amine as a curing agent.

The epoxy resin composition comprising a 1,3,4,6-tetrakis-(carboxyalkyl)glycoluril as crosslinking agent and an amine as a curing agent according to the invention gives a cured epoxy resin product higher in crosslinking density than those obtained with a known epoxy resin composition and thus, a cured epoxy resin product superior, for example, in hardness, heat resistance, moisture resistance and others.

The epoxy resin in the present invention refers to an epoxy compound having averagely two or more epoxy groups in the molecule. Examples of the epoxy resins include, as is well known, polyglycidyl ethers obtained by reaction of a polyvalent phenol such as bisphenol A, bisphenol F, bisphenol AD, catechol and resorcinol with epichlorohydrin, or obtained by reaction of a polyvalent alcohol such as glycerol or polyethylene glycol with epichlorohydrin; glycidyl ether esters obtained by reaction of a hydroxycarboxylic acid such as p-hydroxybenzoic acid or β-hydroxynaphthoic acid with epichlorohydrin; polyglycidyl esters obtained by reaction of a polycarboxylic acid such as phthalic acid or terephthalic acid with epichlorohydrin; epoxidized phenolic novolak resins, epoxidized cresol novolak resins, epoxidized polyolefins, cyclic aliphatic epoxy resins, urethane-modified epoxy resins and the like. However in the present invention, the epoxy resin is not limited to the examples above.

As conventionally known, the amine as a curing agent in the epoxy resin composition according to the invention is a compound that has one or more active hydrogens that bind to epoxy group by addition reaction and at least one amino group selected from primary, secondary, and tertiary amino groups in the molecule. Examples of the amine as a curing agent include aliphatic amines such as diethylenetriamine, triethylenetetramine, n-propylamine, 2-hydroxyethylaminopropylamine, cyclohexylamine and 4,4'-diaminodicyclohexylmethane; aromatic amines such as 4,4'-diaminodiphenylmethane and 2-methylaniline; nitrogen-containing heterocyclic compounds such as 2-ethyl-4-methylimidazole, 2-methylimidazole, 2-ethyl-4-methylimidazoline, 2,4-dimethylimidazoline, piperidine and piperazine; and the like. However, the amine-based curing agent in the present invention is not limited to the examples above.

The epoxy resin composition according to the invention may comprise additionally, as needed, various additives such as fillers, diluents, solvents, pigments, flexibilizers, coupling agents and antioxidants.

EXAMPLES

Hereinafter, the invention will be described with reference to Examples, but it should be understood that the invention is not particularly restricted by these Examples.

In the Examples below, N,N'-carbonylbis(glycine methyl) used was prepared according to the method described in Synlett., 7, pp. 1104 to 1106 (2010).

The aqueous 40% glyoxal solution, glycoluril and acrylonitrile used were all products of Tokyo Kasei Kogyo Co., Ltd. and the DBU used was a product of Wako Pure Chemical Industries, Ltd.

Example 1

Synthesis of
1,3,4,6-tetrakis(carboxylmethyl)glycoluril

N,N'-Carbonylbis(glycine methyl) (2.04 g, 10.0 mmol), aqueous 40% glyoxal solution (726 mg, 5.0 mmol), acetic acid (10 mL) and sulfuric acid (49 mg, 0.5 mmol) were placed in a 100 mL flask equipped with a thermometer.

The mixture obtained was stirred overnight at 110° C. and then cooled to room temperature; acetone (50 mL) was added thereto; the precipitated crystal was collected by filtration and dried, to give white crystals of 1,3,4,6-tetrakis(carboxylmethyl)glycoluril (1.26 g, yield: 67%).

The 1,3,4,6-tetrakis(carboxylmethyl)glycoluril obtained had a melting point of 223° C. to 239° C. The IR spectrum is shown in FIG. 1. The δ values of the $^1$H-NMR spectrum (d6-DMSO) were as follows:

12.8 (br, 4H), 5.52 (s, 2H), 4.05 (d, 4H), 3.85 (d, 4H)

Example 2

Synthesis of 1,3,4,6-tetrakis(2-cyanoethyl)glycoluril

Glycoluril (13.54 g, 95.3 mmol), acrylonitrile (35.38 g, 666.8 mmol), DBU (0.58 g, 3.8 mmol) and water (54 mL) were placed in a 200 mL autoclave container equipped with a thermometer.

The mixture obtained was stirred at 120° C. for 5 hours and then cooled to room temperature. The precipitated crystals were collected by filtration and recrystallized from a mixed solvent of acetone (50 mL)/water (10 mL), to give white crystals of 1,3,4,6-tetrakis(2-cyanoethyl)glycoluril (20.75 g, yield: 61%).

Figure 2:
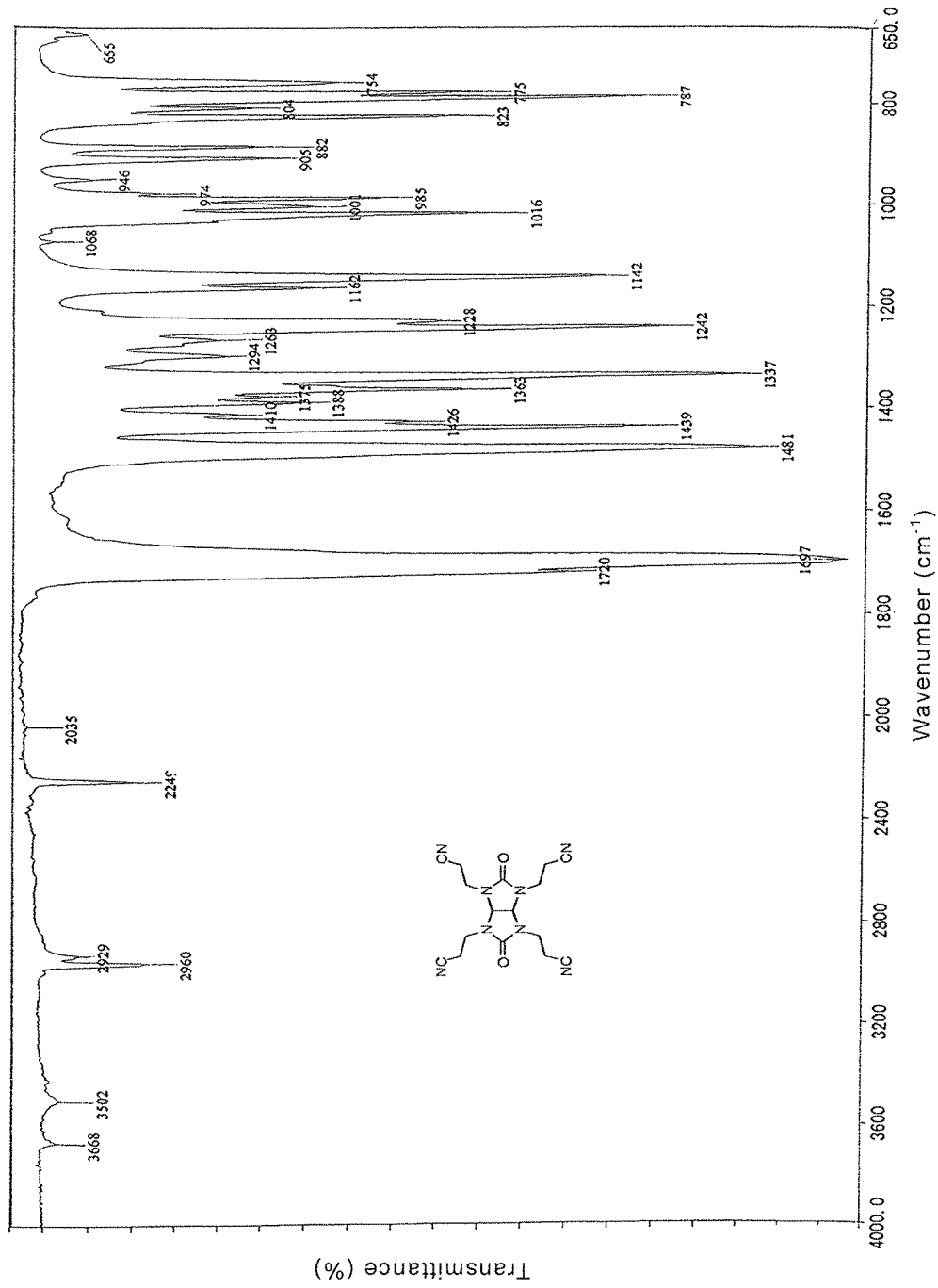
FIG. 2 shows an IR spectrum of 1,3,4,6-tetrakis(2-cyanoethyl)-glycoluril.

The 1,3,4,6-tetrakis(2-cyanoethyl)glycoluril obtained had a melting point of 139° C. to 141° C. The IR spectrum is shown in FIG. 2. The δ values of the $^1$H-NMR spectrum (d6-DMSO) were as follows:

5.50 (s, 2H), 3.64-3.71 (m, 4H), 3.44-3.51 (m, 4H), 2.79 (t, 8H)

Synthesis of
1,3,4,6-tetrakis(2-carboxylethyl)glycoluril 1,3,4,6-Tetrakis(2-cyanoethyl)glycoluril (10.00 g, 28.2 mmol) and conc. hydrochloric acid (20 mL) were placed in a 100 mL flask equipped with a thermometer.

The mixture obtained was stirred at 110° C. for 2 hours and concentrated under reduced pressure. Acetone (40 mL) was added to the concentrate obtained. Insoluble matters were removed by filtration and the filtrate was stirred for 1 hour, as cooled on ice. The precipitated crystals were collected by filtration and dried, to give white crystals of 1,3,4,6-tetrakis(2-carboxylethyl)glycoluril (4.62 g, yield: 38%).

Figure 3:
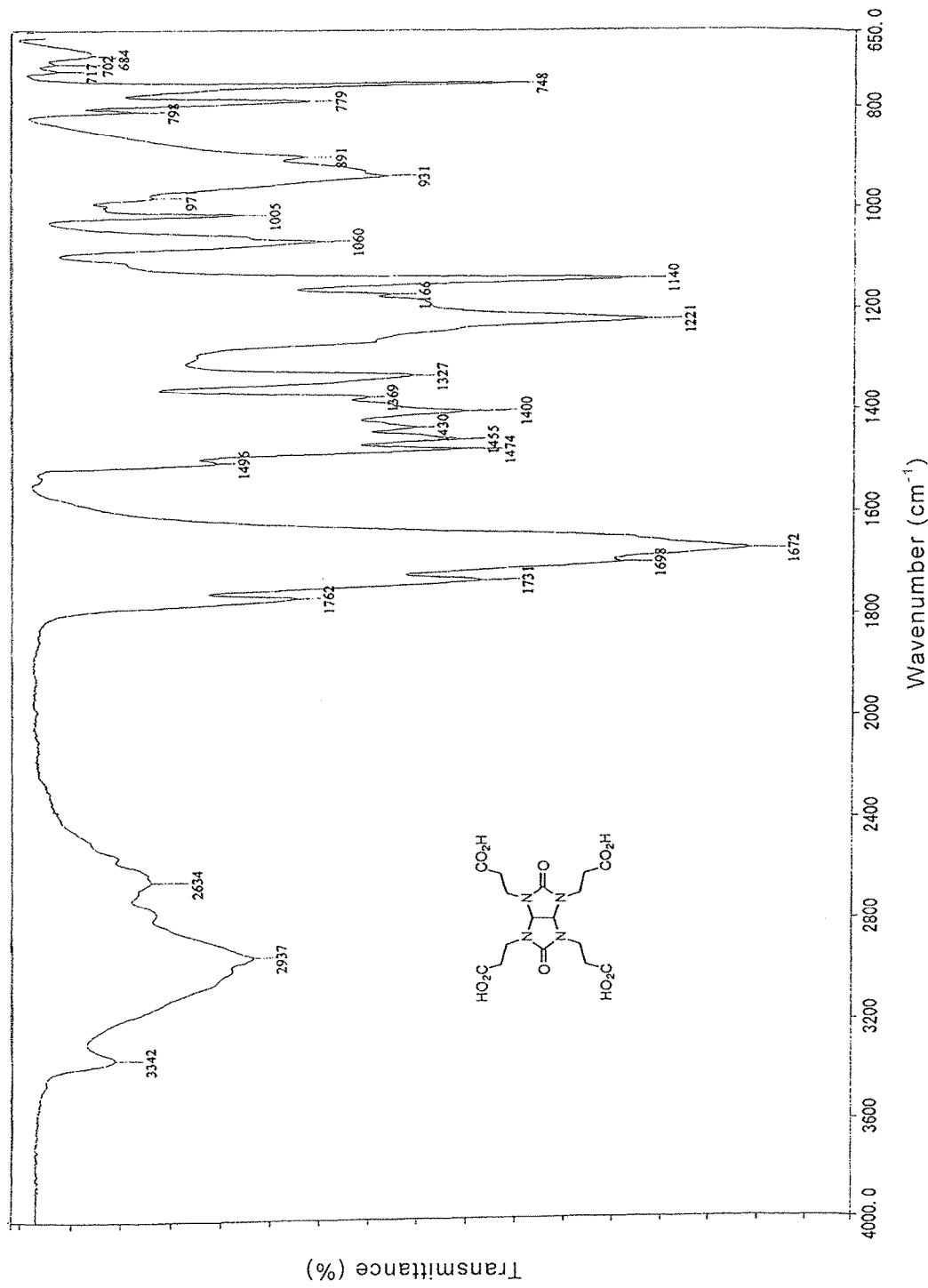
FIG. 3 shows an IR spectrum of 1,3,4,6-tetrakis(2-carboxyethyl)-glycoluril.

The 1,3,4,6-tetrakis(2-carboxylethyl)glycoluril obtained had a melting point of 115° C. to 121° C. The IR spectrum is shown in FIG. 3. The δ value of the $^1$H-NMR spectrum (D20) were as follows:

3.99 (s, 2H), 3.88 (t, 2H), 3.66 (t, 2H), 3.57 (t, 2H), 3.27 (t, 2H), 2.64 (t, 2H), 2.58 (t, 4H), 2.05 (t, 2H)

(2) A Polyester Resin Composition

The polyester resin composition according to the invention comprises:

(a) a polyester resin obtained by polycondensation reaction of the 1,3,4,6-tetrakis(carboxyalkyl)glycoluril represented by the general formula (A) and a glycol and (b) a β-hydroxyalkylamide as a curing agent.

According to the invention, the 1,3,4,6-tetrakis(carboxyalkyl)-glycoluril represented by the general formula (A) is used as a carboxylic acid component, i.e., a raw material for the polyester resin.

Concrete examples of the 1,3,4,6-tetrakis(carboxyalkyl) glycoluril include:

1,3,4,6-tetrakis(carboxylmethyl)glycoluril,
1,3,4,6-tetrakis(2-carboxylethyl)glycoluril,
1,3,4,6-tetrakis(carboxylmethyl)-3a-methylglycoluril,
1,3,4,6-tetrakis(2-carboxylethyl)-3a-methylglycoluril,
1,3,4,6-tetrakis(carboxylmethyl)-3a,6a-dimethylglycoluril,
1,3,4,6-tetrakis(2-carboxylethyl)-3a,6a-dimethylglycoluril
and the like.

In the invention, in addition to the 1,3,4,6-tetrakis(carboxyalkyl)-glycoluril, there may be used a carboxylic acid, for example, an aromatic dicarboxylic acid such as isophthalic acid, terephthalic acid, 5-sulfoisophthalic acid sodium salt, phthalic anhydride or naphthalenedicarboxylic acid; an aliphatic dicarboxylic acid such as adipic acid, sebacic acid, or dodecanedicarboxylic acid; a trivalent or higher carboxylic acid such as trimellitic acid or pyromellitic acid; an ester-forming derivative of these acids; or an oxycarboxylic acid such as 4-hydroxybenzoic acid or ε-caprolactone in the range that does not impair the advantageous effects of the invention.

Examples of the glycols in the invention include aliphatic diols such as neopentylglycol, ethylene glycol, diethylene glycol, propylene glycol, 1,4-butanediol and 1,6-hexanediol; alicyclic glycols such as 1,4-cyclohexanedimethanol and 1,4-cyclohexanediol; trivalent or higher alcohols such as trimethylolpropane, pentaerythritol and glycerol; and aromatic glycols such as bisphenol A ethylene oxide adducts and bisphenol S ethylene oxide adducts.

In the invention, the total amount (total content) of the 1,3,4,6-tetrakis(carboxyalkyl)glycoluril and the glycol should be 80 to 100 mol % of the all components. When the total content is less than 80 mol %, the coated film obtained shows insufficient weather resistance.

The acid value of the polyester resin according to the invention is preferably 20 to 50 mg-KOH/g, and more preferably 25 to 40 mg-KOH/g.

When the polyester resin has an acid value smaller than 20 mg-KOH/g, the resin has an excessively high molecular weight leading to reduction of fluidity, reduction of the smoothness of the coated film and deterioration in substrate adhesiveness. On the other hand, when it has an acid value larger than 50 mg-KOH/g, if it is blended as a raw material for paints, curing reaction with the curing agent is accelerated excessively, leading to deterioration in smoothness of the coated film and also to deterioration in adhesiveness to substrate.

The polyester resin according to the invention preferably has a melt viscosity of 100 to 800 dPa·s at 160° C., and more preferably of 150 to 700 dPa·s. When the polyester resin has a melt viscosity smaller than 100 dPa·s at 160° C., it shows excessively low melt viscosity, making the coated film drip. On the other hand, when it has a melt viscosity of more than 800 dPa·s, the coated film shows reduced smoothness and impaired substrate adhesiveness.

The polyester resin according to the invention is prepared by using the 1,3,4,6-tetrakis(carboxyalkyl)glycoluril and the glycol (including its ester-forming derivative) as raw materials, subjecting the raw materials to esterification or ester-exchange reaction at a temperature of 200° C. to 280° C., and then to polycondensation reaction under reduced pressure of 5 hPa or less at a temperature of 200° C. to 300° C., and preferably 230° C. to 290° C.

As needed, there may be added a process of depolymerization at a reaction temperature of 230° C. to 290° C., and preferably 250 to 280° C. for a period of 2 to 5 hours, preferably 2.5 to 4 hours in the presence of the 1,3,4,6-tetrakis(carboxyalkyl)glycoluril and/or an aromatic tricarboxylic acid.

When the depolymerization temperature is lower than 230° C., the depolymerizing agent does not react sufficiently, giving a high-polymerization-degree polymer, leading to reduction of the smoothness of the resulting coated film. Alternatively, when the depolymerization temperature is higher than 290° C., thermal decomposition of the polymer proceeds. Even at a predetermined temperature, if the depolymerization period is less than 2 hours, all the depolymerizing agent does not react completely, giving a coated film with reduced smoothness and reduced substrate adhesiveness. When the depolymerization period is more than 5 hours, the heat history is elongated and thermal decomposition of the polymer proceeds. In the esterification, ester-exchange and polycondensation reactions, known reaction catalysts may be used.

The resin composition for powder paints according to the invention gives a coated film with further improved properties when a hydroxyalkyl-amide is used as a curing agent in the polyester resin according to the invention.

The curing agent is not particularly limited in kind and examples thereof include "Primid XL-552" produced by EMS. The amount of the curing agent used is preferably in the range of 0.7 to 1.2 equivalences, and more preferably in the range of 0.9 to 1 equivalences with respect to the acid value of the polyester resin.

The resin composition for powder paints according to the invention is prepared by blending a mixture of the raw materials, and as needed, together with a known levelling agent and other additives such as titanium dioxide, sedimentary barium sulfate and pigments (such as carbon black) in the molten state with a kneader or roll at 70° C. to 140° C.

A coated film superior in smoothness and substrate adhesiveness is prepared by applying the resin composition for powder paints according to the invention on a substrate and baking it normally at a temperature of 150° C. to 190° C. for 15 to 25 minutes.

The polyester resin according to the invention has a low acid value, shows relatively slow curing reaction and has low melt viscosity. Thus, if used as a raw material for powder paints, it gives a cured product superior in smoothness. Further, as it has a high copolymerization ratio of the 1,3,4,6-tetrakis(carboxyalkyl)glycoluril to glycol, it provides a paint that gives a coated film superior in weather resistance.

EXAMPLES

Hereinafter, the invention will be described specifically with reference to Examples and Comparative Examples, but the invention is not limited thereto. In the Examples and Comparative Examples, the properties of the polyester resins, the resin compositions for powder paints and the coated films were determined and evaluated according to the methods described below:

(1) Acid Value

A polyester resin (0.5 g) was dissolved in a mixed solvent of dioxane/distilled water (10/1 by weight, 50 ml), and the acid value was determined after refluxing under heat by titrating the solution with $0.1 \times 10^3$ mol/m$^3$ potassium hydroxide methanol solution.

(2) Melt Viscosity

The melt viscosity was determined using a Brookfield melt viscometer (VISCOMETER DV-1 manufactured by Brookfield AMETEK Inc.) under the condition of a sample amount of 15 g and a temperature of 150° C.

(3) Smoothness

The smoothness of a coated film was evaluated by visual observation according to the following criteria:

○: the coated film is less irregular and superior in smoothness.

x: the coated film is significantly irregular.

(4) Adhesiveness

According to JIS K5400, a coated substrate carrying a coated film was immersed in boiling water for 2 hours and then dried in air at room temperature for 24 hours. Subsequently, checkerboard-like squares were engraved on the coated film with a cutter knife; a peeling test using an adhesive tape was carried out, and the result was examined by visual observation and evaluated according to the following criteria:

○: no exfoliation of the coated film observed.

x: exfoliation of coated film observed locally or entirely on the surface.

(5) Accelerated Weather Resistance

According to JIS K5400, the gloss retention rate (%) of a coated film after irradiation for 500 hours was determined using WEL-6-XS-HC-B-EC Sunshine Weather Meter (manufactured by Suga Test Instrument Co.). A gloss retention rate of 80% or more was considered satisfactory.

Example 1

1,3,4,6-Tetrakis(2-carboxyethyl)glycoluril (53.5 mole parts) and neopentylglycol (47.6 mole parts) were placed in an esterification reaction tank and subjected to esterification reaction at a pressure of 0.3 MPaG and a temperature of 260° C. for 4 hours.

The esterification product obtained was supplied into a polycondensation reaction tank; antimony trioxide was added in an amount of $4.0 \times 10^{-4}$ mole/1 mole of carboxylic acid component, and tetrabutyl titanate in an amount of $0.1 \times 10^{-4}$ mole/1 mole of carboxylic acid component; and the mixture was subjected to polycondensation reaction at a reduced pressure of 0.5 hPa and a temperature of 280° C. for 4 hours to give a polyester resin having the properties shown in Table 1.

A butyl polyacrylate-based levelling agent ("AKRONAL 4F," produced by BASF), benzoin and a rutile titanium dioxide pigment ("TIPAQUE CR-90," produced by Ishihara Sangyo Kaisha, Ltd.) were added to the mixture obtained by blending a hydroxyalkylamide as a curing agent ("Primid XL-552," produced by EMS) to the polyester resin obtained respectively in the amounts (parts by mass) shown in Table 1; the mixture was dry-blended with a Henschel Mixer ("FM10B" manufactured by Mitsui Miike Machinery Co., Ltd.) and melt-kneaded from a co-kneader ("PR-46" manufactured by BUSS)) at 100° C.; and the extrudate was cooled, pulverized, and classified with a 140 mesh (106 μm) wire mesh, to give a resin composition for powder paints.

The resin composition for powder paints obtained was coated electrostatically on a zinc phosphate-treated steel plate to a film thickness of 50 to 60 μm and baked at a temperature of 160° C. for 20 minutes. The properties of the coated film obtained were evaluated and the results are summarized in Table 1.

Examples 2 and 3 and Comparative Examples 1 and 2

The polyester resins and the resin compositions for powder paints described in Table 1 were prepared and the properties thereof and also of the coated films were determined and evaluated in a manner similar to Example 1.

The measurement and evaluation results obtained are summarized in Table 1.

TABLE 1

|  | Examples | | | Comparative Examples | |
|---|---|---|---|---|---|
|  | 1 | 2 | 3 | 1 | 2 |
| Composition of polyester resin (mole parts) | | | | | |
| 1,3,4,6-Tetrakis(2-carboxyethyl)glycoluril | 53.5 | 33.9 | 33.9 | — | — |
| Isophthalic acid | — | 19.6 | — | 53.5 | — |
| Terephthalic acid | — | — | 19.6 | — | 53.5 |
| Neopentylglycol | 47.6 | 47.6 | 47.6 | 47.6 | 47.6 |
| Evaluation | | | | | |
| Acid value (mg-KOH/g) | 30 | 33 | 36 | 52 | 44 |
| Melt viscosity (dPa · s) | 240 | 360 | 270 | 190 | 160 |
| Composition of resin composition for powder paint (parts by mass) | | | | | |
| Polyester resin | 95.7 | 95.3 | 94.9 | 92.8 | 97.4 |
| Hydroxyalkylamide as a curing agent | 4.3 | 4.7 | 5.1 | 3.9 | 5.4 |
| Benzoin | 0.5 | 0.5 | 0.5 | 0.5 | 0.5 |
| Levelling agent | 1.0 | 1.0 | 1.0 | 1.0 | 1.0 |
| Titanium dioxide | 60 | 60 | 60 | 60 | 60 |
| Evaluation | | | | | |
| Smoothness of coated film | ○ | ○ | ○ | X | X |
| Accelerated weather resistance | 100 | 100 | 96 | 68 | 64 |
| Substrate adhesiveness | ○ | ○ | ○ | X | X |

Second Invention (1) A New Lycidylglycoluril and an Epoxy Resin Composition Comprising the Same The new glycidylglycoluril according to the invention is represented by the general formula (B):

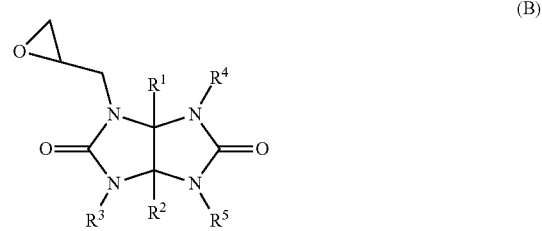

(B)

wherein $R^1$ and $R^2$ each independently represents a hydrogen atom, a lower alkyl or a phenyl group; and $R^3$, $R^4$ and $R^5$ each independently represents a hydrogen atom or a glycidyl group.

Thus, the invention provides the following glycidylglycolurils:

a monoglycidylglycoluril represented by the general formula (Ba):

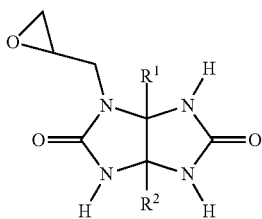
(Ba)

wherein R¹ and R² are the same as those described above;

a diglycidylglycoluril represented by the general formula (Bb):

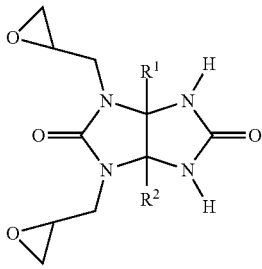
(Bb)

wherein R¹ and R² are the same as those described above;

a diglycidylglycoluril represented by the general formula (Bc):

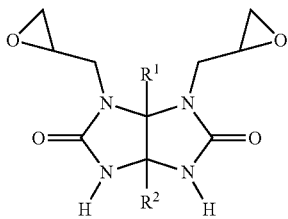
(Bc)

wherein R¹ and R² are the same as those described above;

a diglycidylglycoluril represented by the general formula (Bd):

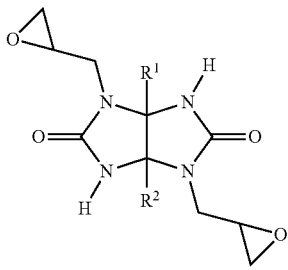
(Bd)

wherein R¹ and R² are the same as those described above;

a triglycidylglycoluril represented by the general formula (Be):

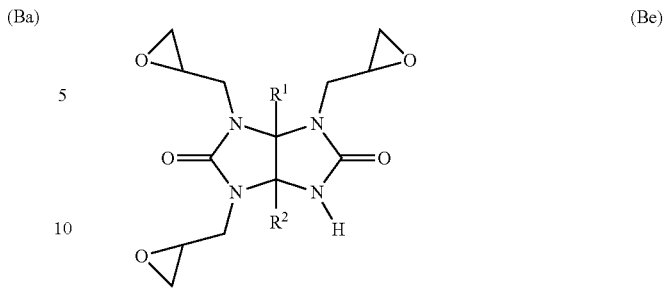
(Be)

wherein R¹ and R² are the same as those described above; and a tetraglycidylglycoluril represented by the general formula (Bf):

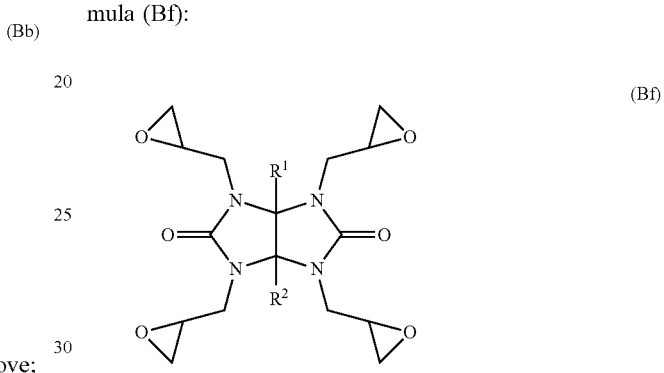
(Bf)

wherein R¹ and R² are the same as those described above.

When R¹ or R² in the glycidylglycolurils represented by the general formulae (B), and (Ba) to (Bf) above is a lower alkyl group, the lower alkyl group is usually an alkyl group having 1 to 5 carbon atoms, preferably having 1 to 3 carbon atoms, and most preferably having 1 carbon atom and thus, the most preferable lower alkyl group is a methyl group.

Accordingly, preferred concrete examples of the glycidylglycolurils according to the invention include:
1-glycidylglycoluril,
1,3-diglycidylglycoluril,
1,4-diglycidylglycoluril,
1,6-diglycidylglycoluril,
1,3,4-triglycidylglycoluril,
1,3,4,6-tetraglycidylglycoluril,
1-glycidyl-3a-methylglycoluril,
1-glycidyl-6a-methyl-glycoluril,
1,3-diglycidyl-3a-methylglycoluril,
1,4-diglycidyl-3a-methylglycoluril,
1,6-diglycidyl-3a-methylglycoluril,
1,3,4-triglycidyl-3a-methylglycoluril,
1,3,4-triglycidyl-6a-methylglycoluril,
1,3,4,6-tetraglycidyl-3a-methylglycoluril,
1-glycidyl-3a,6a-dimethylglycoluril,
1,3-diglycidyl-3a,6a-dimethylglycoluril,
1,4-diglycidyl-3a,6a-dimethylglycoluril,
1,6-diglycidyl-3a,6a-dimethylglycoluril,
1,3,4-triglycidyl-3a,6a-dimethylglycoluril,
1,3,4,6-tetraglycidyl-3a,6a-dimethylglycoluril,
1-glycidyl-3a,6a-diphenylglycoluril,
1,3-diglycidyl-3a,6a-diphenylglycoluril,
1,4-diglycidyl-3a,6a-diphenylglycoluril,
1,6-diglycidyl-3a,6a-diphenylglycoluril,
1,3,4-triglycidyl-3a,6a-diphenylglycoluril,
1,3,4,6-tetraglycidyl-3a,6a-diphenylglycoluril and the like.

The glycidylglycoluril according to the invention represented by the general formula (B) above is obtained by oxidizing and epoxidizing the carbon-carbon double bonds in an allylglycoluril represented by the general formula (a) by action of an oxidizing agent on the allylglycoluril.

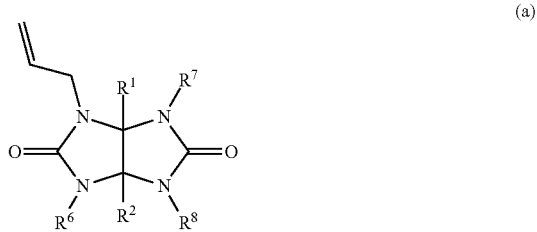

(a)

wherein $R^1$ and $R^2$ each independently represents a hydrogen atom, a lower alkyl or a phenyl group; and $R^6$, $R^7$ and $R^8$ each independently represents a hydrogen atom or a glycidyl group.

Generally, the methods of oxidizing and epoxidizing carbon-carbon double bonds have been well known and, in the present invention, such a method may be used. There may be mentioned as such methods, for example, a method in which a peracid such as Oxone reagent, peracetic acid or meta-chloroperbenzoic acid is used, or a method in which hydrogen peroxide is used in the presence of a catalyst sodium tungstate.

When a peracid is used as the oxidizing agent, the peracid is used preferably in an amount of 1.0 to 5.0 equivalences with respect to the allyl groups present in the allylglycoluril.

The reaction solvent is not particularly limited, if it does not inhibit the reaction when used, and examples thereof include water, alcohols such as methanol, ethanol and isopropyl alcohol; aliphatic hydrocarbons such as hexane and heptane; ketones such as acetone and 2-butanone; esters such as ethyl acetate and butyl acetate; aromatic hydrocarbons such as benzene, toluene and xylene; halogenated hydrocarbons such as methylene chloride, chloroform, carbon tetrachloride, chlorotrifluoromethane, dichloroethane, chlorobenzene and dichlorobenzene; ethers such as diethyl ether, diisopropyl ether, tetrahydrofuran, dioxane, dimethoxyethane and diethylene glycol dimethyl ether; amides such as formamide, N,N-dimethylformamide, N,N-dimethylacetamide, N-methyl-2-pyrrolidone, N-methylpyrrolidinone and hexamethylphosphorotriamide; sulfoxides such as dimethylsulfoxide and the like. These reaction solvent are used alone or in combination of two or more in a suitable amount.

The reaction temperature when the allylglycoluril is oxidized with the peracid is normally in the range of −10° C. to 150° C., and preferably in the range of 0° C. to 100° C. The reaction time varies according to the reaction temperature, but is normally in the range of 1 to 24 hours, and preferably in the range of 1 to 6 hours.

The desired glycidylglycoluril is obtained, for example, by extracting it from the reaction mixture obtained after the reaction or by crystallizing it from a suitable solvent and then collecting it by filtration.

When the allylglycoluril is oxidized with hydrogen peroxide in the presence of a catalyst sodium tungstate, hydrogen peroxide is used in an amount of 1.0 to 5.0 equivalents with respect to the allyl group present in the allylglycoluril. Alternatively, sodium tungstate is used preferably in an amount of 0.001 to 0.5 equivalents with respect to the allyl group present in the allylglycoluril.

The reaction solvent, if used, is not particularly limited, if it does not inhibit the reaction and, for example, the reaction solvent identical with those employed in the oxidation reaction using the peracid described above may be used.

Similarly to the oxidation reaction using the peracid described above, the reaction temperature is normally in the range of −10° C. to 150° C., and preferably in the range of 0° C. to 100° C. The reaction time varies according to the reaction temperature, but is normally in the range of 1 to 24 hours, and preferably in the range of 1 to 6 hours.

Similarly to the case of the oxidation reaction using the peracid described above, the desired glycidylglycoluril can be obtained after reaction by extracting it from the reaction mixture obtained or by crystallizing it from a suitable solvent and then collecting it by filtration.

The desired glycidylglycoluril thus obtained is purified, as needed, for example, by washing with a solvent such as water or by treatment with activated carbon, silica gel chromatography or the like.

Among the glycidylglycolurils according to the invention, those having one glycidyl group in the molecule are useful, for example, as a synthetic intermediate for oxygen-containing compounds and as a diluent for epoxy resins. Among the glycidylglycolurils according to the invention, those having two or more glycidyl groups in the molecule are useful, for example, as a crosslinking agent for epoxy resins.

Examples of the epoxy resins mentioned above include bisphenol A-type epoxy resins, bisphenol F-type epoxy resins, novolak-type epoxy resins such as phenolic novolak-type epoxy resins and cresol novolak-type epoxy resins, alicyclic epoxy resins, cyclic alicyclic epoxy resins such as 3',4'-epoxycyclohexylmethyl-3,4-epoxycyclohexanecarboxylate; nitrogen-containing cyclic epoxy resins such as triglycidyl isocyanurate, monoallyl diglycidyl isocyanurate, diallyl monoglycidyl isocyanurate and hydantoin-type epoxy resins; hydrogenated bisphenol A-type epoxy resins, aliphatic epoxy resins, glycidyl ether-type epoxy resins, bisphenol S-type epoxy resins, biphenyl-type epoxy resins, dicyclocyclic epoxy resins, naphthalene-type epoxy resins, halogenated epoxy resins, epoxy-modified organopolysiloxane compounds obtained by hydrosilylation addition reaction between an organic compound having a carbon-carbon double bond and a glycidyl group and a silicon compound having a SiH group (for example, epoxy-modified organopolysiloxane compounds disclosed in JP-A Nos. 2004-99751 and 2006-282988) and the like.

By blending the glycidylglycoluril according to the invention with a curing agent and, as needed, a curing accelerator with the epoxy resin described above, an epoxy resin composition is prepared.

In such an epoxy resin composition according to the invention, the glycidylglycoluril according to the invention is normally used in an amount of 0.1 to 150 parts by mass, and preferably in an amount of 10 to 100 parts by mass with respect to 100 parts by mass of the epoxy resin.

Examples of the curing agents include phenolic hydroxyl group-containing compounds, acid anhydrides, amines, mercaptan compounds such as mercaptopropionic esters and epoxy resin terminal mercapto compounds; organic phosphine compounds such as triphenylphosphine, diphenylnaphthylphosphine and diphenylethylphosphine; aromatic phosphonium salts, aromatic diazonium salts, aromatic iodonium salts, aromatic selenium salts and the like.

Examples of the phenolic hydroxyl group-containing compounds above include bisphenol A, bisphenol F, bisphenol S, tetramethylbisphenol A, tetramethylbisphenol F, tetramethylbisphenol S, tetrachlorobisphenol A, tetrabromobisphenol A, dihydroxynaphthalene, phenolic novolak resins, cresol novolak resins, bisphenol A novolak resins, brominated phenolic novolak resins, resorcinol and the like.

Examples of the acid anhydrides above include methyltetrahydrophthalic anhydride, methylhexahydrophthalic anhydride, hexahydrophthalic anhydride, 5-norbornene-2,3-dicarboxylic anhydride, trimellitic anhydride, nadic anhydride, himic anhydride, methylnadic anhydride, methyldicyclo[2,2,1]heptane-2,3-dicarboxylic anhydride, bicyclo[2,2,1]heptane-2,3-dicarboxylic anhydride, methylnorbornane-2,3-dicarboxylic anhydride and the like.

Examples of the amines include diethylenediamine, triethylenetetramine, hexamethylenediamine, dimer acid-modified ethylenediamines, 4,4'-diaminodiphenylsulfone, 4,4'-diaminodiphenol ether, 1,8-diazabicyclo[5.4.0]-7-undecene and imidazole compounds such as 2-methylimidazole, 2-ethyl-4-methylimidazole and 2-phenylimidazole.

In the epoxy resin composition according to the invention, the curing agent is normally used in an amount of 10 to 300 parts by mass, and preferably 100 to 200 parts by mass, with respect to 100 parts by mass of the epoxy resin.

Examples of the curing accelerators include amine compounds such as 1,8-diazabicyclo[5.4.0]-7-undecene, diethylenetriamine, triethylenetetramine, benzyldimethylamine, triethanolamine, dimethylaminoethanol and tris(dimethylaminomethyl)phenol; imidazole compounds such as 2-methylimidazole, 2-phenylimidazole, 2-phenyl-4-methylimidazole and 2-heptadecylimidazole; organic phosphine compounds such as tributylphosphine, methyldiphenylphosphine, triphenylphosphine, diphenylphosphine and phenylphosphine; phosphonium compounds such as tetrabutylphosphonium bromide and tetrabutylphosphonium diethylphosphorodithionate; tetraphenylboric acid salts such as tetraphenylphosphonium tetraphenylborate, 2-methyl-4-methylimidazole tetraphenylborate and N-methylmorpholine tetraphenylborate; aliphatic acid metal salts such as lead acetate, tin octanoate and cobalt hexanoate; and the like. It is known that some of these curing accelerators can also be used as the curing agent described above.

In the epoxy resin composition according to the invention, the curing accelerator is normally used in an amount of 0.01 to 2.0 parts by mass, preferably 0.1 to 0.5 parts by mass, with respect to 100 parts by mass of the epoxy resin.

The epoxy resin composition according to the invention may comprises, as needed, inorganic-fillers such as amorphous silica, crystalline silica, calcium carbonate, magnesium carbonate, alumina, magnesia, clay, talc, calcium silicate and titanium oxide; and/or various polymers such as phenol resins and unsaturated polyesters.

The epoxy resin composition according to the invention may further comprise various additives in addition to those described above. Examples of such additives include aliphatic polyols such as ethylene glycol and propylene glycol; carbon dioxide gas generation inhibitors such as aliphatic or aromatic carboxylic acid compounds and phenol compounds; flexibilizers such as polyalkylene glycols; antioxidants, plasticizers, lubricants, coupling agents such as silane-based coupling agents, surface finishing agents for inorganic filler, flame retardants, antistatic agents, colorants, levelling agents, ion-trapping agents, slidability improving agents, various rubbers, organic polymer beads, impact resistance-improving agents of inorganic fillers such as glass beads and glass fibers; thixotropic agents, surfactants, surface tension-reducing agents, antifoams, sedimentation inhibitors, light-diffusing agents, ultraviolet absorbents, release agents, fluorescent agents, conductive fillers and the like.

Such an epoxy resin composition is expected to be used as a paint for printed wiring boards and electronic parts, a sealer, an adhesive or a resist ink and also as a woodwork paint or a coating agent for protection of the surface of optical fibers, plastic products and cans.

EXAMPLES

Hereinafter, the present invention will be described with reference to Examples but it should be understood that the present invention is not particularly restricted by these Examples.

Comparative Example 1

Synthesis of 1,3-diallylglycoluril

Urea (3.00 g, 50.0 mmol) and aqueous 40% glyoxal solution (8.71 g, 60.0 mmol) were placed in a 100 mL flask equipped with a thermometer. Two drops of 40% aqueous sodium hydroxide solution was added to the mixture at room temperature and the mixture was stirred at 80° C. for 1 hour. The reaction mixture was then concentrated under reduced pressure. Diallylurea (7.00 g, 50.0 mmol), acetic acid (50 mL) and sulfuric acid (490 mg, 5.0 mmol) were added to the concentrate obtained and the mixture was stirred at 110° C. overnight. The reaction mixture was then cooled to room temperature; acetone (50 mL) was added thereto; viscous oil was separated from the reaction mixture and dried, to give 1,3-diallylglycoluril as a white viscous oil (yield: 39%).

Figure 4:
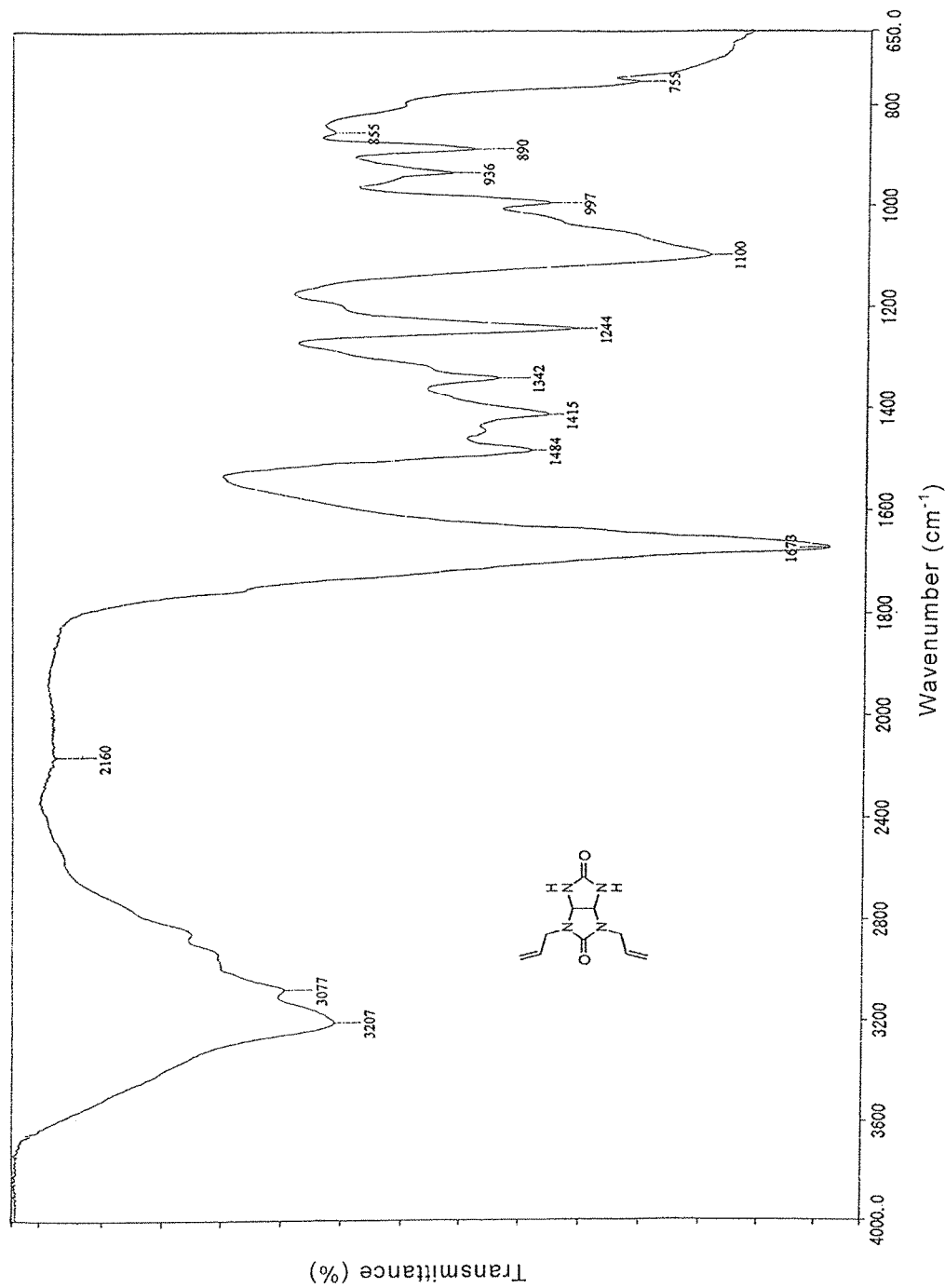
FIG. 4 shows an IR spectrum of 1,3-diallylglycoluril.

The IR spectrum of the 1,3-diallylglycoluril obtained is shown in FIG. 4. The δ values of $^1$H-NMR spectrum (d6-DMSO): 7.52 (s, 2H), 5.69-5.84 (m, 2H), 5.08-5.23 (m, 6H), 3.92^ (m, 2H), 3.52 (dd, 2H)

Comparative Example 2

Synthesis of 1,3,4,6-tetraallylglycoluril

It was prepared according to the method described in JP-A No. 11-171887.

Glycoluril (14.2 g, 100 mmol), sodium hydroxide (16.0 g, 400 mmol) and dimethylsulfoxide (140 mL) were mixed; after the mixture was stirred at 40° C. for 1 hour, allyl chloride (34.4 g, 400 mmol) was added dropwise to the mixture over 20 minutes at the same temperature. After the dropwise addition, the mixture was stirred under heat at 40° C. additionally for 2 hours for completion of the reaction.

The reaction mixture obtained was dried under reduced pressure to dryness. The solid obtained was subjected to extraction with ethyl acetate (400 mL) and water (400 mL). The ethyl acetate layer was washed with water (100 mL) and then with aqueous saturated sodium chloride solution (100 mL) and dried over anhydrous sodium sulfate. Ethyl acetate was removed by evaporation under reduced pressure, to give 1,3,4,6-tetraallylglycoluril (27.4 g) as a colorless oil (yield: 90%).

Comparative Example 3

Synthesis of 1,3,4,6-tetraallyl-3a,6a-dimethylglycoluril 3a,6a-dimethylglycoluril (17.0 g, 100 mmol), sodium hydroxide (16.0 g, 400 mmol) and dimethylsulfoxide (150 mL) were mixed; the mixture was stirred at 40° C. for 1 hour and allyl chloride (34.4 g, 400 mmol) was added dropwise to the mixture over 20 minutes at the same temperature. After the dropwise addition, the mixture was stirred at 40° C. additionally for 2 hours for completion of the reaction. The mixture was then post-treated similarly to Comparative Example 2, to give 1,3,4,6-tetraallyl-3a,6a-dimethylglycoluril (26.1 g) as crystal (yield: 79%).

Example 1

Synthesis of 1,3-diglycidylglycoluril 1,3-diallylglycoluril (1.11 g, 5.0 mmol) and dichloromethane (10 mL) were placed in a 100 mL flask equipped with a thermometer and a stirrer; m-chloroperbenzoic acid (purity: 65%, 2.92 g, 11.0 mmol) was added thereto under ice-cooling; and the mixture was heated to room temperature and stirred overnight.

10% aqueous sodium sulfite solution (20 mL) was added to the reaction mixture obtained; chloroform (20 mL) was added thereto; the mixture was agitated and then left still; and the organic layer generated was extracted and separated.

The extraction operation with chloroform was repeated twice additionally and the extracted solutions were combined and dried over sodium sulfate, followed by removing the volatile materials by distillation. The residue thus obtained was purified by silica gel chromatography (chloroform/methanol: 10/1 (by volume)), to give 1,3-diglycidylglycoluril 1.80 g as a white viscous oil (yield: 98%).

Figure 5:
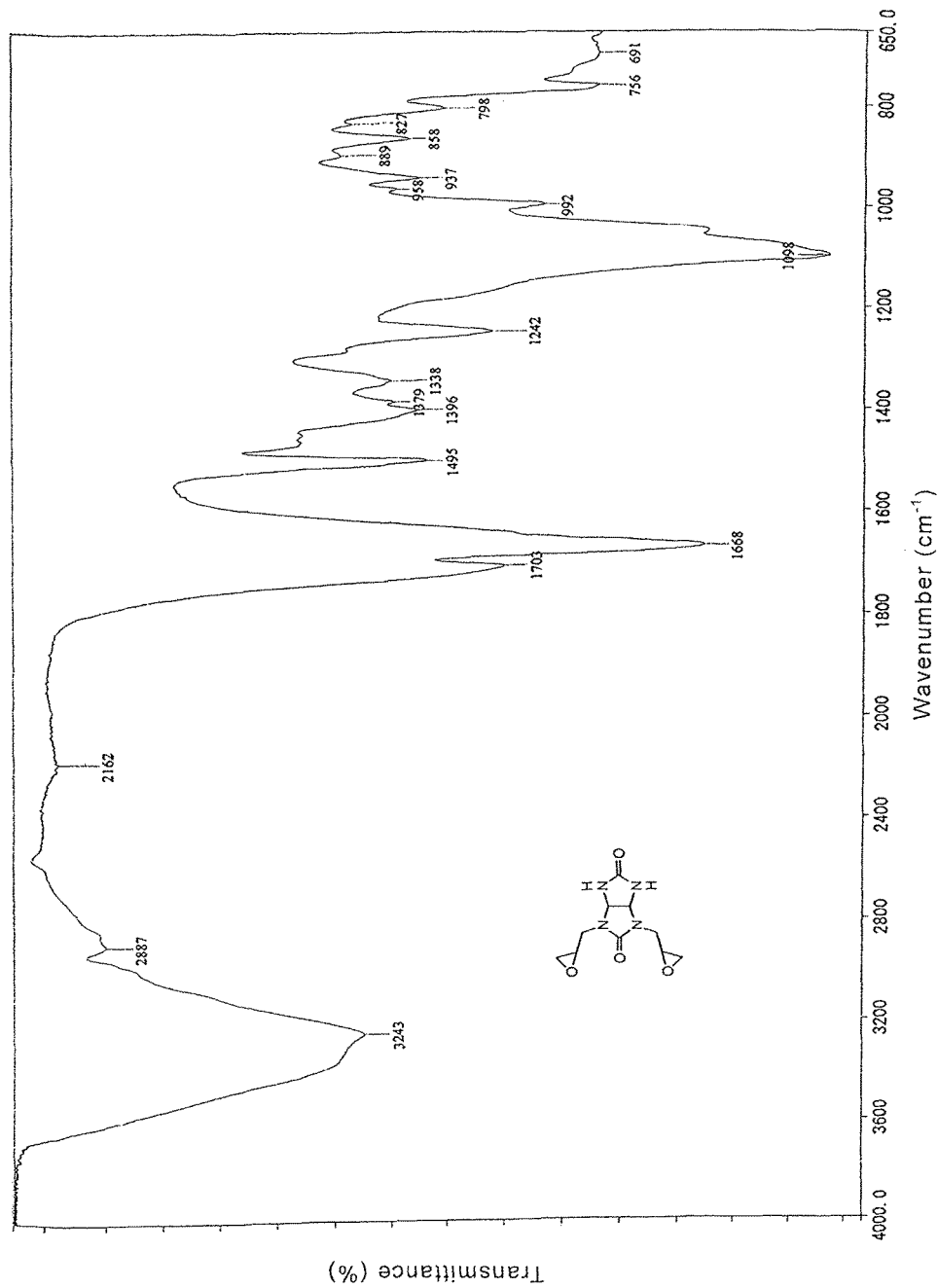
FIG. 5 shows an IR spectrum of 1,3-diglycidylglycoluril.

The IR spectrum of the 1,3-diglycidylglycoluril obtained is shown in FIG. 5. The δ values of the $^1$H-NMR spectrum (CDCl3) were as follows:

7.36 (br, 2H), 5.12-5.37 (m, 8H), 4.77-4.82 (m, 2H), 4.54-4.57 (m, 2H)

Example 2

Synthesis of 1,3,4,6-tetraglycidylglycoluril 1,3,4,6-tetraallylglycoluril (1.51 g, 5.0 mmol) and dichloromethane (10 mL) were placed in a 100 mL flask equipped with a thermometer and a stirrer; m-chloroperbenzoic acid (purity: 65%, 5.84 g, 22.0 mmol) was added thereto under ice-cooling, and the mixture was heated to room temperature and stirred overnight.

10% aqueous sodium sulfite solution (20 mL) was added to the reaction mixture obtained; chloroform (20 mL) was added thereto; the mixture was agitated and then left still; and the organic layer generated was extracted and separated.

The extraction operation with chloroform was repeated twice additionally and the extracted solutions were combined and dried over sodium sulfate, followed by removing the volatile materials by evaporation. The residue thus obtained was purified by silica gel chromatography (chloroform/methanol: 40/1 (by volume)), to give 1,3,4,6-tetraglycidyl-glycoluril 1.80 g as a colorless oil (yield: 98%).

Figure 6:
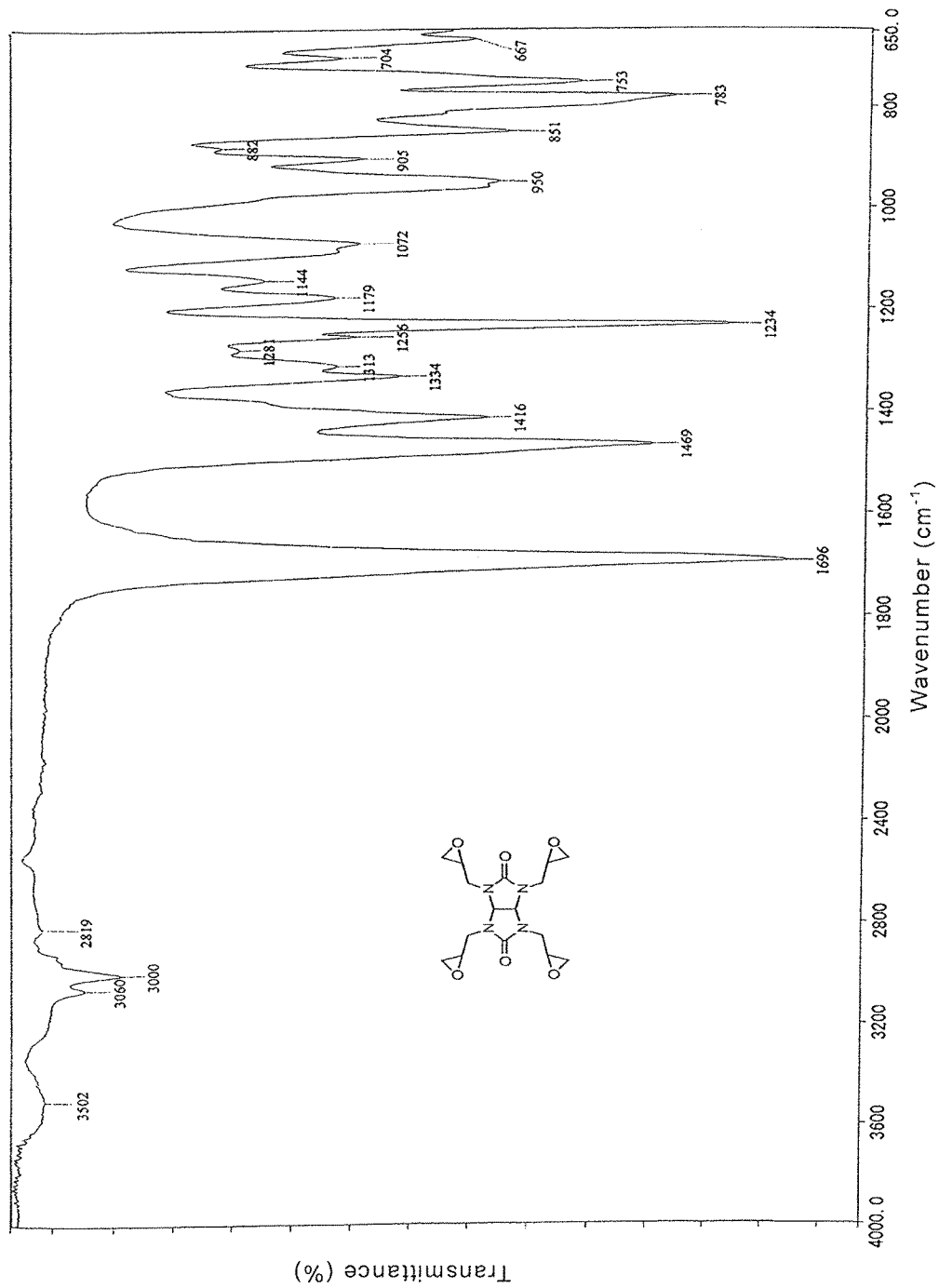
FIG. 6 shows an IR spectrum of 1,3,4,6-tetraglycidylglycoluril.

The IR spectrum of the 1,3,4,6-tetraglycidylglycoluril obtained is shown in FIG. 6. The δ values of the $^1$H-NMR spectrum (CDCl3) were as follows:

5.37-5.69 (m, 2H), 4.23-4.27 (m, 1H), 4.03-4.06 (m, 1H), 3.61-3.81 (m, 3H), 3.45-3.46 (m, 1H), 3.01-3.23 (m, 6H), 2.78-2.84 (m, 4H), 2.59-2.63 (m, 4H)

Example 3

Synthesis of 1,3,4,6-tetraglycidyl-3a,6a-dimethylglycoluril 1,3,4,6-tetraallyl-3a,6a-dimethylglycoluril (1.51 g, 5.0 mmol) and dichloromethane (10 mL) were placed in 100 mL flask equipped with a thermometer and a stirrer; m-chloroperbenzoic acid (purity: 65%, 5.84 g, 22.0 mmol) was added thereto under ice-cooling, and the mixture was heated to room temperature and stirred overnight.

10% aqueous sodium sulfite solution (20 mL) was added to the reaction mixture obtained; chloroform (20 mL) was added thereto; the mixture was agitated and then left still; and the organic layer generated was extracted and separated.

The extraction operation with chloroform was repeated twice additionally and the extracted solutions were combined and dried over sodium sulfate, followed by removing the volatile materials by distillation. The residue thus obtained was purified by silica gel chromatography (chloroform/methanol: 40/1 (by volume)), to give 1,3,4,6-tetraglycidyl-3a,6a-dimethylglycoluril 1.81 g as a colorless liquid (yield: 92%).

Figure 7:
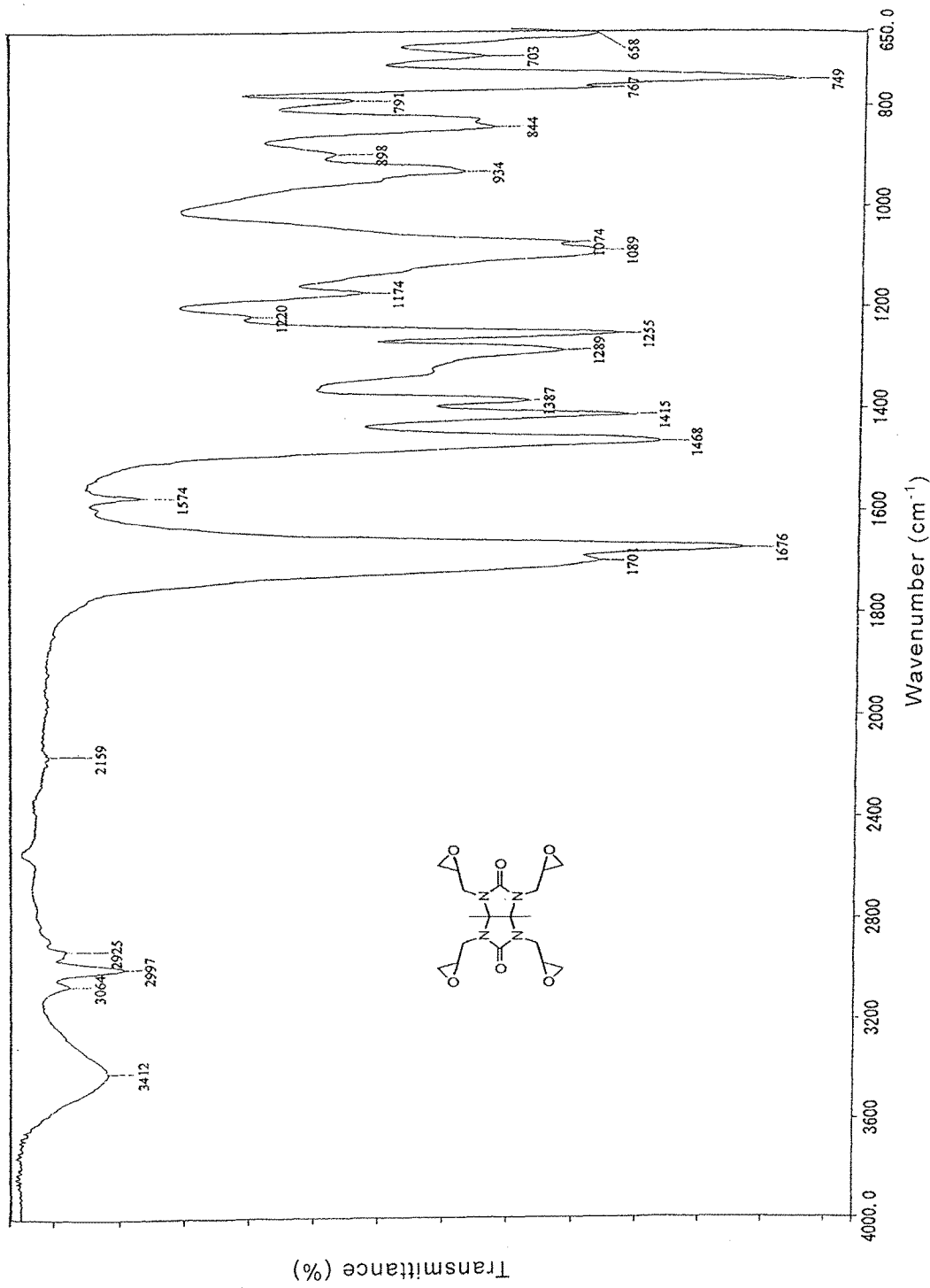
FIG. 7 shows an IR spectrum of 1,3,4,6-tetraglycidyl-3a, 6a-dimethylglycoluril.

The IR spectrum of 1,3,4,6-tetraglycidyl-3a,6a-dimethylglycoluril obtained is shown in FIG. 7. The δ values of the $^1$H-NMR spectrum (CDCl$_3$) were as follows:

3.40-4.37 (m, 8H), 3.03-3.18 (m, 3H), 2.78-2.85 (m, 3H), 2.55-2.62 (m, 3H), 2.55-2.62 (m, 3H), 1.45-1.70 (m, 9H)

Example 4

As shown in Table 2, a hydrogenated bisphenol A-type epoxy resin (YX8000 produced by Mitsubishi Chemical Corporation, abbreviated as YX8000 in Table 1, 80 parts by mass) was blended with a curing agent, 4-methylhexahydrophthalic anhydride/hexahydrophthalic anhydride (mixture at a weight ratio of 70/30, Rikacid MH-700 produced by New Japan Chemical Co., Ltd., abbreviated as MH-700 in Table 1, 120 parts by mass), a curing accelerator, tetra-n-butylphosphonium-o,o-diethylphosphorodithionate (HISHICOLIN PX-4ET produced by Nippon Chemical Industrial Co., Ltd., abbreviated as PX-4ET in Table 1, 0.5 part by mass) and a crosslinking agent 1,3,4,6-tetraglycidylglycoluril (abbreviated as TG-G in Table 1, 20 parts by mass) and the mixture was kneaded, to give an epoxy resin composition.

The epoxy resin composition was heated at a temperature of 120° C. for 6 hours to give a cured product. The glass transition point (Tg), bending modulus and bending strength of the cured product were determined to give the results shown in Table 2. Tg was determined by DSC according to JIS K7121. The bending modulus and the bending strength were determined according to JIS K7203.

Comparative Example 1

As shown in Table 2, a hydrogenated bisphenol A-type epoxy resin (YX8000 produced by Mitsubishi Chemical Corp., 100 parts by mass) was blended with a curing agent 4-methylhexahydrophthalic anhydride/hexahydrophthalic anhydride (70/30 mixture, Rikacid MH-700 produced by New Japan Chemical Co., Ltd., 80 parts by mass) and a curing accelerator, tetra-n-butylphosphonium-o,o-diethylphosphorodithionate (HISHICOLIN PX-4ET produced by Nippon Chemical Industrial Co., Ltd., 0.5 part by mass) and the mixture was kneaded to give an epoxy resin composition.

The epoxy resin composition was heated in the same manner as in Example 4 to give a cured product. The glass transition point (Tg), bending modulus and bending strength of the cured product were determined to give the results shown in Table 2.

Comparative Example 2

An epoxy resin composition was prepared in the same manner as in Example 4, except that the crosslinking agent, 1,3,4,6-tetraglycidyl-glycoluril (20 parts by mass) was replaced with triglycidyl isocyanuric acid (triglycidyl isocyanurate produced by Tokyo Kasei Kogyo Co., Ltd., abbreviated as TG-ICA in Table 2, 20 parts by mass).

The epoxy resin composition was heated in the same manner as in Example 4 to give a cured product. The glass transition point (Tg), bending modulus and bending strength of the cured product were determined, to give the results shown in Table 2.

TABLE 2

|  | Examples | Comparative Examples | |
| --- | --- | --- | --- |
|  | 4 | 1 | 2 |
| Composition of epoxy resin composition (parts by mass) | | | |
| TG-G | 20 | — | — |
| TG-ICA | — | — | 20 |
| YX8000 | 80 | 100 | 80 |
| MH-700 | 120 | 80 | 120 |
| PX-4ET | 0.5 | 0.5 | 0.5 |
| Properties of cured product | | | |
| Tg (° C.) | 141 | 110 | 128 |
| Bending modulus (Mpa) | 3056 | 2501 | 2815 |
| Bending strength (Mpa) | 120 | 104 | 112 |

As obvious from the results shown in Table 2, the epoxy resin compositions comprising the glycidylglycoluril according to the invention as a crosslinking agent show superior heat resistance and also superior mechanical strength, compared to the cured product from an epoxy resin composition containing no crosslinking agent (Comparative Example 1) and the cured product from an epoxy resin composition containing triglycidyl isocyanuric acid as the crosslinking agent (Comparative Example 2).

(2) An Epoxy Resin Composition for Use in Sealing of Optical Semiconductor Elements The epoxy resin composition for use in sealing of optical semiconductor elements according to the invention comprises an epoxy resin (1), wherein at least one component of the epoxy resin is the glycidylglycoluril represented by the general formula (B) above.

The epoxy resin composition for use in sealing of optical semiconductor elements according to the invention (hereinafter, referred to simply as resin composition) comprises the epoxy resin component (1) shown below as an essential component and may comprise additionally at least one component selected from the components (2) to (9) shown below.

Component (1): Epoxy Resin

The component (1) epoxy resin is the major component of the resin composition according to the invention. The component (1) comprises the glycidylglycoluril represented by the general formula (B) above as an essential component.

Concrete examples of the glycidylglycolurils represented by Chemical Formula (B) above include:
1-glycidylglycoluril,
1,3-diglycidylglycoluril,
1,4-diglycidylglycoluril,
1,6-diglycidylglycoluril,
1,3,4-triglycidylglycoluril,
1,3,4,6-tetraglycidylglycoluril,
1-glycidyl-3a-methyl-glycoluril,
1,3-diglycidyl-3a-methyl-glycoluril,
1,4-diglycidyl-3a-methyl-glycoluril,
1,6-diglycidyl-3a-methyl-glycoluril,
1,3,4-triglycidyl-3a-methyl-glycoluril,
1,3,4,6-tetraglycidyl-3a-methyl-glycoluril,
1-glycidyl-3a,6a-dimethyl-glycoluril,
1,3-diglycidyl-3a,6a-dimethyl-glycoluril,
1,4-diglycidyl-3a,6a-dimethyl-glycoluril,
1,6-diglycidyl-3a,6a-dimethyl-glycoluril,
1,3,4-triglycidyl-3a,6a-dimethyl-glycoluril,
1,3,4,6-tetraglycidyl-3a,6a-dimethyl-glycoluril,
1-glycidyl-3a,6a-diphenyl-glycoluril,
1,3-diglycidyl-3a,6a-diphenyl-glycoluril,
1,4-diglycidyl-3a,6a-diphenyl-glycoluril,
1,6-diglycidyl-3a,6a-diphenyl-glycoluril,
1,3,4-triglycidyl-3a,6a-diphenyl-glycoluril,
1,3,4,6-tetraglycidyl-3a,6a-diphenyl-glycoluril and the like.

The glycidylglycolurils represented by the general formula (B) above may be used alone or in combination with one or more other epoxy resins. The other epoxy resin is preferably liquid at room temperature. But, if it is solid at room temperature, it is made liquid by diluting with another liquid epoxy resin or a diluent, and is used.

Concrete examples of the other epoxy resins include bisphenol A-type epoxy resins, bisphenol F-type epoxy resins; novolak-type epoxy resins such as phenolic novolak-type epoxy resins and cresol novolak-type epoxy resins; nitrogen-containing cyclic epoxy resins such as isocyanurate-type epoxy resins and hydantoin-type epoxy resins; alicyclic epoxy resins; hydrogenated bisphenol A-type epoxy resins; aliphatic epoxy resins; glycidyl ether-type epoxy resins, bisphenol S-type epoxy resins; biphenyl-type epoxy resins (major resins giving low-water-absorbing cured products), dicyclocyclic epoxy resins, naphthalene-type epoxy resins and the like.

The epoxy resin may be in advance modified by addition of a compound reactive with epoxy group, such as alcohol or acid anhydride.

More specifically, examples of the isocyanurate-type epoxy resins include 1,3,5-triglycidyl isocyanurate, 1-allyl-3,5-diglycidyl isocyanurate, 1,3-diallyl-5-glycidyl isocyanurate and the like.

More specifically, examples of the alicyclic epoxy resins include compounds represented by the following general formula (1) wherein an oxygen atom of epoxy group is bound to neighboring two carbon atoms in the aliphatic ring, compounds represented by the following general formula (2) wherein epoxy groups are bound to the aliphatic ring directly via single bond and the like.

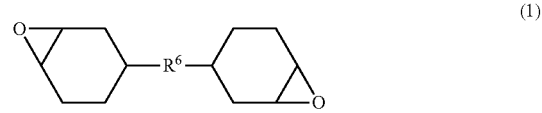

wherein R⁶ represents a single bond or a connecting group (a bivalent group having one or more atoms). Examples of the connecting groups include bivalent hydrocarbons, carbonyl, ether, ester, carbonate, amide, groups in combination thereof and the like.

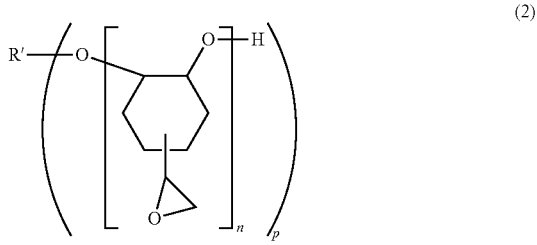

(2)

wherein, n is an integer of 1 to 30; p is an integer of 1 to 10; R' represents a group obtained by removing p-OH groups from a p-valent alcohol.

Typical examples of the alicyclic epoxy compounds represented by the general formula (1) include 3,4-epoxycyclohexenylmethyl-3',4'-epoxycylcohexanecarboxylate and the like.

Typical examples of the alicyclic epoxy compounds represented by the general formula (2) include an adduct of 2,2-bis(hydroxymethyl)-1-butanol to 1,2-epoxy-4-(2-oxiranyl)cyclohexane, and the like.

The content of the glycidylglycoluril represented by the general formula (B) above is not particularly limited, but preferably 0.1 to 100% by weight with respect to 100% by weight of the total amount of the epoxy group-containing compounds contained in the resin composition according to the invention.

Component (2): Glass Filler

The component (2) or glass filler is not particularly limited and any known glass filler may be used. Examples thereof include glass beads, glass flakes, glass powders, milled glasses, glass fibers, glass fiber cloths (for example, glass cloths, glass nonwoven fabrics, etc.) and the like. In particular, glass beads, glass flakes and glass powders are preferred for increase of filling factor and for improvement of moisture absorption-resistant reflow properties and thermal shock resistance.

The kind of the glass constituting the glass filler is not particularly limited, and examples thereof include T glass, E glass, C glass, A glass, S glass, L glass, D glass, NE glass, quartz glass, low dielectric constant glass, high-dielectric constant glass and the like. In particular, E-glass, T glass and NE glass are preferable as they contain a smaller amount of ionic impurities and are thus superior in heat resistance and electric insulating property. In the resin composition according to the invention, the glass fillers may be used alone or in combination of two or more.

The refractive index of the glass filler for sodium D line (light at a wavelength of 589.29 nm) is not particularly limited, but it is preferably in the range of 1.40 to 2.10. When the refractive index is out of the range above, the cured product may show significantly lower transparency. The refractive index of glass filler for sodium D line can be determined, for example, by using an Abbe refractometer (measurement temperature: 25° C.).

When glass beads or glass powder is used as the glass filler, the average diameter thereof is not particularly limited, but it is preferably in the range of 0.5 to 200 μm. The average diameter of the glass filler can be determined, for example, by measuring the particle diameter of the glass filler (glass beads, glass filler, or the like) using a laser diffraction/scattering particle distribution analyzer and calculating the average.

In turn, when a glass fiber cloth such as glass cloth is used as the glass filler, the weaving pattern of the filaments is not particularly limited, and examples thereof include plain weave, basket weave, satin weave, twill weave and the like. The thickness of the glass fiber cloth (such as nonwoven glass fabric) is not particularly limited, but it is preferably in the range of 20 to 200 μm. A single sheet of the glass fiber cloth (such as nonwoven glass fabric) may be used or alternatively, multiple sheets thereof may be used, as they are piled.

The glass filler may be a product surface-finished with a known surface finishing agent. Examples of the surface finishing agents include silane-coupling agents such as γ-aminopropyltriethoxysilane and γ-glycidoxypropyltriethoxysilane, surfactants, inorganic acids and the like.

The content (blending amount) of the glass filler is not particularly limited, but it is preferably in the range of 0.1 to 200 parts by mass with respect to 100 parts by mass of the total amount of the epoxy group-containing compounds contained in the resin composition according to the invention.

Component (3): Curing Agent

The resin composition according to the invention may comprise additionally a component (3) curing agent. The curing agent is a compound having a function to cure the epoxy group-containing compound and any known curing agent may be used as the epoxy resin-curing agent.

The curing agent is preferably an acid anhydride that is liquid at room temperature. Examples thereof include methyltetrahydrophthalic anhydride, methylhexahydrophthalic anhydride, dodecenylsuccinic anhydride, methyl-endomethylene tetrahydrophthalic anhydride and the like. Acid anhydrides that are solid at room temperature, such as phthalic anhydride, tetrahydrophthalic anhydride, hexahydrophthalic anhydride and methylcyclohexanedicarboxylic anhydride, can also be used favorably as the curing agents used in the invention, for example, as they are dissolved in an acid anhydride that is liquid at room temperature.

The curing agents may be used alone or in combination of two or more. As described above, saturated monocyclic hydrocarbon dicarboxylic acid anhydrides (including those having substituent groups, such as alkyl groups bound to the ring) are preferable as the curing agents, from the viewpoints of the heat resistance, lightfastness and cracking resistance of the cured product.

In the invention, commercially available products such as "Rikacid MH-700" (product name, produced by New Japan Chemical Co., Ltd.), "Rikacid MH-700F" (produced by New Japan Chemical Co., Ltd.) and "HN-5500" (product name, produced by Hitachi Chemical Co., Ltd.) can also be used as the curing agents.

The content (blending amount) of the curing agent is not particularly limited, but it is preferably in the range of 10 to 200 parts by mass with respect to 100 parts by mass of the total amount of the epoxy group-containing compounds contained in the resin composition according to the invention.

Component (4): Curing Accelerator

The resin composition according to the invention may further comprise a component (4) or a curing accelerator. The curing accelerator is a compound having a function to increase the curing velocity when the epoxy group-containing compound is cured by the curing agent.

The curing accelerator used may be any known curing accelerator. Examples thereof include 1,8-diazabicyclo[5.4.0]undecene-7 (DBU) or the salts thereof (for example, phenol salt, octyl acid salt, p-toluenesulfonic acid salt, formic acid salt, and tetraphenylboric acid salt); 1,5-diazabicyclo[4.3.0]nonene-5 (DBN) or the salts thereof (for example, phenol salt, octyl acid salt, p-toluenesulfonic acid salt, formic acid salt and tetraphenylboric acid salt); tertiary amines such as benzyldimethylamine, 2,4,6-tris(dimethylaminomethyl)phenol and N,N-dimethylcyclohexylamine; imidazoles such as 2-ethyl-4-methylimidazole and 1-cyanoethyl-2-ethyl-4-methylimidazole; phosphoric esters; phosphines such as triphenylphosphine; phosphonium compounds such as tetraphenylphosphonium tetra(p-tolyl)borate; organic metal salts such as zinc octanoate and tin octanoate; metal chelates and the like. The curing accelerators may be used alone or in combination of two or more.

The content (blending amount) of the curing accelerator is not particularly limited, but it is preferably in the range of 0.05 to 5 parts by mass with respect to 100 parts by mass of the total amount of the epoxy group-containing compounds contained in the resin composition according to the invention.

Component (5): Curing Catalyst

The resin composition according to the invention may further comprise a component (5) or a curing catalyst. The curing catalyst is a compound having a function to initiate curing reaction and/or to accelerate curing reaction of the epoxy group-containing compound. The curing catalyst is not particularly limited. Examples thereof include cationic catalysts (cationic polymerization initiators) that generate cationic species and thus initiate polymerization by UV irradiation or heat treatment. The curing catalysts may be used alone or in combination of two or more.

Examples of the cationic catalysts generating cationic species by UV irradiation include hexafluoroantimonate salts, pentafluorohydroxy-antimonate salts, hexafluorophosphate salts, hexafluoroarsenate salts and the like.

Examples of the cationic catalysts generating cationic species by heat treatment include aryldiazonium salts, aryliodonium salts, arylsulfonium salts, allene-ion complexes and the like. Other examples thereof include compounds of a metal such as aluminum or titanium, a chelate compound such as acetoacetic acid or diketones and a silanol such as triphenylsilanol and compounds of a metal such as aluminum or titanium, a chelate compound such as acetoacetic acid or diketones and a phenol such as bisphenol S.

The content (blending amount) of the curing catalyst is not particularly limited, but it is preferably in the range of 0.01 to 50 parts by mass with respect to 100 parts by mass of the total amount of the epoxy group-containing compounds contained in the curable epoxy resin composition. The curing catalyst, when used in the range above, gives a cured product superior in heat resistance, lightfastness and transparency.

Component (6): Polyester Resin

It is preferred that the resin composition according to the invention further comprises a component (6) or polyester resin. The polyester resin, when contained, may improve, in particular, the heat resistance and lightfastness of the cured product and suppress deterioration of the light intensity of optical semiconductor devices obtained therefrom. Alicyclic polyester resins have at least one alicyclic structure (aliphatic ring structure). In particular, it is preferred that the alicyclic polyester resin has an aliphatic ring (alicyclic structure) in the main chain for improvement of the heat resistance and lightfastness of the cured product.

The alicyclic structure in the alicyclic polyester resin is not particularly limited and examples thereof include monocyclic hydrocarbon structures, bridged-ring hydrocarbon structures (for example, bicyclic hydrocarbons, etc.) and the like. In particular, it is preferably a saturated monocyclic hydrocarbon structure or a saturated bridged-ring hydrocarbon structure wherein the aliphatic ring skeleton (carbon-carbon bonds) is entirely made of carbon-carbon single bonds. The alicyclic structure in the alicyclic polyester resin may be introduced in only one or both of the dicarboxylic acid-derived structural unit and the diol-derived structural unit. Thus, the location of the alicyclic structure is not particularly limited.

The alicyclic polyester resin comprises a structural unit derived from a monomer component having an aliphatic ring structure. The monomers having an aliphatic ring structure are, for example, known diols and dicarboxylic acids having an aliphatic ring structure, and examples thereof include, but are not particularly limited to, dicarboxylic acids (including derivatives thereof such as acid anhydrides) having an aliphatic ring structure such as 1,2-cyclohexanedicarboxylic acid, 1,3-cyclohexanedicarboxylic acid, 1,4-cyclohexanedicarboxylic acid, 4-methyl-1,2-cyclohexanedicarboxylic acid, himic acid, 1,4-decahydronaphthalenedicarboxylic acid, 1,5-decahydronaphthalenedicarboxylic acid, 2,6-decahydronaphthalenedicarboxylic acid and 2,7-decahydronaphthalenedicarboxylic acid; five-membered-ring diols such as 1,2-cyclopentanediol, 1,3-cyclopentanediol, 1,2-cyclopentanedimethanol, 1,3-cyclopentanedimethanol and bis(hydroxymethyl)tricyclo[5.2.1.0]decane; six-membered-ring diols such as 1,2-cyclohexanediol, 1,3-cyclohexanediol, 1,4-cyclohexanediol, 1,2-cyclohexanedimethanol, 1,3-cyclohexanedimethanol, 1,4-cyclohexanedimethanol and 2,2-bis(4-hydroxycyclohexyl)propane; diols (including the derivatives thereof) having an aliphatic ring structure such as hydrogenated bisphenol A and the like.

The alicyclic polyester resin may comprise a structural unit derived from a monomer component having no alicyclic structure. Examples of the monomers having no alicyclic structure include aromatic dicarboxylic acid (including the derivatives thereof such as acid anhydrides) such as terephthalic acid, isophthalic acid, phthalic acid and naphthalenedicarboxylic acid; dicarboxylic fatty acids (including the derivatives thereof such as acid anhydrides) such as adipic acid, sebacic acid, azelaic acid, succinic acid, fumaric acid and maleic acid; diols (including the derivatives thereof) such as ethylene glycol, propylene glycol, 1,2-propanediol, 1,3-propanediol, 1,3-butanediol, 1,4-butanediol, neopentylglycol, 1,5-pentanediol, 1,6-hexanediol, 3-methylpentanediol, diethylene glycol, 3-methyl-1,5-pentanediol, 2-methyl-1,3-propanediol, 2,2-diethyl-1,3-propanediol, 2-butyl-2-ethyl-1,3-propanediol xylylene glycol, bisphenol A ethylene oxide adducts, and bisphenol A propylene oxide adducts; and the like. Dicarboxylic acids and diols having no alicyclic structure and having one or more appropriate substituent groups (for example, alkyl and alkoxy groups, halogen atoms, etc.) bound thereto are also included in the monomers having no alicyclic structure.

The content of the monomer unit having an aliphatic ring in all monomer units (all monomer components) constituting the alicyclic polyester resin (100 mol %) is not particularly limited, but it is preferably mol % or more.

Component (7): Organosiloxane Compound

The resin composition according to the invention preferably comprises a component (7) or an organosiloxane compound additionally. The organosiloxane compound is not particularly limited, if it is melt-miscible with the epoxy resin. Thus, various polyorganosiloxanes, i.e., solvent-free solid polyorganosiloxanes or liquid polyorganosiloxanes at room temperature can be used. The polyorganosiloxane used in the invention is preferably a compound uniformly dispersible in the cured product of the resin composition.

An example of the polyorganosiloxane is a compound having a constituent siloxane unit represented by the following general formula (3). The compound has at least one hydroxyl or alkoxy group bound to a silicon atom in the molecule and 10 mol % or more of the monovalent hydrocarbon group bound ($R^7$) to the silicon atom is a substituted or unsubstituted aromatic hydrocarbon group.

$$R^7_m(OR^8)_l SiO_{(4-m-l)/2} \quad (3)$$

wherein $R^7$ each represents a substituted or unsubstituted saturated monovalent hydrocarbon group having 1 to 18 carbon atoms and these groups may be the same as or different from each other; $R^8$ each represents a hydrogen atom or an alkyl group having 1 to 6 carbon atoms and these groups may be the same as or different from each other; and m and l each are an integer of 0 to 3.

In the general formula (3) above, concrete examples of the unsubstituted saturated monovalent hydrocarbon group, among the substituted or unsubstituted saturated monovalent hydrocarbon groups having 1 to 18 carbon atoms $R^7$, include straight-chain or branched alkyl group such as methyl, ethyl, propyl, isopropyl, n-butyl, isobutyl, t-butyl, pentyl, isopentyl, hexyl, isohexyl, heptyl, isoheptyl, octyl, isooctyl, nonyl and decyl; cycloalkyl groups such as cyclopentyl, cyclohexyl, cyclooctyl, dicyclopentyl and decahydronaphthyl; aromatic groups (aryl groups) such as phenyl, naphthyl, tetrahydronaphthyl, tolyl and ethylphenyl; aralkyl groups such as benzyl, phenylethyl, phenylpropyl and methylbenzyl; and the like.

On the other hand, the substituted saturated monovalent hydrocarbon group of $R^7$ in the general formula (3) above is specifically a hydrocarbon group wherein part or all of the hydrogen atoms are replaced by halogen atoms, cyano groups, amino groups, epoxy groups and the like, and concrete examples thereof include substituted hydrocarbon groups such as chloromethyl, 2-bromoethyl, 3,3,3-trifluoropropyl, 3-chloropropyl, chlorophenyl, dibromophenyl, difluorophenyl, β-cyanoethyl, γ-cyanopropyl and β-cyanopropyl and the like.

The group ($OR^8$) in the general formula (3) is a hydroxyl group or an alkoxy group and, when the group ($OR^8$) is an alkoxy group, $R^8$ is specifically an alkyl group described above as $R^7$ that has 1 to 6 carbon atoms. More specifically, $R^8$ is, for example, a methyl, ethyl or isopropyl group. These groups may be the same as or different from each other in the same siloxane unit or between siloxane units.

Further, the polyorganosiloxane preferably has at least one hydroxyl or alkoxy group bound to a silicon atom in the molecule and thus, at least one of the siloxane units constituting the silicone resin preferably has a ($OR^8$) group of the general formula (3).

If the polyorganosiloxane has neither a hydroxyl nor an alkoxy group, it shows insufficient affinity to the epoxy resin and it is less likely to obtain a cured product with sufficient physical properties from the resin composition obtained, probably because the hydroxyl or alkoxy group acts in some way in the curing reaction of the epoxy resin, although the mechanism is yet unclear. The content of the hydroxyl or alkoxy group bound to a silicon atom in the polyorganosiloxane is preferably in the range of 0.1 to 15% by weight in terms of OH group.

In the resin composition according to the invention, a siloxane derivative having an epoxy group in the molecule may be used as the organosiloxane. Addition of the siloxane derivative having an epoxy group in the molecule leads particularly to improvement in heat resistance and lightfastness of the cured product to a higher level.

The siloxane skeleton (Si—O—Si skeleton) in the siloxane derivative having two or more epoxy groups in the molecule is not particularly limited, and examples thereof include cyclic siloxane skeletons; polysiloxane skeletons such as linear silicones and cage- or ladder-type polysilsesquioxane; and the like. In particular, the siloxane skeleton is preferably a cyclic siloxane skeleton or a straight-chain silicone skeleton from the viewpoint of improvement of the heat resistance and lightfastness of the cured product and reduction of the deterioration of light intensity.

Thus, the siloxane derivative having 2 or more epoxy groups in the molecule is preferably a cyclic siloxane having 2 or more epoxy groups in the molecule or a straight-chain silicone having 2 or more epoxy groups in the molecule. The siloxane derivatives having 2 or more epoxy groups in the molecule may be used alone or in combination of two or more.

Concrete examples of the siloxane derivatives having 2 or more epoxy groups in the molecule include:
2,4-di[2-(3-{oxabicyclo[4.1.0]heptyl})ethyl]-2,4,6,6,8,8-hexamethyl-cyclotetrasiloxane,
4,8-di[2-(3-{oxabicyclo[4.1.0]heptyl})ethyl]-2,2,4,6,6,8-hexamethyl-cyclotetrasiloxane,
2,4-di[2-(3-{oxabicyclo[4.1.0]heptyl})ethyl]-6,8-dipropyl-2,4,6,8-tetramethyl-cyclotetrasiloxane,
4,8-di[2-(3-{oxabicyclo[4.1.0]heptyl})ethyl]-2,6-dipropyl-2,4,6,8-tetramethyl-cyclotetrasiloxane,
2,4,8-tri[2-(3-{oxabicyclo[4.1.0]heptyl})ethyl]-2,4,6,6,8-pentamethyl-cyclotetrasiloxane,
2,4,8-tri[2-(3-{oxabicyclo[4.1.0]heptyl})ethyl]-6-propyl-2,4,6,8-tetramethyl-cyclotetrasiloxane,
2,4,6,8-tetra[2-(3-{oxabicyclo[4.1.0]heptyl})ethyl]-2,4,6,8-tetramethyl-cycl otetrasiloxane, silsesquioxanes having 2 or more epoxy groups in the molecule and the like.

Examples of the siloxane derivatives having 2 or more epoxy groups in the molecule for use include the alicyclic epoxy group-containing silicone resins described in JP-A No. 2008-248169 and the organopolysilsesquioxane resins having at least two epoxy functional groups in the molecule described in JP-A No. 2008-19422

The content (blending amount) of the siloxane derivative having two or more epoxy groups in the molecule is not particularly limited, but it is preferably in the range of 1 to 100% by weight with respect to 100% by weight of the total amount of the epoxy group-containing compounds contained in the resin composition according to the invention.
Component (8): Rubber Particle The resin composition according to the invention may comprise a component (8) or rubber particles additionally. Examples of the rubber particles include rubber particles such as particulate NBRs (acrylonitrile-butadiene rubbers), reactive terminal-carboxyl NBRs (CTBNs), metal-free NBRs, and particulate SBRs (styrene-butadiene rubbers).

The rubber particles are preferably those having a multilayer structure (core-shell structure) consisting of a core region with rubber elasticity and at least one shell layer covering the core region.

The rubber particles are preferably, in particular, those made of a polymer containing a (meth)acrylic ester as an essential monomer component and having on the surface hydroxyl groups and/or carboxyl groups (either one or both of hydroxyl and carboxyl groups) as the functional groups for reaction with the epoxy group-containing compound such as an epoxy resin.

It is not preferred that the rubber particles do not have hydroxyl and/or carboxyl groups on the surface, as the cured product becomes cloudy and less transparent by the heat shock, for example, of thermal cycle.

The polymer constituting the rubber elastic core region of the rubber particles is not particularly limited, but preferably contains a (meth)acrylic acid ester such as methyl (meth) acrylate, ethyl (meth)acrylate or butyl (meth)acrylate as an essential monomer component.

The polymer constituting the rubber elastic core region may contain, as its monomer components, other compounds such as aromatic vinyl compounds such as styrene and a-methylstyrene; nitriles such as acrylonitrile and methacrylonitrile; conjugated dienes such as butadiene and isoprene; ethylene; propylene; isobutene and the like.

In particular, the polymer constituting the rubber elastic core region preferably contains, as a monomer component, one or more compounds selected from the group consisting of aromatic vinyls, nitriles and conjugated dienes in combination with a (meth)acrylic ester. Examples of the polymers constituting the core region include binary copolymers such as of (meth)acrylic ester/aromatic vinyl and (meth) acrylic ester/conjugated diene; ternary copolymers such as of (meth)acrylic ester/aromatic vinyl/conjugated diene; and the like. The polymer constituting the core region may contain a silicone such as polydimethylsiloxane and polyphenylmethylsiloxane, polyurethane or the like.

The polymer constituting the core region may contain, as other monomer components, reactive crosslinking monomers having 2 or more reactive functional groups in one monomer (one molecule) such as divinylbenzene, allyl (meth)acrylate, ethylene glycol di(meth)acrylate, diallyl maleate, triallyl cyanurate, diallyl phthalate and butylene glycol diacrylate.

The core region of the rubber particles is particularly preferably a core region made of a (meth)acrylic ester/ aromatic vinyl binary copolymer (in particular, butyl acrylate/styrene copolymer) for easier adjustment of the refractive index of the rubber particles.

The core region of the rubber particles can be prepared by a method commonly used and, for example, it can be prepared by a method of polymerizing the above-mentioned monomers by emulsion polymerization. In the case of the emulsion polymerization method, all monomers may be added and polymerized collectively or part of the monomers may be first polymerized and then the remaining monomers may be added continuously or intermittently for polymerization. Alternatively, a polymerization method using seed particles may be employed.

The polymer constituting the shell layer of the rubber particles is preferably a polymer different from the polymer constituting the core region. As described above, the shell layer preferably has hydroxyl and/or carboxyl groups as functional groups reactive with the epoxy group-containing compound such as an epoxy resin. It is thus possible, in particular, to improve the adhesiveness at the interface with the epoxy resin and give a cured product superior in cracking resistance from the resin composition containing the rubber particles with the shell layer. It is also possible to prevent drop of the glass transition temperature of the cured product.

The polymer constituting the shell layer preferably contains a (meth)acrylic ester such as methyl (meth)acrylate, ethyl (meth)acrylate or butyl (meth)acrylate as an essential monomer component.

For example, if butyl acrylate is used as the (meth)acrylic ester for the core region, a (meth)acrylic ester different from butyl acrylate (for example, methyl (meth)acrylate, ethyl (meth)acrylate, butyl methacrylate or the like) is preferably used as a monomer component for the polymer constituting the shell layer.

Examples of the monomer components other than (meth) acrylic esters include aromatic vinyl compounds such as styrene and a-methylstyrene; nitriles such as acrylonitrile and methacrylonitrile; and the like.

The rubber particles preferably contains one or more monomers above, in particular at least an aromatic vinyl compound, in combination with a (meth)acrylic ester as the monomer components constituting the shell layer for easier adjustment of the refractive index of the rubber particles.

Further, the polymer constituting the shell layer preferably contains a hydroxyl group-containing monomer (for example, a hydroxyalkyl (meth)acrylate such as 2-hydroxyethyl (meth)acrylate) or a carboxyl group-containing monomer (for example, α,β-unsaturated acid such as (meth) acrylic acid, α,β-unsaturated acid anhydride such as maleic anhydride or the like) as the monomer component to form a hydroxyl group and/or a carboxyl group as a functional group reactive with the epoxy group-containing compounds such as the epoxy resin.

The polymer constituting the shell layer of the rubber particles preferably contains, as its monomer components, one or more monomers selected from the monomers above in addition to the (meth)acrylic ester. Thus, the shell layer is preferably, for example, a shell layer made of a ternary copolymer for example of (meth)acrylic ester/aromatic vinyl/hydroxyalkyl (meth)acrylate or (meth)acrylic ester/ aromatic vinyl/α,β-unsaturated acid.

Similarly to the polymer for the core region, the polymer constituting the shell layer may contain, in addition to the monomers above, a reactive crosslinking monomer having 2 or more reactive functional groups in one monomer (one molecule) such as divinylbenzene, allyl (meth)acrylate, ethylene glycol di(meth)acrylate, diallyl maleate, triallyl cyanurate, diallyl phthalate or butylene glycol diacrylate as the other monomer component.

The rubber particles (having a core/shell structure) are prepared by covering a core region with a shell layer. As the method for covering a core region with a shell layer, there may be mentioned, for example, a method in which the copolymer constituting the shell layer is applied on the surface of the rubber elastic core region obtained by the method described above, or a method in which the components constituting the shell layer are graft-polymerized as branch components to the rubber elastic core region obtained by the method described above as a trunk component.

The average diameter of the rubber particles is not particularly limited, but it is preferably in the range of 10 to 500 nm. The refractive index of the rubber particle can be determined as follows, for example. The rubber particles are compression-molded in a mold at 210° C. and 4 MPa to give a flat plate having a thickness of 1 mm; a test sample of 20 mm in length×6 mm in width is cut out from the flat plate obtained. The obtained test sample is subjected to measurement of the refractive index at a sodium D line at 20° C. using a multiwavelength Abbe refractometer (product name: "DR-M2", manufactured by Atago Co., Ltd.), with the test sample adhered to the prism using monobromonaphthalene as the intermediate liquid.

The refractive index of the cured product of the resin composition according to the invention can be determined as follows, for example. A test sample of 20 mm in length×6 mm in width×1 mm in thickness is cut out from a cured product obtained by the heat-curing method described in the section of the following optical semiconductor device, and the test sample is subjected to measurement of the refractive index at a sodium D line at 20° C. using a multiwavelength Abbe refractometer (product name: "DR-M2", manufactured by Atago Co., Ltd.), with the test sample adhered to the prism using monobromonaphthalene as the intermediate liquid.

The content (blending amount) of the rubber particles in the resin composition according to the invention is not particularly limited, but it is preferably in the range of 0.5 to 30 parts by mass with respect to 100 parts by mass of the total amount of the epoxy group-containing compounds contained in the resin composition according to the invention.

Component (9): Additives

The resin composition according to the invention may comprise component (9) or various additives in addition to those described above in the range that does not impair the advantageous effects of the invention.

The reaction can be carried out smoothly, when a hydroxyl group-containing compound such as ethylene glycol, diethylene glycol, propylene glycol or glycerol is contained as the additive. In addition, common additives such as silicones, fluorine-based antifoams, levelling agents, silane-coupling agents such as γ-glycidoxypropyltrimethoxysilane and 3-mercaptopropyltrimethoxysilane; surfactants, silica, inorganic fillers such as alumina, flame retardants, colorants, antioxidants, ultraviolet absorbents, ion adsorbents, pigments, phosphors and release agents can be used in the range that does not deteriorate viscosity and transparency.

The resin composition according to the invention should comprise at least one component (1), i.e., the epoxy resin described above, but the method for producing the same is not particularly limited. Specifically, it can be prepared, for example, by mixing respective components at a predetermined rate and, as needed, defoaming the mixture under vacuum. Alternatively, it can be prepared, for example, by preparing a composition comprising a glycoluril represented by General Formula (B) above as the essential component (referred to also as "epoxy resin") and a composition containing a curing agent and a curing accelerator or a curing catalyst as the essential components (referred to also as "epoxy-curing agent") separately, mixing the "epoxy resin" and the "epoxy-curing agent" at a predetermined rate and, as needed, defoaming the mixture under vacuum.

The glass filler may be blended previously as the component constituting the epoxy resin and/or the epoxy-curing agent or as a component other than the epoxy resin and the epoxy resin-curing agent when the epoxy resin and the epoxy-curing agent are mixed.

The temperature at which these components are mixed when the epoxy resin is prepared is not particularly limited, but it is preferably in the range of 30° C. to 150° C. The temperature at which these components are mixed when the epoxy-curing agent is prepared is not particularly limited, but it is in the range preferably of 30° C. to 100° C. A known apparatus such as a planetary centrifugal mixer, planetary mixer, kneader or dissolver can be used for mixing.

In particular, if the resin composition according to the invention comprises a curing agent and the polyester resin above as essential components, it is preferred that an alicyclic polyester resin and a curing agent are mixed to give a mixture thereof (mixture of the polyester resin and the curing agent), a curing accelerator and other additives are added to the mixture to give an epoxy-curing agent, and then the epoxy-curing agent is mixed with an epoxy resin separately prepared for preparation of a more homogeneous composition.

The temperature when the polyester resin is mixed with the curing agent is not particularly limited, but it is preferably in the range of 60° C. to 130° C. The mixing time is not particularly limited, but it is preferably in the range of 30 to 100 minutes. The mixing is preferably carried out under nitrogen atmosphere, although it is not particularly limited to the condition. A known apparatus described hereinbefore can be used for mixing.

After the polyester resin is mixed with the curing agent, an additional appropriate chemical treatment (for example, hydrogenation or terminal modification of the polyester resin) may be carried out, although it is not particularly needed. Part of the curing agent may react with the polyester resin (for example, with the hydroxyl groups in the polyester resin) in the mixture of the polyester resin and the curing agent.

A cured product superior in heat resistance, lightfastness and thermal shock resistance, in particular, superior in moisture absorption-resistant reflow properties is obtained by curing the resin composition according to the invention. The heating temperature during curing (curing temperature) is not particularly limited, but it is preferably in the range of 45° C. to 200° C. The period of heating for curing (curing period) is not particularly limited, but it is preferably in the range of 30 to 600 minutes. The curing condition depends on various conditions. For example, the curing period is made shorter when the curing temperature is higher, and the curing period is made longer when the curing temperature is lower.

The resin composition according to the invention is used suitably as a resin composition for sealing optical semiconductors. The use of the resin composition as a resin composition for sealing optical semiconductors makes it possible to provide an optical semiconductor device having an optical semiconductor element sealed with a cured product that is superior in heat resistance, lightfastness and thermal shock resistance, particularly superior in moisture absorption-resistant reflow properties.

The optical semiconductor device thus obtained is resistant to deterioration in light intensity over time, in particular, to deterioration in light intensity when it is heated in the reflow process after storage under high-humidity condition even when it has a high-output and high-brightness optical semiconductor element.

In the optical semiconductor device according to the invention, an optical semiconductor element is sealed with the cured product of the resin composition (resin composition for sealing optical semiconductors) according to the invention. The optical semiconductor element is sealed by injecting a resin composition prepared by the method described above into a molding mold and heating the resin under a predetermined condition. In this way, an optical semiconductor device having an optical semiconductor element sealed with the cured product of a curable epoxy resin composition is obtained. The curing temperature and the curing period can be set in the ranges similar to those during preparation of the cured product.

EXAMPLES

Hereinafter, the invention will be described specifically with reference to Examples and Comparative Examples, but the invention is not limited thereto.

Example 1

First, 1,3,4,6-tetraglycidylglycoluril (TG-G, produced by Shikoku Chemicals Corporation.), "Celoxide 2021P" (product name, an alicyclic epoxy compound, produced by Daicel Corporation.) and "Glass Beads CF0018WB15C" (product name, a glass filler, produced by Nippon Frit Co., Ltd.) were mixed uniformly at the blending rate shown in Table 3 (unit: parts by mass) and the mixture was defoamed using a planetary centrifugal stirrer (Awatori Rentaro AR-250. manufactured by Thinky Corporation), to give an epoxy resin.

Then, the epoxy resin, "Rikacid MH-700" (product name, a curing agent, produced by New Japan Chemical Co., Ltd.) as an epoxy-curing agent and "U-CAT18X" (product name, a curing accelerator, produced by San-Apro Ltd.) were mixed uniformly at the blending ratio shown in Table 3 (unit:parts by mass) and the mixture was defoamed in a planetary centrifugal stirrer (Awatori Rentaro AR-250, manufactured by Thinky Co., Ltd.), to give an epoxy resin composition.

Further, the epoxy resin composition was molded into a lead frame of optical semiconductor (InGaN element, 3.5 mm×2.8 mm) and then heated in an oven (resin-curing oven) at 120° C. for 5 hours, to give an optical semiconductor device having an optical semiconductor element sealed with the cured product of the epoxy resin composition.

Examples 2 and 3 and Comparative Example 1

Epoxy resin compositions and optical semiconductor devices having a sealed optical semiconductor element were prepared in the same manner as in Example 1 except that the composition of the epoxy resin composition was changed as shown in Table 3.

The optical semiconductor devices obtained in the Examples and Comparative Example above were subjected to the following evaluation tests.

[Current Test (High-Temperature Current Test)]

The total luminous flux of the optical semiconductor devices obtained in the Examples and Comparative Example was determined using a total luminous flux analyzer and was designated as "total luminous flux at 0 hour." Further, after a current of 30 mA was applied to the optical semiconductor device in a constant-temperature oven at 85° C. for 100 hours, the total luminous flux thereof was determined and designated as "total luminous flux after 100 hours." The light intensity retention rate was calculated according to the formula below. The results are shown in the column of the "Light intensity retention rate (%)" in Table 3.

(Light intensity retention rate (%)=(Total luminous flux (lm) after 100 hours)/(Total luminous flux (lm) at 0 hour)×100

[Solder Heat Resistance Test]

Each of the optical semiconductor devices obtained in the Examples and Comparative Example above (respectively two test samples for each epoxy resin composition) was left still under a condition of a temperature of 30° C. and a relative humidity of 70% for 192 hours for absorption of water.

The optical semiconductor device was then placed in a reflow furnace and heat-treated under the heating condition described below.

The optical semiconductor device was then taken out of the reflow furnace and allowed to cool under a room temperature environment and then placed again in the reflow furnace for heat treatment under the same condition. Thus, in the solder heat resistance test, the heat history under the following heating condition was given twice to the optical semiconductor device.

[Heating Condition (as Surface Temperature of Optical Semiconductor Device)]

(1) Preheating at 150° C. to 190° C. for 60 to 120 seconds (2) Main heating after preheating at 217° C. or higher for 60 to 150 seconds, maximum temperature of 260° C.

The heating rate during conversion from the preheating to main heating temperature was adjusted to 3° C./second at the highest. The optical semiconductor device was then observed using a digital microscope (product name: "VHX-900", manufactured by Keyence Corp.) for examination of whether there are cracks having a length of 90 μm or more on the cured product and whether there is electrode exfoliation (exfoliation of the cured product from electrode surface).

The number of the optical semiconductor devices having the cracks with a length of 90 μm or more in the cured product in the two optical semiconductor devices is shown in the column of the "Solder heat resistance test [crack number]" of Table 3 and the number of the optical semiconductor device showing electrode exfoliation is shown in the column of the "Solder heat resistance test [electrode exfoliation number]" of Table 3.

[Thermal Shock Test]

Each of the optical semiconductor devices obtained in the Examples and Comparative Example above (respectively two test samples used for each epoxy resin composition) was subjected to 200 cycles of heat shock by exposing it to an atmosphere at −40° C. for 30 minutes and then to an atmosphere at 120° C. for 30 minutes, using a thermal shock test machine. The length of the cracks generated in the cured product of the optical semiconductor device was then observed using a digital microscope (product name: "VHX-900", manufactured by Keyence Corporation) and the number of the optical semiconductor devices having a crack with a length of 90 μm or more in the cured product in the two optical semiconductor devices was counted. The results are shown in the column of "Thermal shock test [crack number]" in Table 3.

[Comprehensive Judgment]

After the tests above, those satisfying the following conditions (1) to (4) was considered ○ (favorable). On the other hand, those that does not satisfy any one of the following conditions (1) to (4) was considered x (unfavorable).

(1) Current test: The light intensity retention rate is 90% or more.

(2) Solder heat resistance test: The number of the optical semiconductor devices having cracks with a length of 90 μm or more in the cured product is 0.

(3) Solder heat resistance test: The number of the optical semiconductor devices showing electrode exfoliation is 0.

(4) Thermal shock test: The number of the optical semiconductor devices having cracks with a length of 90 μm or more in the cured product is 0.

The results are shown in the column of the "Comprehensive judgment" in Table 3.

TABLE 3

|  | Examples | | | Comparative Examples |
|---|---|---|---|---|
|  | 1 | 2 | 3 | 1 |
| Composition (parts by mass) | | | | |
| TG-G | 100 | 50 | 30 | |
| CEL2021P | | 50 | 70 | 100 |
| Glass filler | 5 | 5 | 5 | 5 |
| MH-700 | 100 | 100 | 100 | 100 |
| U-CAT18X | 0.5 | 0.5 | 0.5 | 0.5 |
| Evaluation | | | | |
| Light retention rate (%) | 95 | 94 | 91 | 85 |
| Solder heat resistance test (crack number) | 0 | 0 | 0 | 2 |
| Solder heat resistance test (electrode exfoilation number) | 0 | 0 | 1 | 2 |
| Thermal shock test (crack number) | 0 | 0 | 0 | 2 |
| Comprehensive judgment | ○ | ○ | ○ | X |

(3) A Thermosetting Resin Composition Comprising a Phenol Compound

The thermosetting resin composition according to the invention comprises the glycidylglycoluril represented by the general formula (B) above and a phenol resin as components.

Examples of the glycidylglycolurils in the thermosetting resin composition according to the invention include:
1,3-diglycidylglycoluril,
1,4-diglycidylglycoluril,
1,6-diglycidylglycoluril,
1,3,4-triglycidylglycoluril,
1,3,4,6-tetraglycidylglycoluril,
1-glycidyl-3a-methyl-glycoluril,
1,3-diglycidyl-3a-methyl-glycoluril,
1,4-diglycidyl-3a-methyl-glycoluril,
1,6-diglycidyl-3a-methyl-glycoluril,
1,3,4-triglycidyl-3a-methyl-glycoluril,
1,3,4,6-tetraglycidyl-3a-methyl-glycoluril,
1-glycidyl-3a,6a-dimethyl-glycoluril,
1,3-diglycidyl-3a,6a-dimethyl-glycoluril,
1,4-diglycidyl-3a,6a-dimethyl-glycoluril,
1,6-diglycidyl-3a,6a-dimethyl-glycoluril,
1,3,4-triglycidyl-3a,6a-dimethyl-glycoluril,
1,3,4,6-tetraglycidyl-3a,6a-dimethyl-glycoluril,
1-glycidyl-3a,6a-diphenyl-glycoluril,
1,3-diglycidyl-3a,6a-diphenyl-glycoluril,
1,4-diglycidyl-3a,6a-diphenyl-glycoluril,
1,6-diglycidyl-3a,6a-diphenyl-glycoluril,
1,3,4-triglycidyl-3a,6a-diphenyl-glycoluril,
1,3,4,6-tetraglycidyl-3a,6a-diphenyl-glycoluril and the like.

According to the invention, an epoxy compound (resin) having two or more epoxy groups in the molecule may be used in combination with the glycidylglycoluryl compound. Examples of the epoxy resins include bisphenol A-type epoxy resins, bisphenol F-type epoxy resins, novolak-type epoxy resins, cresol novolak-type epoxy resins, glycidyl ether-type epoxy resins, alicyclic epoxy resins, heterocyclic epoxy resins and the like.

In the invention, the blending ratio of the epoxy components including the glycidylglycoluril and the epoxy compound above in the entire thermosetting resin composition is preferably in the range of 10 to 60 mass %, and more preferably in the range of 20 to 50 mass %.

According to the invention, the phenol compound (resin) acts as a curing agent for the epoxy compound (resin).

The phenol compounds for use may be a mixture of various phenol resins that have been used as the curing agents for epoxy compounds, specifically phenol resins such as cresol novolak resins and phenolic novolak resins.

In particular, phenol and cresol resins having a naphthol skeleton, a naphthalene diol skeleton, a biphenyl skeleton or a dicyclopentadiene skeleton in the molecular structure are preferable.

Examples of the phenol resins include an α-naphthol skeleton-containing cresol novolak resin SN-485 (product name, produced by Nippon Steel Chemical, hydroxyl equivalent: 215), a naphthalene diol skeleton-containing phenolic novolak resin SN-395 (product name, produced by Nippon Steel Chemical Co., Ltd., hydroxyl equivalent: 105), a biphenyl skeleton-containing phenolic novolak resin MEH-7851-3H (product name, produced by Meiwa Plastic Industries Ltd., hydroxyl equivalent: 223), a dicyclopentadiene skeleton-containing phenolic novolak resin DPP-6125 (product name, produced by JX Nippon Oil & Energy Corporation, hydroxyl equivalent: 185) and the like.

These phenol resins may be used alone or as a mixture of two or more.

The blending amount of the phenol resin is preferably in the range of a ratio of the number of the phenolic hydroxyl groups in the phenol resin to the number of the epoxy groups in the epoxy resin [number of phenolic hydroxyl groups/number of epoxy groups] of 0.5 to 1, and more preferably in the range of 0.8 to 1. It is possible to prevent deterioration of heat resistance when the ratio is 0.5 or more and to prevent the deterioration of the adhesiveness to the organic fiber described below when it is 1 or less.

The thermosetting resin composition according to the invention may contain inorganic fillers, curing accelerators, flame retardants such as metal hydroxide and zinc borate, antifoams, levelling agents and other additives commonly used, as needed, in the range that does not impair the advantageous effects of the invention.

Examples of the inorganic fillers include powders such as of fused silica, synthetic silica, crystalline silica, alumina, zirconia, talc, clay, mica, calcium carbonate, magnesium hydroxide, aluminum hydroxide, titanium white, red iron oxide, silicon carbide, boron nitride, silicon nitride and aluminum nitride; the beads thereof, single crystal fibers, glass fibers and the like. These fillers can be used alone or as a mixture of two or more.

Silica can be used after it is surface-treated, as needed, for example, with a silane coupling agent or titanium coupling agent.

Examples of the silane coupling agents include epoxysilane coupling agents such as γ-glycidoxypropyltrimethoxysilane and γ-glycidoxypropylmethyldiethoxysilane; aminosilane coupling agents such as γ-aminopropyltrimethoxysilane and N-β-(aminoethyl)-γ-aminopropyl-trimethoxysilane; and the like.

The blending ratio of the inorganic filler in the entire thermosetting resin composition is preferably in the range of 20 to 50 mass %, and more preferably in the range of 30 to 40 mass %. When the blending ratio is 20 mass % or more, deterioration of heat resistance is prevented.

Examples of the curing accelerators include: imidazole compounds such as 2-heptadecylimidazole, 2-methylimidazole, 2-ethylimidazole, 2-phenylimidazole, 2-phenyl-4-methylimidazole, 4-methylimidazole, 4-ethylimidazole, 2-phenyl-4-hydroxymethylimidazole, 2-phenyl-4-methyl-imidazole, 1-cyanoethyl-2-methylimidazole, 2-phenyl-4-methyl-5-hydroxymethylimidazole and 2-phenyl-4,5-dihydroxymethylimidazole; organic phosphine compounds such as trimethylphosphine, triethylphosphine, tributylphosphine, triphenylphosphine, tri(p-methylphenyl)phosphine, tri(nonylphenyl)phosphine, methyldiphenylphosphine, dibutylphenylphosphine, tricyclohexylphosphine, bis(diphenylphosphino)methane, 1,2-bis(diphenylphosphino)ethane, tetraphenylphosphonium tetraphenylborate, triphenylphosphine tetraphenylborate and triphenylphosphine triphenylborane; diazabicycloalkene compounds such as 1,8-diazabicyclo[5,4,0]undecene-7 (DBU) and 1,5-diazabicyclo[4,3,0]nonene-5; tertiary amine compounds such as triethylamine, triethylenediamine, benzyldimethylamine, a-methylbenzyldimethylamine, triethanolamine, dimethylaminoethanol and tris(dimethylaminomethyl)phenol; and the like.

These compounds can be used alone or as a mixture of two or more.

The thermosetting resin composition according to the invention is prepared as a resin solution (varnish) by dissolving or dispersing the respective components above in a suitable solvent.

The solvent in which the thermosetting resin composition is dissolved or dispersed is not particularly limited, but it has preferably a boiling point of 220° C. or lower so that the amount thereof remaining in the prepreg is reduced as much as possible. Concrete examples of the solvents include γ-butylolactone, N-methyl-2-pyrrolidone, dimethylacetamide, methylethylketone, toluene, acetone, ethylcellosolve, methylcellosolve, cyclohexanone, propylene glycol monomethyl ether and the like and these solvents can be used alone or as a mixture of two or more. Among the solvents above, propylene glycol monomethyl ether is preferred.

The solid content concentration of the varnish is not particularly limited either, but it is preferably in the range of 40 to 80 mass %, more preferably in the range of 60 to 70 mass %, as an excessively low concentration leads to decrease of the amount of the resin impregnated into the prepreg and an excessively high concentration leads to increase of the viscosity of the varnish, which may lead to unfavorable appearance of the prepreg.

The prepreg can be prepared by applying or impregnating the varnish into a substrate and then removing the solvent therefrom by drying. The substrate to be impregnated with the varnish is preferably a woven or nonwoven fabric made of glass fiber, aramide fiber, poly-p-benzoxazole fiber, polyarylate fiber or the like. The weaving pattern of the woven fabric is not particularly limited, but plain weaving is preferred from the viewpoint of flatness.

The amount of the varnish with which the prepreg is impregnated is preferably in the range of 40 to 70 mass % as solid content with respect to the total amount of the varnish and the substrate. When the amount is mass % or more, it is prevented that unimpregnated regions are generated in the substrate, and also that voids and shortage are generated on the laminated board when the prepreg is prepared. When it is 70 mass % or less, it is prevented that the difficulty in producing a uniform laminated board or a printed wiring board is caused due to larger fluctuation in thickness. The method of impregnating the varnish into the substrate and the method of drying the composite after impregnation or application are not particularly limited and those methods known in the art can be employed.

A laminated board is prepared by piling a desired number of the prepregs thus obtained and pressurizing the pile under heat. A metal-laminated board is prepared by placing a metal foil such as copper foil to one or both faces of the composite of a desired number of prepregs and pressurizing the composite under heat.

Further, the printed wiring board according to the invention is prepared by processing the metal-laminated board by etching according to a common method and then laminating thereon semiconductor chips such as silicon chips. The processing condition for production of the laminated board or the metal-laminated board is not particularly limited, but the heating temperature is usually in the range of about 170 to 200° C., the pressure is usually in the range of about 5 to 50 MPa, and the heat-pressurizing period is in the range of about 90 to 150 minutes.

EXAMPLES

Hereinafter, the present invention will be described specifically with reference to Examples and Comparative Examples, but the invention is not limited thereto.

Main raw materials used in the Examples and Comparative Examples and Evaluation tests employed in the Examples and Comparative Examples are as follows:
[Main Raw Materials]
(i) Epoxy Compounds 1,3,4,6-tetraglycidylglycoluril, product name: "TG-G", produced by Shikoku Chemicals Corp.

Bisphenol F-type epoxy resin, product name: "YDF8170", produced by Tohto Chemical Industry Co., Ltd.

Naphthalene epoxy resin, product name: "HP4032D", produced by DIC Corp.

Naphthol aralkyl-type epoxy resin, product name: "ESN-175", produced by Tohto Chemical Industry Co., Ltd.
(ii) Phenol Compound Novolak-type phenol resin, product name: "MEH-7851-3H", produced by Meiwa Plastics Industries Ltd.
(iii) Inorganic Filler Fused silica, product name: "SE1050", produced by Admatechs
(iv) Imidazole-based curing accelerator 2-phenyl-4-methyl-5-hydroxymethylimidazole, product name: "2P4MHZ", produced by Shikoku Chemicals Corp.
[Evaluation Tests]
(1) Glass Transition Temperature The glass transition temperature was determined using a DMA instrument (dynamic viscoelasticity analyzer DMA983, manufactured by TA Instruments) at a heating rate of 5° C./minute and the tan δ peak position was used as the glass transition temperature.
(2) Linear Expansion Coefficient The linear expansion coefficient in the plane direction (X direction) was determined under the condition of a 5° C./minute, using a TMA instrument (manufactured by TA Instruments).
(3) Solder Heat Resistance The solder heat resistance was determined according to JIS C 6481. In the test, a test sample was subjected to PCT treatment for water absorption at 121° C. and 100% for 2 hours; it was then immersed in a solder bath at 288° C. for 30 seconds; and it was examined whether the test sample has abnormality in appearance.

Evaluation result: "No change" or "Swelling observed (there are swollen regions generally)."

(4) Peel Strength

The peel strength was determined at 23° C. The peel strength was determined according to JIS C 6481.

Example 1

Preparation of Varnish

Propylene glycol monomethylether was added as a solvent to 1,3,4,6-tetraglycidylglycoluril (20 parts by mass), a novolak-type phenol resin (50 parts by mass), fused silica (40 parts by mass) and an imidazole-based curing accelerator (0.5 part by mass) and the mixture was stirred with a high-speed agitating apparatus, to give a resin varnish having a resin composition content of 70 mass % in terms of solid content.

<Preparation of Prepreg>

The resin varnish was impregnated in an amount of 80 parts by mass as solid matter into 100 parts by mass of a glass cloth (thickness: 0.18 mm, produced by Nitto Boseki Co., Ltd.) and the resulting glass cloth was dried in a drying oven at 190° C. for 7 minutes to give a prepreg having a resin composition content of 44.4 mass %.

<Preparation of Laminated Board>

Two sheets of the prepreg was piled; an electrolytic copper foil having a thickness of 18 μm (YGP-18, produced by Nippon Denkai) was adhered to both faces; and the laminate was subjected to heat-pressure molding at a pressure of 4 MPa and a temperature of 220° C. for 180 minutes, to give a double-sided copper-clad laminated board having a thickness of 0.4 mm.

<Evaluation of Laminated Board>

The double-sided copper-clad laminated board was etched on the entire surface; a test sample of 6 mm×25 mm was prepared and the glass transition temperature thereof was measured.

The double-sided copper-clad laminated board was etched on the entire surface; a test sample of 5 mm×20 mm was prepared and the linear expansion coefficient thereof was measured.

The double-sided copper-clad laminated board was cut to a piece of 50 mm×50 mm with a grinder saw; it was etched to give a test sample retaining ¼ of the copper foil, and the solder heat resistance thereof was measured.

A test sample of 100 mm×20 mm was prepared from the double-sided copper-clad laminated board and the peel strength thereof was measured.

These measurement results are shown in Table 4.

<Preparation of Printed Wiring Board>

Through holes were formed in the double-sided copper-clad laminated board with a 0.1 mm drill bit and the through holes were filled with a plating material. Further, both faces thereof were patterned by etching to give an inner layer circuit board. The prepreg prepared above was placed on the top and bottom surfaces of the inner layer circuit board, and the composite was pressure molded under heat and vacuum using a vacuum-pressure laminator at a temperature of 100° C. and a pressure of 1 MPa. The composite was cured by being heating in a hot air dryer at 170° C. for 60 minutes to give a laminated product.

The electrolytic copper foil layer on the surface was then subjected to blackening treatment and via holes 60 μm in diameter for interlayer connection were formed using a carbon dioxide gas laser. The composite was then immersed into a swelling solution (Swelling Dip Securiganth P, produced by Atotech Japan) at 70° C. for 5 minutes and additionally in an aqueous potassium permanganate solution (Concentrate Compact CP, produced by Atotech Japan) at 80° C. for 15 minutes. After neutralization, it was subjected to via hole desmear treatment.

The surface of the electrolytic copper foil layer was then etched to a depth of about 1 μm by flash etching; the composite was subjected to electroless copper plating to a thickness of 0.5 μm; a resist layer for the electrolysis copper plating was pattern-copper-plated to a thickness of 18 μm and the composite was post-cured by heating at a temperature of 200° C. for 60 minutes. The plating resist was then removed and the entire surface was flash etched to give a pattern with L/S=20/20 μm. Finally, a solder resist (PSR4000/AUS308, produced by Taiyo Ink Mfg. Co., Ltd.) was formed on the circuit surface to a thickness of 20 μm to give a multilayer printed wiring board.

Examples 2 to 4 and Comparative Example 1

Resin varnishes (having a resin composition content of 70 mass % in terms of solid content), prepregs (having a resin composition content of 44.4 mass %), laminated boards and printed wiring boards having the composition described in Table 4 were prepared in the same manner as in Example 1.

The glass transition temperature, linear expansion coefficient, solder heat resistance and peel strength of the laminated boards were determined in a manner similar to Example 1. The measurement results obtained are shown in Table 4.

TABLE 4

|  | Examples | | | | Comparative Examples |
|---|---|---|---|---|---|
|  | 1 | 2 | 3 | 4 | 1 |
| Composition (parts by mass) | | | | | |
| 1,3,4,6-Tetraglycidylglycoluril | 20 | 10 | 10 | 10 | 35 |
| Bisphenol F-type epoxy resin |  | 18 |  |  |  |
| Naphthalene epoxy resin |  |  | 16 |  |  |
| Naphthol aralkyl-type epoxy resin |  |  |  | 28 |  |
| Novolak-type phenol resin | 50 | 50 | 50 | 50 | 50 |
| Fused silica | 40 | 40 | 40 | 40 | 40 |
| 2-Phenyl-4-methyl-5-hydroxymethyl-imidazole | 0.5 | 0.5 | 0.5 | 0.5 | 0.5 |
| Evaluation tests | | | | | |
| Glass transition temperature (° C.) | 290 | 230 | 250 | 260 | 190 |
| Thermal expansion coefficient α1 (° C.) | 8.9 | 9.9 | 9.1 | 9.3 | 13.2 |

TABLE 4-continued

|  | Examples | | | | Comparative Examples |
|---|---|---|---|---|---|
|  | 1 | 2 | 3 | 4 | 1 |
| Solder heat resitance | not abnormal | not abnormal | not abnormal | not abnormal | bulge |
| Peel strength (kN/m) | 1.4 | 1.1 | 1.2 | 1.2 | 0.7 |

(4) An Alkali-Developing, Photocurable/Thermosetting Resin Composition

The alkali-developing photocurable/thermosetting resin composition according to the invention comprises:
(a) the glycidylglycoluril represented by the general formula (B) above,
(b) a photosensitive prepolymer having two or more unsaturated double bonds in the molecule, and
(c) a photopolymerization initiator.

In the invention, the glycidylglycoluril is a glycidylglycoluril represented by the general formula (B) above, i.e., an epoxy compound, and examples thereof include:
1-glycidylglycoluril,
1,3-diglycidylglycoluril,
1,4-diglycidylglycoluril,
1,6-diglycidylglycoluril,
1,3,4-triglycidylglycoluril,
1,3,4,6-tetraglycidylglycoluril,
1-glycidyl-3a-methylglycoluril,
1,3-diglycidyl-3a-methylglycoluril,
1,4-diglycidyl-3a-methylglycoluril,
1,6-diglycidyl-3a-methylglycoluril,
1,3,4-triglycidyl-3a-methylglycoluril,
1,3,4,6-tetraglycidyl-3a-methylglycoluril,
1-glycidyl-3a,6a-dimethylglycoluril,
1,3-diglycidyl-3a,6a-dimethylglycoluril,
1,4-diglycidyl-3a,6a-dimethylglycoluril,
1,6-diglycidyl-3a,6a-dimethylglycoluril,
1,3,4-triglycidyl-3a,6a-dimethylglycoluril,
1,3,4,6-tetraglycidyl-3a,6a-dimethylglycoluril,
1-glycidyl-3a,6a-diphenylglycoluril,
1,3-diglycidyl-3a,6a-diphenylglycoluril,
1,4-diglycidyl-3a,6a-diphenylglycoluril,
1,6-diglycidyl-3a,6a-diphenylglycoluril,
1,3,4-triglycidyl-3a,6a-diphenylglycoluril,
1,3,4,6-tetraglycidyl-3a,6a-diphenylglycoluril and the like.

These glycolurils may be used alone or in combination of two or more.

In the invention, examples of the epoxy compounds or epoxy resins excluding the glycidylglycolurils above (hereinafter, both of them combined will be referred to as "epoxy resins") include compounds having two or more epoxy groups in the molecule such as bisphenol A-type epoxy resins, bisphenol S-type epoxy resins, bisphenol F-type epoxy resins, phenolic novolak-type epoxy resins, cresol novolak-type epoxy resins, alicyclic epoxy resins, diglycidyl ethers of propylene glycol and polypropylene glycol, polytetramethylene glycol diglycidyl ethers, glycerol polyglycidyl ethers, trimethylolpropane glycidyl ether, phenyl-1,3-diglycidyl ether, biphenyl-4,4'-diglycidyl ether, 1,6-hexanediol glycidyl ether, ethylene glycol and propylene glycol diglycidyl ethers, sorbitol polyglycidyl ethers, sorbitan polyglycidyl ethers, pentaerythritol glycidyl ether, tris (2,3-epoxypropyl) isocyanurate and triglycidyl tris(2-hydroxyethyl)isocyanurate; and the like.

The alkali-developing photocurable/thermosetting resin composition is cured by using a known curing accelerator for epoxy resins, for example an S-triazine compound such as melamine, an imidazole compound such as imidazole and 2-ethyl-4-methylimidazole, or the derivative thereof or a phenol compound, as reaction accelerator and, to provide a cured film improved in heat resistance, chemical resistance, adhesiveness and pencil hardness.

In the invention, the photosensitive prepolymer having two or more unsaturated double bonds in the molecule is a polymer or an oligomer having two or more epoxy groups in the molecule. Examples thereof include polyfunctional epoxy compounds having two or more epoxy groups in the molecule (see the epoxy resins described above); copolymers of alkyl (meth)acrylate and glycidyl (meth)acrylate; photosensitive prepolymers obtained by reacting an unsaturated monocarboxylic acid having an unsaturated double bond to copolymers of a hydroxyalkyl (meth)acrylate, an alkyl (meth)acrylate and glycidyl (meth)acrylate and then addition-reacting an unsaturated or saturated polyvalent carboxylic anhydride thereto; photosensitive prepolymers obtained by reacting an unsaturated compound having an unsaturated double bond and an epoxy group in the molecule, such as glycidyl (meth)acrylate, to a carboxyl group-containing oligomer or polymer, such as copolymers of alkyl (meth)acrylate and (meth)acrylic acid; and the like. (Meth) acrylate, as used herein, means acrylate, methacrylate or a mixture thereof and the same shall apply to (meth)acrylic acid.

Photosensitive prepolymers, which have many free carboxyl groups on the side chains, can be developed with a dilute aqueous alkaline solution and simultaneously, react in addition reaction between the epoxy groups in the epoxy compound separately added as a heat curing component and the free carboxyl groups on the side chains after exposure and development and subsequent post-heating of the film, giving a cured film superior in properties such as heat resistance, solvent resistance, acid resistance, adhesiveness and electrical properties.

The total content of the glycoluril and the epoxy resins other than the glycoluril is preferably 0.01 to 200 parts by mass with respect to 100 parts by mass of the photosensitive prepolymer.

In the invention, examples of the photopolymerization initiators include benzoins and benzoin alkyl ethers such as benzil, benzoin, benzoin methyl ether and benzoin isopropyl ether; acetophenones such as acetophenone, 2,2-dimethoxy-2-phenylacetophenone, 2,2-diethoxy-2-phenylacetophenone, 1,1-dichloroacetophenone, 1-hydroxycyclohexylphenylketone, 2-methyl-1-(4-methylthiophenyl)-2-morpholinopropan-1-one, N,N-dimethylaminoacetophenone and 2-benzyl-2-dimethylamino-1-(4-morpholino phenyl)-butanone-1; anthraquinones such as 2-methyl anthraquinone, 2-ethyl anthraquinone, 2-tert-butyl anthraquinone, 2-aminoanthraquinone, 1-chloroanthraquinone and 2-amylanthraquinone;

thioxanthones such as 2,4-dimethylthioxanthone, 2,4-diethylthioxanthone, 2-chlorothioxanthone and 2,4-diisopropylthioxanthone; ketals such as acetophenone dimethyl ketal and benzil dimethyl ketal; benzophenones such as benzophenone, methylbenzophenone, 4,4'-dichlorobenzophenone and 4,4'-bisdiethylaminobenzophenone; xanthones and the like. These photopolymerization initiators can be used alone or in combination of two or more.

The photopolymerization initiator may be used in combination with one or more of known photosensitizers including tertiary amines such as triethylamine and triethanolamine and benzoic acid esters such as ethyl 4-dimethylaminobenzoate and 2-(dimethylamino)ethyl benzoate. Further, a titanocene-based photopolymerization initiator, such as Irgacure 784 (manufactured by Ciba Specialty Chemicals), a leuco dye or the like, which initiates radical polymerization in the visible region, may be used in combination as a curing assistant.

The content of the photopolymerization initiator is preferably in the range of 0.01 to 200 parts by mass with respect to 100 parts by mass of the photosensitive prepolymer.

A photopolymerizable vinyl monomer and/or an organic solvent can be used as a diluent in practice of the invention.

Examples of the photopolymerizable vinyl monomers include: glycol mono- or di-acrylates such as ethylene glycol, methoxytetraethylene glycol, polyethylene glycol and propylene glycol; hydroxyalkyl acrylates such as 2-hydroxyethyl acrylate and 2-hydroxybutyl acrylate; acrylamides such as N,N-dimethylacrylamide and N-methylolacrylamide; aminoalkyl acrylates such as N,N-dimethylaminoethyl acrylate; acrylates such as phenoxyacrylate, bisphenol A diacrylate and ethylene oxide or propylene oxide adducts of these phenols; polyvalent alcohols such as hexanediol, trimethylolpropane, pentaerythritol, dipentaerythritol and tris-hydroxyethyl isocyanurate and polyvalent acrylates such as the ethylene oxide or propylene oxide adducts thereof; glycidyl ether acrylates such as glycerol diglycidyl ether, trimethylolpropane triglycidyl ether and triglycidyl isocyanurate; melamine acrylates and/or methacrylates corresponding to the acrylates above; and the like. These photopolymerizable vinyl monomers can be used alone or in combination of two or more.

The content of the photopolymerizable vinyl monomer is preferably in the range of 0.1 to 200 parts by mass with respect to 100 parts by mass of the photosensitive prepolymer.

Examples of the organic solvents include aromatic hydrocarbons such as toluene, xylene and tetramethylbenzene; ketones such as methylethylketone and cyclohexanone; esters such as ethyl acetate, butyl acetate, and acetate esters of the glycol ethers above; alcohols such as ethanol, propanol, ethylene glycol and propylene glycol; glycol ethers such as methylcellosolve, butylcellosolve, methylcarbitol, butylcarbitol, propylene glycol monomethyl ether, dipropylene glycol monoethyl ether and triethylene glycol monoethyl ether; aliphatic hydrocarbons such as octane and decane; petroleum solvents such as petroleum ether, petroleum naphtha, hydrogenated petroleum naphtha and solvent naphtha; and the like. These organic solvents can be used alone or in combination of two or more.

The content of the organic solvent is preferably in the range of 1 to 500 parts by mass with respect to 100 parts by mass of the photosensitive prepolymer.

The photopolymerizable vinyl monomer is used to enhance photopolymerization and also to dilute the photosensitive prepolymer for easier coating. The organic solvent is used to dissolve and dilute the photosensitive prepolymer and thus to apply the mixture as a liquid. Accordingly, an exposure method, either contact method of bringing the film in contact with the photomask or non-contact method, is employed, depending on the kind of the diluent used.

Known polyurethane fine particles can be employed as a polyurethane compound used in practice of the invention. The polyurethane fine particles preferably have a particle diameter of 0.01 to 100 μm.

The polyurethane fine particles can be prepared, for example, by a method of mechanically pulverizing solid-state polyurethane at low temperature, a method of precipitating polyurethane from an aqueous emulsion and drying the precipitate for removal of the solvent, a spray drying method or a method of preparing granular polyurethane by adding a poor solvent to solution-polymerized polyurethane and removing the solvent therefrom by drying. The polyurethane fine particles may be coated with a hydrophobic silica or a fluorine compound-treated silica on the surface.

A polybutadiene compound is used in practice of the invention to make the resulting film flexible. In particular, a polybutadiene containing one or more internal epoxy groups (hereinafter, referred to as "epoxidized polybutadiene"), which easily polymerizes by initiating crosslinking reaction due to the internal epoxy groups, give a cured product superior in flexibility without deterioration in properties such as heat resistance, chemical resistance and electroless gold plating resistance.

The epoxidized polybutadiene is, for example, a polybutadiene having one or more oxirane oxygens bound to the carbons in the polybutadiene main chain. The epoxidized polybutadiene may have one or more epoxy groups as the side-groups and/or end-groups.

The content of the polybutadiene compound is preferably in the range of 0.4 to 60 parts by mass with respect to 100 parts by mass of the photosensitive prepolymer.

The resin composition according to the invention may contain various additives including antifoams, levelling agents, extender pigments such as silica, alumina, barium sulfate, calcium carbonate, calcium sulfate and talc; and pigments such as titanium oxide, azo-base, and phthalocyanine-based pigments.

The resin composition according to the invention may contain photosensitive prepolymers other than the photosensitive prepolymer above. The other photosensitive prepolymer for use is not particularly limited, if it has an unsaturated group and a carboxyl group.

The cured product from the resin composition according to the invention preferably has a modulus of elasticity of 500 to 2000 MPa and an elongation of 5 to 100% at room temperature. When the modulus of elasticity is less than 500 MPa, the resulting cure product may become lower in properties such as solder heat resistance although it is superior in flexibility and thermal shock resistance. On the other hand, when the modulus of elasticity is more than 2000 MPa or the elongation is less than 5%, the cured product may become lower in flexibility and thermal shock resistance.

When a solder resist film is formed on a printed wiring board using the resin composition according to the invention, the resin composition is first adjusted to a viscosity suited for application and coated on a printed wiring board carrying a previously formed circuit pattern by a method such as a screen printing, curtain coating, roll coating or spray coating method, and then dried, as needed, for example, at a temperature in the range of 60° C. to 100° C. to give a film.

Alternatively, the film may be formed, for example, by a method of preparing a dry film of the resin composition and laminating it directly on a printed wiring board. Then, the film is irradiated selectively by an activated light through a photomask having a particular exposure pattern formed thereon. Alternatively, the film may be irradiated and imaged directly according to a pattern with laser beam. Then, the unexposed regions of the film are developed with an aqueous alkaline solution to form a resist pattern. Heat curing, for example, at a temperature in the range of 140° C. to 180° C., accelerates curing reaction of the heat-curing component and polymerization of the photosensitive resin component to give a resist film superior in properties such as heat resistance, solvent resistance, acid resistance, water absorption resistance, PCT (pressure cooker test) resistance, adhesiveness, and electrical properties.

Examples of the aqueous alkaline solutions used in the development include aqueous solution of sodium hydroxide, potassium hydroxide, sodium carbonate, potassium carbonate, sodium phosphate, sodium silicate, ammonia, amines and others. Examples of irradiation light source for photocurable include xenon lamps, low-pressure mercury lamps, medium-pressure mercury lamps, high-pressure mercury lamps, ultrahigh-pressure mercury lamps, metal halide lamps and the like. In addition, laser beam or the like can also be used as the active light.

EXAMPLES

Hereinafter, the present invention will be described specifically with reference to Examples and Comparative Examples, but the invention is not limited thereto. "Parts" in the description below means "parts by mass" entirely, unless specified otherwise.

Preparative Example 1

Tetrahydrophthalic anhydride (0.67 equivalent) was reacted with the reaction product obtained by reaction between a cresol novolak-type epoxy resin having an epoxy equivalent of 217 and containing averagely seven phenol ring residues and an epoxy group in the molecule (1 equivalent) and acrylic acid (1.05 equivalent) by a common method to give a photosensitive prepolymer. The photosensitive prepolymer thus obtained was a viscous liquid containing carbitol acetate in an amount of parts and had an acid value as the mixture of 65 mg-KOH/g.

Main raw materials used in Examples and Comparative Examples are as follows:

(1) Epoxy Compounds or Resins
 1,3,4,6-tetraglycidylglycoluril (product name: TG-G, produced by Shikoku Chemicals Corp., hereinafter referred to as "TG-G")
 2,2'-(3,3',5,5'-tetramethyl(1,1'-biphenyl)-4,4'-diyl)bis(oxymethylene) bis-oxirane (product name: YX-4000, produced by Japan Epoxy Resin, hereinafter referred to as "YX-4000")

(2) Photosensitive Prepolymer
 Photosensitive prepolymer prepared in Preparative Example 1 (hereinafter, referred to as "prepolymer")

(3) Photopolymerization Initiators
 2-Methyl-1-(4-methylthiophenyl)-2-morpholino propan-1-one (product name: Irgacure 907, produced by Chiba Specialty Chemicals Inc., hereinafter referred to as "Irgacure 907")
 2,4-Diethylthioxanthone (product name: DETX-S, produced by Nippon Kayaku Co., Ltd., hereinafter referred to as "DETX-S")

(4) Diluents
 Dipentaerythritol hexaacrylate (hereinafter, referred to as "DPHA")
 Diethylene glycol monoethyl ether acetate (hereinafter, referred to as "carbitol acetate")

(5) Polybutadiene Compounds
 Epoxidized polybutadiene (product name: Epolead PB3600, produced by Daicel Chemical Industries, Ltd., hereinafter referred to as "PB-3600")

(6) Polyurethane Compounds
 Polyurethane fine particles (product name: Dynamic Beads UCN, produced by Dainichiseika Color & Chemicals Mfg. Co., Ltd., hereinafter referred to as "UCN")

(7) Others
 Antifoam (product name: Flowlen AC-300, produced by Kyoeisha Chemical Co., Ltd., hereinafter referred to as "AC-300")
 Phthalocyanine green
 Melamine Example 1

Respective components were mixed and dispersed using a three-roll mill so that they had a composition shown in Table 5 (parts by mass) to give a photocurable/thermosetting resin composition.

Comparative Example 1

A photocurable/thermosetting resin composition having the composition shown in Table 5 was prepared in the same manner as in Example 1 except that TG-G was replaced with YX-4000.

A printed wiring board was prepared by forming a pattern by etching on a copper-clad laminated board of a glass epoxy substrate carrying a 35 μm copper foil. The entire surface of the printed wiring board was coated with each of the resin compositions obtained in Example 1 and Comparative Example 1 by screen printing, and the coated product was dried in a hot air-circulating drier at 80° C. for 30 minutes to give a test sample 1.

Then, a desired negative film was adhered to the test sample 1; ultraviolet ray was irradiated thereon at an intensity of 600 mJ/cm$^2$; the test sample 1 was developed with aqueous 1.0% by weight sodium carbonate solution for 60 seconds and heat cured in a hot air-circulating drier under a condition of 150° C./60 minutes to give a test sample 2 carrying a cured film formed thereon. Test samples 1 and 2 were subjected to the following evaluation tests and the test results are shown in Table 5.

[Solder Heat Resistance]
The test sample 2 was coated with a rosin-based flux and immersed in a solder bath at 260° C. for 10 seconds; the cured film was subjected to a peeling test with cellophane tape and the appearance of the cured film after the test was examined. A test sample without exfoliation was evaluated to be ○ (favorable), while that with exfoliation to be x (unfavorable).

[Acid Resistance]
The test sample 2 was immersed in 10% hydrochloric acid for 30 minutes and the appearance of the cured film was observed visually. A cured film without change was designated as ○ (favorable), while a cured film that was swelled and was exfoliated as x (unfavorable).

[Adhesiveness]

100 grid-shaped cross cuts were formed on the cured film of test sample 2 and exfoliation after peeling test with a cellophane tape was evaluated by visual observation. The test was performed according to the method of JIS D-0202.

[Sensitivity]

A step tablet of Kodak No. 2 was placed on the film of test sample 1, and was exposed to light using an exposure machine equipped with an ultrahigh-pressure mercury lamp under a condition of 600 mJ/cm$^2$. The sensitivity was determined from the number of steps obtained from the step tablet.

[Resolution]

The film of test sample 1 was exposed to light through a negative pattern having lines of 50 to 130 μm, using an exposure machine equipped with an ultrahigh-pressure mercury lamp under a condition of 600 mJ/cm$^2$ and then developed. The line formed with the smallest width was determined for evaluation of the resolution.

[Modulus of Elasticity and Elongation]

The modulus of elasticity (tensile modulus of elasticity) and the elongation (tensile elongation at break) of the test sample above were determined using a tensile-compression tester (manufactured by Shimadzu Corp.).

[Flexibility]

The appearance of the test sample 2 when it was bent by 180° was observed. A test sample without exfoliation was designated as ○ (favorable), while that with exfoliation as x (unfavorable).

[Thermal Degradation Resistance]

The test sample 2 was left at 125° C. for 5 days, and the appearance thereof when it was bent by 180° C. was observed. A test sample without exfoliation was designated as ○, while that with exfoliation as x.

[Thermal Shock Resistance]

The test sample 2 was subjected to 300 cycles of cooling at −65° C. for 30 minutes and heating at 150° C. for 30 minutes and the presence of cracking on the cured film was observed. A test sample without cracking was designated as ○, while that with crack as x.

[Electroless Gold Plating Resistance]

The test sample 2 was plated under the same conditions as those giving a 0.5 μm-thickness nickel layer or a 0.03 μm-thickness gold layer using commercially available electroless nickel- and gold-plating baths and the presence of exfoliation on the cured film after tape peeling test was observed. A test sample without exfoliation was designated as ○, that with slight exfoliation as A, and that with exfoliation as x.

TABLE 5

| Composition (parts by mass) | Example 1 | Comparative Example 1 |
|---|---|---|
| TG-G | 20 | |
| YX-4000 | | 20 |
| Prepolymer | 100 | 100 |
| Irgacure 907 | 15 | 15 |
| DETX-S | 1 | 1 |
| DPHA | 20 | 20 |
| Carbitol acetate | 60 | 60 |
| PB-3600 | 10 | 10 |
| UCN | 30 | 30 |
| AC-300 | 1 | 1 |
| Phthalocyanine green | 0.5 | 0.5 |
| Melamine | 2 | 2 |

TABLE 5-continued

| Evaluation tests | Example 1 | Comparative Example 1 |
|---|---|---|
| Solder heat resistance | ○ | ○ |
| Acid resistance | ○ | ○ |
| Adhesiveness | 100/100 | 100/100 |
| Sensitivity | Step 7 | Step 7 |
| Resolution (μm) | 50 | 50 |
| Modulus of elasticity (Mpa) | 1500 | 1500 |
| Elongation (%) | 10 | 3 |
| Flexibility | ○ | X |
| Thermal degradation resistance | ○ | X |
| Thermal shock resistance | ○ | X |
| Electroless gold plating resistance | ○ | Δ |

The test results shown in Table 5 show that as the photocurable/thermosetting resin composition of the invention comprises the glycidylglycoluril as an epoxy compound, it gives a cured film superior in flexibility and thermal shock resistance without deterioration in basic properties required for solder resist film such as solder heat resistance.

Accordingly, the photocurable/thermosetting resin composition according to the invention is useful for preparation of solder resist films for use on printed wiring boards in various applications.

Third Invention (1) A New Allylglycoluril

The allylglycoluril according to the present invention is represented by General Formula (C0):

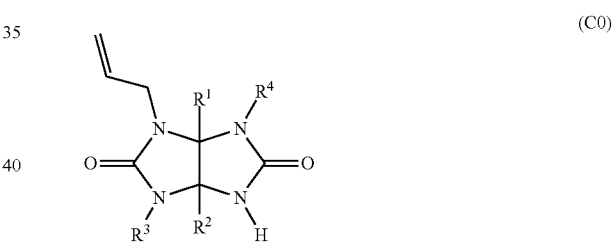

(C0)

wherein R$^1$ and R$^2$ each independently represents a hydrogen atom, a lower alkyl or a phenyl group; and R$^3$ and R$^4$ each independently represents a hydrogen atom or an allyl group.

Thus, the invention provides:

a 1-allylglycoluril represented by the general formula (C0a):

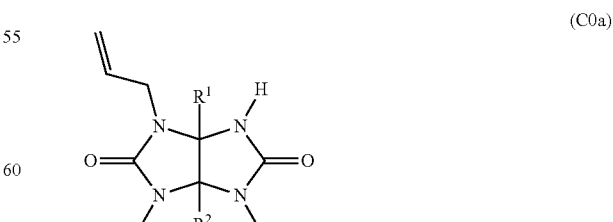

(C0a)

wherein R$^1$ and R$^2$ are the same as those described above;

a 1,3-diallylglycoluril represented by General Formula (C0b):

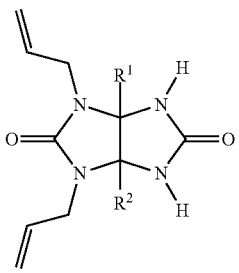

(C0b)

wherein R¹ and R² are the same as those described above);

a 1,4-diallylglycoluril represented by General Formula (C0c):

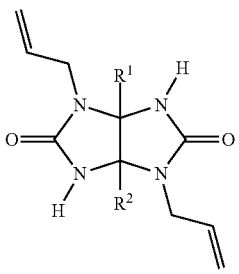

(C0c)

wherein R¹ and R² are the same as those described above);

a 1,4-diallylglycoluril represented by General Formula (C0d):

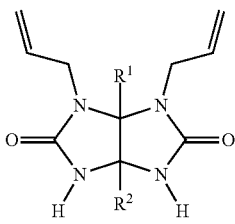

(C0d)

wherein R¹ and R² are the same as those described above); and a 1,3,4-triallylglycoluril represented by (C0e)

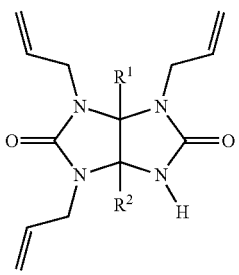

(C0e)

wherein R¹ and R² are the same as those described above.

In the allylglycolurils represented by the general formulae (C0), and (C0a) to (C0e) above, when R¹ or R² is a lower alkyl group, the lower alkyl group is an alkyl group normally having 1 to 5 carbon atoms, preferably 1 to 3, most preferably 1, and the most preferable lower alkyl group is a methyl group.

Accordingly, concrete examples of the preferred allylglycolurils according to the invention include:
1-allylglycoluril,
1,3-diallylglycoluril,
1,4-diallylglycoluril,
1,6-diallylglycoluril,
1,3,4-triallylglycoluril,
1-allyl-3a-methylglycoluril,
1,3-diallyl-3a-methylglycoluril,
1,4-diallyl-3a-methylglycoluril,
1,6-diallyl-3a-methylglycoluril,
1,3,4-triallyl-3a-methylglycoluril,
1-allyl-3a,6a-dimethylglycoluril,
1,3-diallyl-3a,6a-dimethylglycoluril,
1,4-diallyl-3a,6a-dimethylglycoluril,
1,6-diallyl-3a,6a-dimethylglycoluril,
1,3,4-triallyl-3a,6a-dimethylglycoluril,
1-allyl-3a,6a-diphenylglycoluril,
1,3-diallyl-3a,6a-diphenylglycoluril,
1,4-diallyl-3a,6a-diphenylglycoluril,
1,6-diallyl-3a,6a-diphenylglycoluril,
1,3,4-triallyl-3a,6a-diphenylglycoluril and the like.

The allylglycolurils represented by the general formulae (C0a) to (C0e) above is normally prepared in the following first and second processes.

1-Allylglycoluril is prepared by reacting urea with glyoxal normally in water in the presence of a base catalyst in the first process and then by reacting the reaction product thus obtained with allylurea normally in water in the presence of an acid catalyst in the second process.

Among the diallylglycolurils above, for example, 1,3-diallylglycoluril is obtained by reacting urea with glyoxal normally in water in the presence of a base catalyst in the first process and then by reacting the reaction product thus obtained with a diallylurea normally in water in the presence of an acid catalyst in the second process.

Among the triallylglycolurils above, for example, 1,3,4-triallylglycoluril is obtained by reacting allylurea with glyoxal normally in water in the presence of a base catalyst in the first process and then reacting the reaction product thus obtained with a diallylurea normally in water in the presence of an acid catalyst in the second process.

In synthesis of any one of 1-allylglycoluril, 1,3-diallylglycoluril and 1,3,4-triallylglycoluril above, glyoxal is used in the first process normally in an amount of in the range of 0.5 to 2.0 mole parts, and preferably in the range of 0.8 to 1.5 mole parts, with respect to 1 mole part of urea or allylurea.

Examples of the base catalysts used in the first process include hydroxides such as sodium hydroxide and potassium hydroxide and carbonate salts such as sodium carbonate and potassium carbonate. The base catalyst is normally used in an amount in the range of 0.1 to 1.0 mole part with respect to 1 mole part of urea or allylurea.

The solvent used in the first process is not particularly limited, if it does not inhibit the reaction when used. Examples thereof include water, alcohols such as methanol, ethanol and isopropyl alcohol; aliphatic hydrocarbons such as hexane and heptane; ketones such as acetone and 2-butanone; esters such as ethyl acetate and butyl acetate; aromatic hydrocarbons such as benzene, toluene and xylene; halogenated hydrocarbons such as methylene chloride, chloroform, carbon tetrachloride, chlorotrifluoromethane, dichloroethane, chlorobenzene and dichlorobenzene; ethers such as diethyl ether, diisopropyl ether, tetrahydrofuran, dioxane, dimethoxyethane and diethylene glycol dimethyl ether; amides such as formamide, N,N-dimethylformamide, N,N-dimethylacetamide, N-methyl-2-pyrrolidone, N-methylpyrrolidinone and hexamethylphosphorotriamide; sulfoxides such as dimethylsulfoxide and the like. These solvents may be used alone or in combination of two or more in an appropriate amount.

The reaction temperature in the first process is normally in the range of −10° C. to 150° C., and preferably in the range of 0° C. to 100° C. The reaction time varies according to the reaction temperature, but is normally in the range of 1 to 24 hours, and preferably in the range of 1 to 6 hours.

After completion of the first process, the reaction product may be concentrated by removing excess glyoxal and the solvent by distillation and the concentrate may be used in the second process. Alternatively, after completion of the first process, the reaction mixture obtained may be supplied to the second process as it is.

In the second process, allylurea or diallylurea is used normally in an amount in the range of 0.5 to 2.0 mole parts, and preferably in the range of 0.8 to 1.5 mole parts with respect to 1 mole part of urea or allylurea used in the first process.

Examples of the acid catalysts used in the second process include sulfuric acid, hydrochloric acid, nitric acid, acetic acid, formic acid and the like. These acid catalysts may be used alone or in combination of two or more. The acid catalyst is normally used in an amount in the range of 0.1 to 100 mole parts with respect to 1 mole part of urea or allylurea used in the first process.

Also in the second process, the solvent is not particularly limited, if it does not inhibit the reaction when used and the solvents identical with those used in the first process can be used.

The reaction temperature in the second process is normally in the range of −10° C. to 200° C., and preferably in the range of 0° C. to 150° C. The reaction time varies according to the reaction temperature, but is normally in the range of 1 to 24 hours, and preferably in the range of 1 to 12 hours.

After completion of the second process, the allylglycoluril generated can be isolated from the reaction mixture obtained, for example, by extraction operation. If needed, the allylglycoluril obtained may be purified additionally, for example, by washing with a solvent such as water or by activated carbon treatment or silica gel chromatography.

EXAMPLES

Hereinafter, the present invention will be described with reference to Examples but it should be understood that the present invention is not particularly restricted by these Examples.

In the following Examples, urea, allylurea and aqueous 40% glyoxal solution used were products of Tokyo Chemical Industry Co., Ltd. and diallylurea was a product of Sigma-Aldrich Co. LLC.

Example 1

Synthesis of 1-allylglycoluril

Urea (3.00 g, 50.0 mmol) and aqueous 40% glyoxal solution (8.71 g, 60.0 mmol) were placed in a 100 mL flask equipped with a thermometer. Two drops of aqueous 40% sodium hydroxide solution was added to the mixture obtained at room temperature, and the mixture was stirred at 80° C. for 1 hour. The reaction mixture obtained was then concentrated under reduced pressure. Allylurea (5.01 g, 50.0 mmol), acetic acid (50 mL) and sulfuric acid (490 mg, 5.0 mmol) were added to the concentrate obtained and the mixture was stirred at 110° C. overnight. After the reaction mixture obtained was cooled to room temperature, acetone (50 mL) was added thereto, and the oil generated was separated and dried to give 1-allylglycoluril (1.86 g) as a white viscous oil (yield: 20%).

Figure 8:
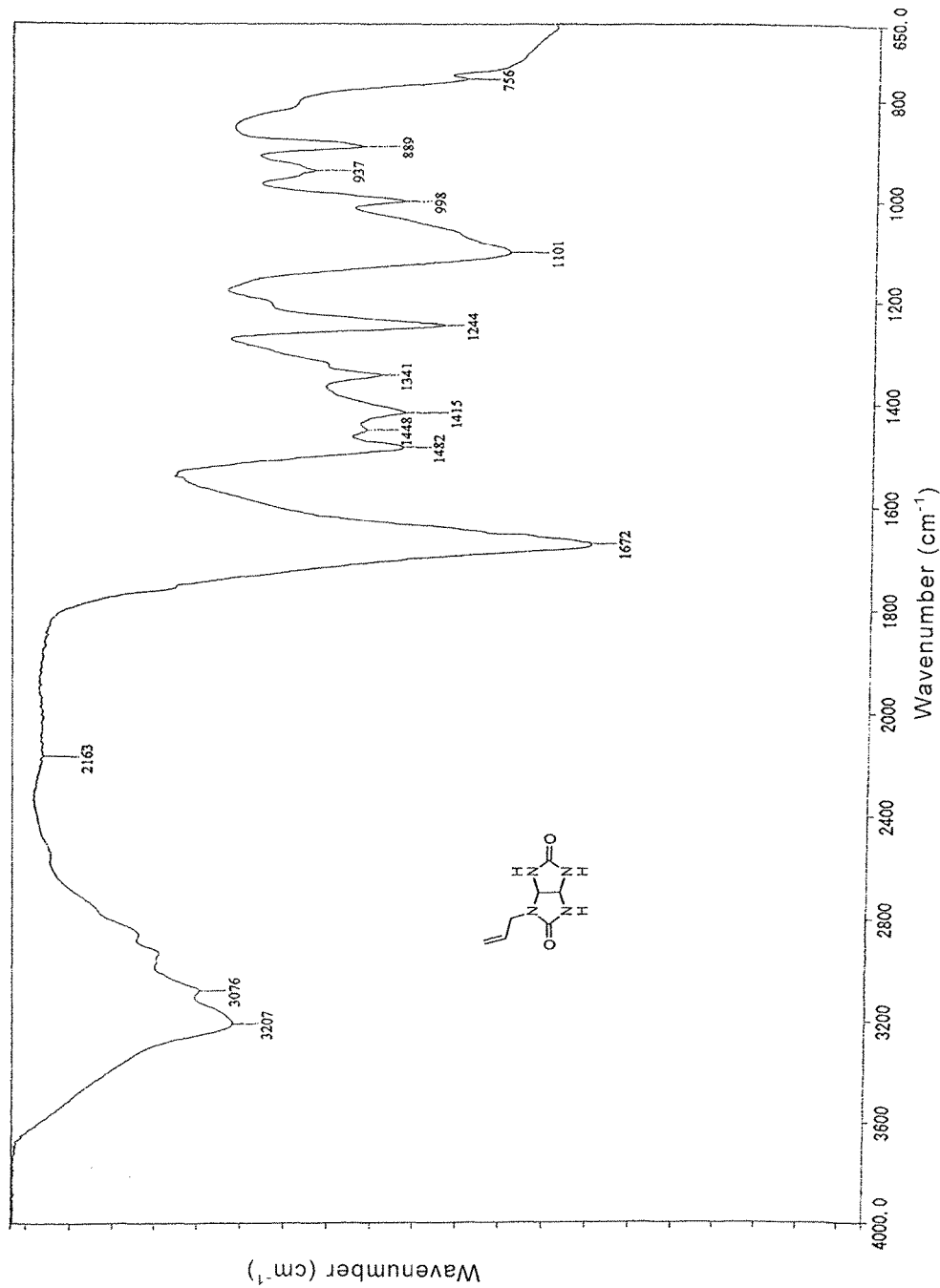
FIG. 8 shows an IR spectrum of 1-allylglycoluril.

The IR spectrum of the 1-allylglycoluril obtained is shown in FIG. 8. The δ values of the $^1$H-NMR spectrum (d6-DMSO) were as follows:

7.41 (s, 1H), 7.37 (s, 1H), 7.28 (s, 1H), 5.62-5.79 (m, 1H), 5.08-5.28 (m, 4H), 3.86-3.94 (m, 1H), 3.44 (dd, 1H)

Example 2

Synthesis of 1,3-diallylglycoluril

Urea (3.00 g, 50.0 mmol) and aqueous 40% glyoxal solution (8.71 g, 60.0 mmol) were placed in a 100 mL flask equipped with a thermometer. Two drops of aqueous 40% sodium hydroxide solution was added to the mixture obtained at room temperature and the mixture was stirred at 80° C. for 1 hour. The reaction mixture obtained was then concentrated under reduced pressure. Diallylurea (7.00 g, 50.0 mmol), acetic acid (50 mL) and sulfuric acid (490 mg, 5.0 mmol) were added to the concentrate obtained and the mixture was stirred at 110° C. overnight. After the reaction mixture obtained was cooled to room temperature, acetone (50 mL) was added thereto, and the oil generated was separated and dried to give 1,3-diallylglycoluril (4.28 g) as a white viscous oil (yield: 39%).

Figure 9:
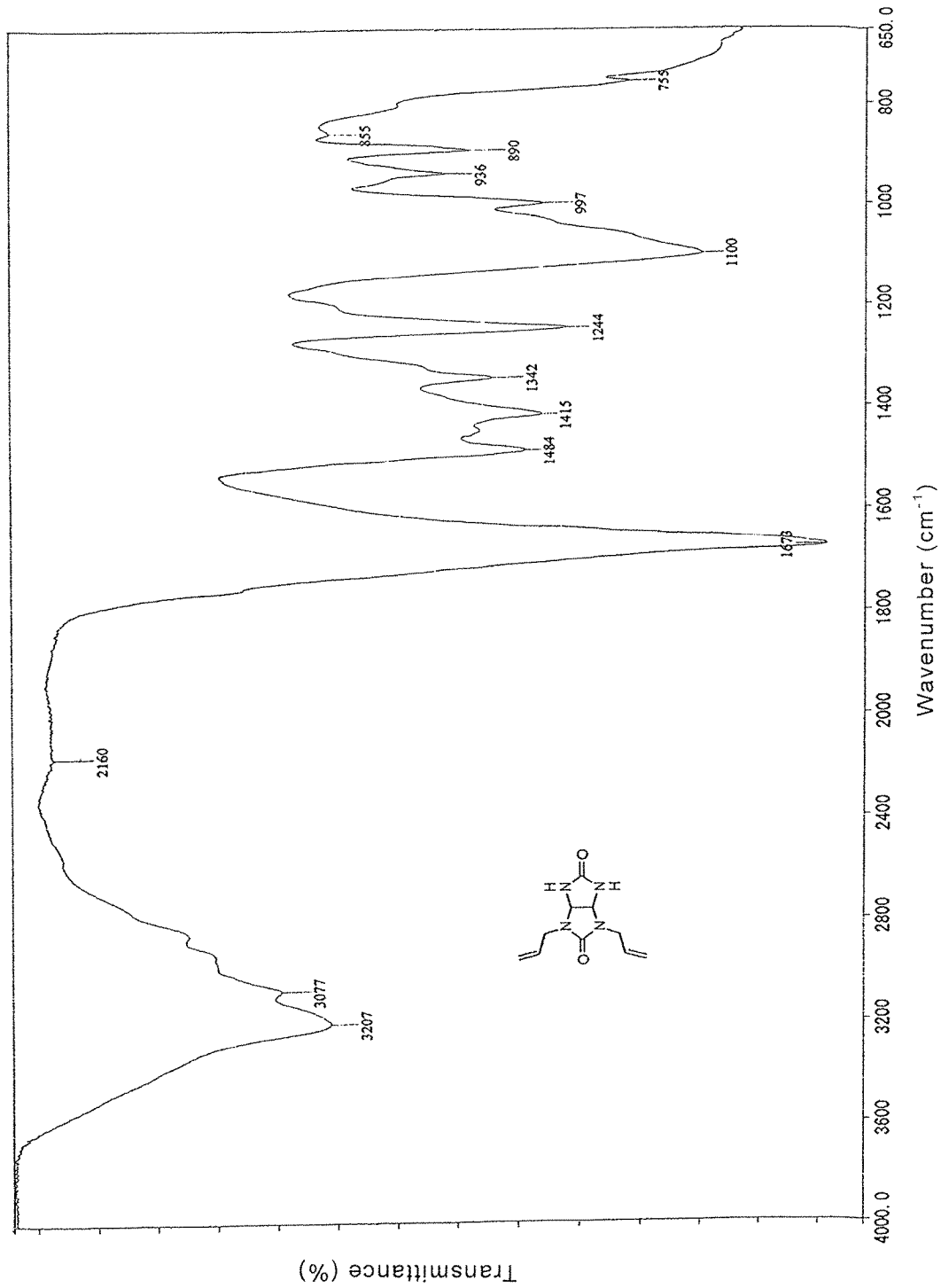
FIG. 9 shows an IR spectrum of 1,3-diallylglycoluril.

The IR spectrum of the 1,3-diallylglycoluril obtained is shown in FIG. 9. The δ values of the $^1$H-NMR spectrum (d6-DMSO) were as follows:

7.52 (s, 2H), 5.69-5.84 (m, 2H), 5.08-5.23 (m, 6H), 3.92-3.97 (m, 2H), 3.52 (dd, 2H)

Example 3

Synthesis of 1,3,4-triallylglycoluril

Allylurea (3.00 g, 30.0 mmol) and aqueous 40% glyoxal solution (5.22 g, 36.0 mmol) were placed in a 100 mL flask equipped with a thermometer. Two drops of aqueous 40% sodium hydroxide solution was added to the mixture obtained at room temperature and the mixture was stirred at 80° C. for 1 hour. The reaction mixture obtained was then concentrated under reduced pressure. Diallylurea (4.21 g, 30.0 mmol), acetic acid (30 mL) and sulfuric acid (294 mg, 3.0 mmol) were added to the concentrate obtained and the mixture was stirred at 110° C. overnight. After the reaction mixture obtained was cooled to room temperature, chloroform (30 mL) was added thereto and the mixture was allowed to separate. The organic layer obtained was washed with water (30 mL) and concentrated under reduced pressure to give 1,3,4-triallylglycoluril (6.80 g) as a pale yellow oil (yield: 87%).

Figure 10:
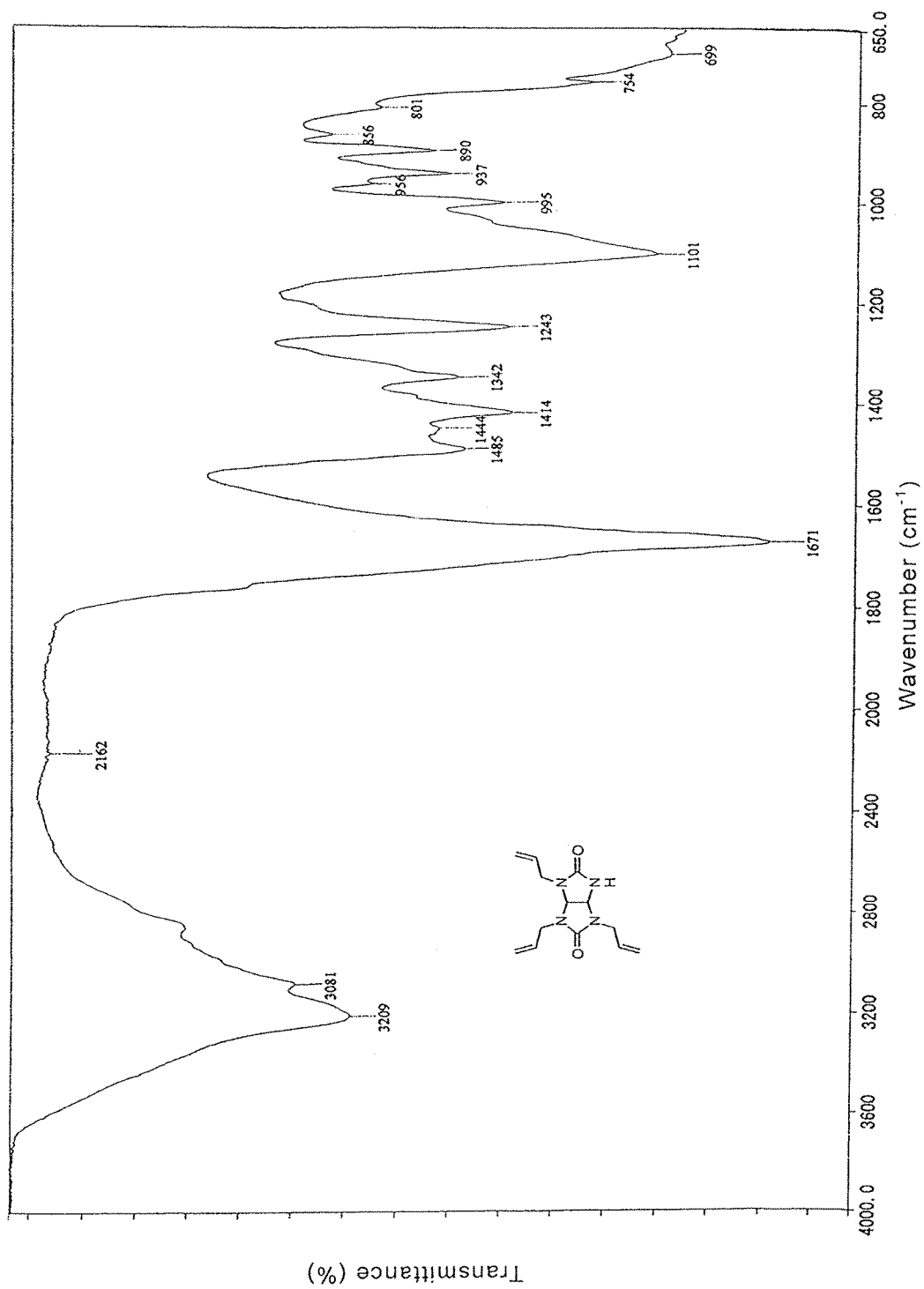
FIG. 10 shows an IR spectrum of 1,3,4-triallylglycoluril.

The IR spectrum of the 1,3,4-triallylglycoluril obtained is shown in FIG. 10. The δ values of the $^1$H-NMR spectrum (d6-DMSO) were as follows:

6.22 (br, 1H), 5.72-5.83 (m, 3H), 5.16-5.32 (m, 8H), 4.11-4.26 (m, 2H), 4.00-4.06 (m, 1H), 3.68-3.85 (m, 3H)

(2) Olefinic Resin Composition

The olefinic resin composition according to the invention comprises the allylglycoluril represented by the general formula (C) above and an olefinic polymer.

The olefinic polymer used in the olefinic resin composition according to the invention refers to a polymer of olefin monomers, a polymer of polar monomers, a copolymer of an olefin monomer and a polar monomer or the like.

Examples of the olefin monomers include α-olefin compounds having 2 to 20 carbon atoms such as ethylene, propylene, 1-butene, 1-pentene, 1-hexene, 3-methyl-1-butene, 3-methyl-1-pentene, 3-ethyl-1-pentene, 4-methyl-1-pentene, 4,4-dimethyl-1-pentene, 4-methyl-1-hexene, 4,4-dimethyl-1-hexene, 4-ethyl-1-hexene, 3-ethyl-1-hexene, 1-octene, 1-decene, 1-dodecene, 1-tetradecene, 1-hexadecene, 1-octadecene and 1-eicosene; cyclic olefin compounds having 3 to 20 carbon atoms such as cyclopentene, cycloheptene, 2-norbornene, 5-methyl-2-norbornene, 5,6-dimethyl-2-norbornene, 5-ethyl-2-norbornene, 5-butyl-2-norbornene, 5-ethylidene-2-norbornene, 5-methoxycarbonyl-2-norbornene, 5-cyano-2-norbornene, 5-methyl-5-methoxycarbonyl-2-norbornene, 5-hexyl-2-norbornene, 5-octyl-2-norbornene, 5-octadecyl-2-norbornene, tetracyclododecene, 1,4:5,8-dimethano-1,2,3,4,4a,5,8,8a-2,3-cyclopentadienonaphthalene, 6-methyl-1,4:5,8-dimethano-1,4,4a,5,6,7,8,8a-octahydronaphthalene, and 1,4:5,10:6,9-trimethano-1,2,3,4,4a,5,5a,6,9,9a,10,10a-dodecahydro-2,3-cyclopentadienoanthracene; aromatic vinyl compounds such as styrene, substituted styrenes, allylbenzene, substituted allylbenzenes, vinylnaphthalenes, substituted vinylnaphthalenes, allylnaphthalenes and substituted allylnaphthalenes; alicyclic vinyl compounds such as vinylcyclopentane, substituted vinylcyclopentanes, vinylcyclohexane, substituted vinylcyclohexanes, vinylcycloheptane, substituted vinylcycloheptanes and allyl norbornanes; silane-based unsaturated compounds such as allyltrimethylsilane, allyltriethylsilane, 4-trimethylsilyl-1-butene, 6-trimethylsilyl-1-hexene, 8-trimethylsilyl-1-octene and 10-trimethylsilyl-1-decene; conjugated or non-conjugated diene compounds such as butadiene, 1,4-hexadiene, 7-methyl-1,6-octadiene, 1,8-nonadiene, 1,9-decadiene, norbornadiene and dicyclopentadiene; and the like.

Examples of the polar monomers include α,β-unsaturated carboxylic acids such as acrylic acid, methacrylic acid, fumaric acid, maleic anhydride, itaconic acid, itaconic anhydride and bicyclo[2.2.1]-5-heptene-2,3-dicarboxylic acid and the metal salt compounds thereof such as of sodium, potassium, lithium, zinc, magnesium and calcium; a,6-unsaturated carboxylic ester compounds such as methyl acrylate, ethyl acrylate, n-propyl acrylate, isopropyl acrylate, n-butyl acrylate, isobutyl acrylate, t-butyl acrylate, 2-ethylhexyl acrylate, methyl methacrylate, ethyl methacrylate, n-propyl methacrylate, isopropyl methacrylate, n-butyl methacrylate and isobutyl methacrylate; unsaturated dicarboxylic acids such as maleic acid and itaconic acid; vinyl ester compounds such as vinyl acetate, vinyl propionate, vinyl caproate, vinyl caprate, vinyl laurate, vinyl stearate, and vinyl trifluoroacetate; unsaturated glycidyl group-containing monomers such as glycidyl acrylate, glycidyl methacrylate and monoglycidyl itaconate; and the like.

In practice of the invention, these olefinic polymers exemplified may be used alone or in combination of two or more.

In practice of the invention, the allylglycoluril represented by the general formula (C) above is used as a crosslink assistant.

In the allylglycoluril represented by the general formula (C) above, when both $R^1$ and $R^2$ are lower alkyl groups, the number of carbons therein is preferably 1 to 3, and more preferably 1. Thus, $R^1$ and $R^2$ are more preferably both methyl groups.

Examples of the allylglycolurils include:
1-allylglycoluril,
1,3-diallylglycoluril,
1,4-diallylglycoluril,
1,6-diallylglycoluril,
1,3,4-triallylglycoluril,
1,3,4,6-tetraallylglycoluril,
1-allyl-3a-methylglycoluril,
1,3-diallyl-3a-methylglycoluril,
1,4-diallyl-3a-methylglycoluril,
1,6-diallyl-3a-methylglycoluril,
1,3,4-triallyl-3a-methylglycoluril,
1,3,4,6-tetraallyl-3a-methylglycoluril,
1-allyl-3a,6a-dimethylglycoluril,
1,3-diallyl-3a,6a-dimethylglycoluril,
1,4-diallyl-3a,6a-dimethylglycoluril,
1,6-diallyl-3a,6a-dimethylglycoluril,
1,3,4-triallyl-3a,6a-dimethylglycoluril,
1,3,4,6-tetraallyl-3a,6a-dimethylglycoluril,
1-allyl-3a,6a-diphenylglycoluril,
1,3-diallyl-3a,6a-diphenylglycoluril,
1,4-diallyl-3a,6a-diphenylglycoluril,
1,6-diallyl-3a,6a-diphenylglycoluril,
1,3,4-triallyl-3a,6a-diphenylglycoluril,
1,3,4,6-tetraallyl-3a,6a-diphenylglycoluril and the like.

Unsaturated compounds having an allyl or (meth)acryloxy group, or the like may be used as other crosslink assistants in the range that does not impair the advantageous effects of the present invention.

Examples of the unsaturated compounds include polyallyl compounds such as triallyl isocyanurate, triallyl cyanurate, diallylglycidyl isocyanurate, diallyl phthalate, diallyl fumarate and diallyl maleate; poly(meth)acryloxy compounds such as ethylene glycol diacrylate, ethylene glycol dimethacrylate and trimethylolpropane trimethacrylate; divinylbenzene and the like.

In practice of the invention, the crosslink assistant is preferably blended in an amount of 0.1 to 100 parts by mass, and more preferably 1 to 30 parts by mass, with respect to 100 parts by mass of the olefinic polymer.

The olefinic resin composition according to the invention is crosslinked by heating in the presence of a peroxide, or by irradiating with an active energy ray.

The temperature when the olefinic resin composition is heated in the presence of a peroxide is not particularly limited, but it is preferably in the range of 50° C. to 300° C.

The heating time may be determined appropriately according to the heating temperature, the peroxide and the crosslink assistant used, or according to the amounts thereof.

Examples of the peroxides include: peroxyketal compounds such as
1,1-bis(t-butylperoxy)-3,3,5-trimethylcyclohexane,
1,1-bis(t-hexylperoxy)-3,3,5-trimethylcyclohexane,
1,1-bis(t-hexylperoxy)cyclohexane,
1,1-bis(t-butylperoxy)cyclododecane,
1,1-bis(t-butylperoxy)cyclohexane,
2,2-bis(t-butylperoxy)octane,
n-butyl-4,4-bis(t-butylperoxy)butane and
n-butyl 4,4-bis(t-butylperoxy)valerate;
dialkyl peroxide compounds such as di-t-butyl peroxide,
dicumyl peroxide,
t-butyl cumyl peroxide, α,α'-bis(t-butylperoxy-m-isopropyl)benzene,
α,α'-bis(t-butylperoxy)diisopropylbenzene,
2,5-dimethyl-2,5-bis(t-butylperoxy)hexane and
2,5-dimethyl-2,5-bis(t-butylperoxy)hexyne-3;
diacyl peroxide compounds such as acetyl peroxide,
isobutyryl peroxide,
octanoyl peroxide,
decanoyl peroxide,
lauroyl peroxide,
3,5,5-trimethylhexanoyl peroxide,
benzoyl peroxide,
2,4-dichlorobenzoyl peroxide and
m-toluoyl peroxide;
peroxyester compounds such as t-butyl peroxyacetate,
t-butyl peroxyisobutyrate,
t-butylperoxy-2-ethyl hexanoate,
t-butyl peroxylaurate,
t-butyl peroxybenzoate,
di-t-butyl peroxyisophthalate,
2,5-dimethyl-2,5-di(benzoylperoxy)hexane,
t-butylperoxymaleic acid,
t-butylperoxyisopropyl carbonate and
cumyl peroxyoctanoate;
hydroperoxide compounds such as t-butyl hydroperoxide,
cumene hydroperoxide,
diisopropylbenzene hydroperoxide,
2,5-dimethylhexane-2,5-dihydroperoxide and
1,1,3,3-tetramethylbutyl peroxide; and the like. The peroxide is preferably blended in an amount of 0.1 to 5 parts by mass with respect to 100 parts by mass of the olefinic polymer.

The peroxide exemplified above may be used alone or in combination of two or more.

The active energy ray is, for example, a particle beam or an electromagnetic wave; the particle beam is, for example, electron beam (EB) or alpha ray; and the electromagnetic wave is, for example, ultraviolet ray (UV), visible ray, infrared ray, γ ray or X ray.

In particular, electron beam or ultraviolet ray is used preferably as the active energy ray.

These active energy rays are irradiated using a known apparatus. The accelerating voltage of the electron beam when used is preferably in the range of 0.1 to 10 MeV and the irradiation dose in the range of 1 to 500 kGy. When ultraviolet ray is used, a lamp having a radiation wavelength of 200 to 450 nm is used as the light source.

In the case of electron beam, the light source is, for example, tungsten filament; in the case of ultraviolet ray, the light source is, for example, low-pressure mercury lamp, high-pressure mercury lamp, ultraviolet ray-emitting mercury lamp, carbon arc lamp, xenon lamp, zirconium lamp, or the like.

When ultraviolet ray is used as the active energy ray, the olefinic resin composition may further comprises a photopolymerization initiator. Examples of the photopolymerization initiators include: acetophenones such as 2-hydroxy-2-methyl-1-phenylpropan-1-one, 1-hydroxycyclohexyl phenyl ketone and 2-methyl-1-[4-(methylthio)phenyl]-2-morpholinopropan-1-one; benzoins such as benzyldimethyl ketal; benzophenones such as benzophenone, 4-phenylbenzophenone and hydroxybenzophenone; thioxanthones such as isopropylthioxanthone and 2,4-diethylthioxanthone; methyl phenylglyoxylate and the like.

These photopolymerization initiators exemplified may be used alone or in combination of two or more. When the olefinic resin composition comprises a photopolymerization initiator, the amount of the photopolymerization initiator is preferably in the range of 0.01 to 5 parts by mass with respect to 100 parts by mass of the olefinic polymer.

As needed, a known photopolymerization accelerator, for example a benzoic acid derivative such as 4-dimethylaminobenzoic acid or a tertiary amine, may be used in combination.

The olefinic resin composition according to the invention may comprise a silane-coupling agent for improvement of the adhesiveness when the resin composition is integrated with a material of different composition Examples of the silane-coupling agents include: γ-chloropropylmethoxysilane, vinylethoxysilane, vinyltris(6-methoxyethoxy)silane, γ-methacryloxypropyltrimethoxysilane, vinyl triacetoxysilane, γ-glycidoxypropyltrimethoxysilane, γ-glycidoxypropyltriethoxysilane, (3,4-epoxycyclohexyl)ethyltrimethoxysilane, vinyltrichlorosilane, γ-mercaptopropyltrimethoxysilane, γ-aminopropyltriethoxysilane, N-8-(aminoethyl)-γ-aminopropyltrimethoxysilane and the like.

These silane-coupling agents exemplified above may be used alone or in combination of two or more, and are preferably blended in an amount of 0.1 to 5 parts by mass with respect to 100 parts by mass of the olefinic copolymer.

The olefinic resin composition of the invention may comprise an antioxidant, a photostabilizer (ultraviolet absorbent) or the like for prevention of the degradation caused by ultraviolet ray in sunlight.

Among the antioxidants above, examples of the phenol-based antioxidants include:
monophenol compounds such as 2,6-di-t-butyl-p-cresol, butylated hydroxyanisoles, 2,6-di-t-butyl-p-ethylphenol and stearyl-B-(3,5-di-t-butyl-4-hydroxyphenyl)propionate; bisphenol compounds such as 2,2'-methylene-bis(4-methyl-6-t-butylphenol), 2,2'-methylene-bis(4-ethyl-6-t-butylphenol), 4,4'-thiobis(3-methyl-6-t-butylphenol), 4,4'-butylidene-bis(3-methyl-6-t-butylphenol) and 3,9-bis{1,1-dimethyl-2-[β-(3-t-butyl-4-hydroxy-5-methylphenyl)propionyloxy]ethyl}2,4,8,10-tetraoxaspiro[5.5]undecane; and polymeric phenol compounds such as 1,1,3-tris(2-methyl-4-hydroxy-5-t-butylphenyl)butane, 1,3,5-trimethyl-2,4,6-tris(3,5-di-t-butyl-4-hydroxybenzyl)benzene, tetrakis-[methylene-3-(3', 5'-di-t-butyl-4'-hydroxyphenyl)propionate]methane, bis[3,3'-bis-(4'-hydroxy-3'-t-butylphenyl)butylic acid]glycol ester, 1,3,5-tris(3',5'-di-t-butyl-4'-hydroxybenzyl)-S-triazin-2,4,6-(1H,3H,5H)-trione and tocophenol.

Among the antioxidants, examples of the phosphorus-based antioxidants include: phosphite compounds such as triphenyl phosphite, diphenyl isodecyl phosphite, phenyl diisodecyl phosphite, tris(nonylphenyl) phosphite, diisodecyl pentaerythritol phosphite, tris(2,4-di-t-butylphenyl) phosphite, cyclic neopentanetetrayl bis(octadecyl) phosphite, cyclic neopentanetetrayl bi(2,4-di-t-butylphenyl) phosphite, cyclic neopentanetetrayl bi(2,4-di-t-butyl-4-methylphenyl) phosphite and bis{2-t-butyl-6-methyl-4-[2-(octadecyloxycarbonyl)ethyl]phenyl}hydrogen phosphite; and oxaphosphaphenanthrene oxide compounds such as 9,10-dihydro-9-oxa-10-phosphaphenanthrene-10-oxide, 10-(3,5-di-t-butyl-4-hydroxybenzyl)-9,10-dihydro-9-oxa-10-phosphaphenanthrene-10-oxide and 10-decyloxy-9,10-dihydro-9-oxa-10-phosphaphenanthrene-10-oxide.

Examples of the photostabilizers include salicylic acid compounds such as phenyl salicylate, p-t-butylphenyl salicylate and p-octylphenyl salicylate;
benzophenone compounds such as 2,4-dihydroxybenzophenone,
2-hydroxy-4-methoxybenzophenone, 2-hydroxy-4-octoxybenzophenone, 2-hydroxy-4-dodecyloxybenzophenone,
2,2'-dihydroxy-4-methoxybenzophenone,
2,2'-dihydroxy-4,4'-dimethoxybenzophenone and
2-hydroxy-4-methoxy-5-sulfo benzophenone;
benzotriazole compounds such as
2-(2'-hydroxy-5'-methylphenyl)benzotriazole,
2-(2'-hydroxy-5'-t-butylphenyl)benzotriazole,
2-(2'-hydroxy-3',5'-di-t-butylphenyl)benzotriazole,
2-(2'-hydroxy-3'-t-butyl-5'-methylphenyl)-5-chlorobenzotriazole,
2-(2'-hydroxy-3',5'-di-t-butylphenyl)-5-chlorobenzotriazole,
2-(2'-hydroxy-3',5'-di-t-amylphenyl)benzotriazole and
2-[(2'-hydroxy-3',3'',4'',5'',6''-tetrahydrophthalimidomethyl)-5'-methylphenyl]benzotriazole; and hindered amine compounds such as bis(2,2,6,6-tetramethyl-4-piperidyl) sebacate, bis(1,2,2,6,6-pentamethyl-4-piperidyl) sebacate and bis(1,2,2,6,6-pentamethyl-4-piperidyl)[{3,5-bis(1,1-dimethylethyl)-4-hydroxyphenyl}methyl]butyl malonate.

The olefinic resin composition comprises the antioxidants and photostabilizers respectively preferably each in an amount of 0.1 to 3 parts by mass with respect to 100 parts by mass of the olefinic polymer.

In addition to the additives above, for example, a fatty acid metal salt such as cadmium or barium salt may be blended to the olefinic resin composition according to the invention, as a discoloration inhibitor. Alternatively, for example, a pigment, a dye or an inorganic filler may be blended for coloring. Examples thereof include white pigments such as titanium oxide and calcium carbonate; blue pigments such as ultramarine, black pigments such as carbon black, glass beads, light diffusing agents and the like.

These additives are preferably added respectively in an amount of 0.5 to 50 parts by mass with respect to 100 parts by mass of the olefinic polymer.

The olefinic resin composition according to the invention is prepared by wet-, dry- or melt-mixing an olefinic polymer and the allylglycoluryl represented by the general formula (C) above, as needed with a peroxide, a photopolymerization initiator and any other components, as needed, under nitrogen environment at a suitable temperature using, for example, a tank mixer, a high-speed stirrer, a tight-sealed kneader, an internal mixer, an uniaxial extruder or a twin screw extruder.

When the olefinic resin composition according to the invention is crosslinked with a peroxide, it can be crosslinked during the melt mixing described above.

The olefinic resin composition according to the invention, is used favorably as a raw material for use in producing molded products in various shapes such as films, sheets and cases (containers) by a known molding method.

Examples of the known molding methods include inflation molding, T die molding, tubular draw molding, tenter draw molding, extrusion lamination molding, dry lamination molding, calendering molding, bank molding, injection molding, compression molding, injection compression molding, air-pressure forming, vacuum molding, pipe molding, atypical extrusion molding, hollow molding, injection hollow molding, injection draw hollow molding and the like.

When the olefinic resin composition according to the present invention is crosslinked with a peroxide, it can be also crosslinked during molding by these molding methods.

Alternatively, when the olefinic resin composition according to the invention is crosslinked by irradiation of active energy ray, it can be also crosslinked by irradiation simultaneously (in-line method) with or after the molding by these molding methods.

The olefinic resin composition according to the invention is suitably used in applications such as various rubber materials for automobiles such as packing and sealing materials, materials for sealing solar cells (EVA), insulating sheaths and adhesives for electric and electronic devices and parts, materials for covering electric wires, adhesives, corrosion protection materials and paints for laminated boards, structural composite materials and, civil engineering and construction materials, various molded electronic parts, such as switches, relays, transformers, coil bobbins and connectors, for which a heat resistance not causing melt deformation during soldering is required, LED sealing materials, various plastic materials for optical materials such as reflectors and lenses, automobile, electric and electronic parts, and the like.

The olefinic resin composition of the invention is also suitably used as a material for engineering plastics such as polybutylene terephthalate resins, i.e., for crystalline thermoplastic polyester resins superior in mechanical properties, electrical properties and others physical-chemical properties and also superior in processability.

EXAMPLES

Hereinafter, the present invention will be described specifically with reference to Examples and Comparative Examples, but the invention is not limited thereto. Methods for determining haze value and total light transmittance will be described below.

[Measurement of Haze Value and Total Light Transmittance]

A test sample sheet is placed between two blue glasses having a thickness of 3 mm; the composite was bonded together by pressurizing in a vacuum bonding machine at 150° C. for 15 minutes; and the haze value and the total light transmittance thereof were determined according to JIS K7105.

Example 1

An olefinic polymer, ethylene-vinyl acetate copolymer (vinyl acetate content: 25%, melt index: 4, 100 parts by mass), dicumyl peroxide (1 parts by mass), a crosslink assistant, 1,3,4,6-tetraallylglycoluril (5 parts by mass), and a silane-coupling agent, γ-methacryloxypropyl-trimethoxysilane (0.3 part by mass) were mixed to give an olefinic resin composition.

A test sample sheet having a thickness of 0.5 mm was prepared from the resin composition using a profile extruder at a processing temperature of 100° C.

The haze value and the total light transmittance of the sheet obtained were determined and shown in Table 6.

Examples 2 to 6 and Comparative Examples 1 to 2

Sheets having the composition shown in Table 6 were prepared in the same manner as in Example 1, and the haze value and the total light transmittance thereof were determined. The results are shown in Table 6.

TABLE 6

|  | Examples | | | | | | Comparative Examples | |
| --- | --- | --- | --- | --- | --- | --- | --- | --- |
|  | 1 | 2 | 3 | 4 | 5 | 6 | 1 | 2 |
| Composition (parts by mass) | | | | | | | | |
| Ethylene-vinyl acetate copolymer | 100 | 100 | 100 | 100 | 100 | 100 | 100 | 100 |
| Dicumyl peroxide | 1 | 1 | 1 | 1 | 1 | 1 | 1 | 1 |
| 1,3,4,6-Tetraallylglycoluril | 0 | 3 | 3 | | | | | |
| 1,3,4,6-Tetraalyl-3a,6a-dimethylglycoluril | | | | 5 | 3 | 3 | | |
| Triallyl isocyanurate | | | 2 | | | 2 | 5 | |
| γ-Methacryloxypropyltrimethoxysilane | 0.3 | 0.3 | 0.3 | 0.3 | 0.3 | 0.3 | 0.3 | 0.3 |
| Evaluation tests | | | | | | | | |
| Haze value (%) | 0.5 | 0.5 | 0.55 | 0.5 | 0.5 | 0.55 | 0.6 | 0.8 |
| Total light transmittance (%) | 93 | 92 | 91 | 92 | 91 | 91 | 90 | 88 |

(3) A Curable Composition Superior in Adhesiveness

The curable composition superior in adhesiveness according to the invention comprises:
(A) an alkenyl group-containing organic compound,
(B) a compound having at least three or more hydrosilyl groups in the molecule, and
(C) a hydrosilylation catalyst,
wherein the component (A) comprises a tetraallylglycoluril represented by the general formula (C1):

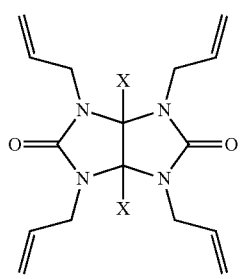

(C1)

wherein X represents a hydrogen atom, an alkyl or an aryl group, as an essential component.

According to the invention, the component (B) is preferably (B-3) an organic-modified silicone compound obtained by hydrosilylating (B-1) an organic compound having at least two alkenyl groups with (B-2) a linear and/or cyclic organohydrogen siloxane having at least two hydrosilyl groups in the molecule.

The component (B-1) is preferably at least one compound selected from the group consisting of polybutadiene, vinylcyclohexane, cyclopentadiene, divinyl biphenyl, bisphenol A diacrylate, trivinylcyclohexane, triallyl isocyanurate, methyl diallyl isocyanurate and glycolurils represented by the general formula (C2):

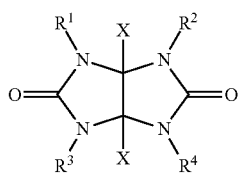

(C2)

wherein $R^1$, $R^2$, $R^3$ and $R^4$ each represents an organic group; at least two of them are alkenyl groups; and X represents a hydrogen atom, an alkyl or an aryl group. The component (B-1) is preferably the glycoluril represented by the general formula (C2) above.

According to the invention, the component (B-1) is most preferably the tetraallylglycoluril represented by the general formula (C1) above.

The component (B-2) is a cyclic and/or linear polyorganosiloxane having at least two hydrosilyl groups in the molecule, and preferably a cyclic polyorganosiloxane having at least two hydrosilyl groups in the molecule.

<(A) an Alkenyl Group-Containing Organic Compound>

The alkenyl group-containing organic compound according to the invention is not particularly limited, if it is an organic compound having at least one alkenyl group in the molecule. The organic compound is preferably not a compound containing siloxane units, such as a polysiloxane-organic block copolymer or a polysiloxane-organic graft copolymer, but a compound having only C, H, N, O, S and halogen atoms as constituent elements. The binding site of the alkenyl group is also not particularly limited and, the alkeny group may be bound to any site of the skeleton.

Concrete examples of the components (A) include diallyl phthalate, triallyl trimellitate, di(ethylene glycol) bis(allyl carbonate), trimethylolpropane diallyl ether, pentaerythritol triallyl ether, 1,1,2,2-tetraaryloxyethane, diallylidene pentaerythritol, triallyl cyanurate, triallyl isocyanurate, monoallyl dimethyl isocyanurate, 1,2,4-trivinylcyclohexane, diallyl monomethyl isocyanurate, divinylbenzenes (those with a purity of 50 to 100%, preferably with a purity of 80 to 100%), divinylbiphenyl, 1,3-diisopropenylbenzene, 1,4-diisopropenylbenzene, 1,2-polybutadiene (those with a 1,2-percentage of 10 to 100%, preferably with a 1,2-percentage of 50 to 100%), novolak phenol allyl ethers, allylated polyphenyleneoxides, tetraallylglycolurils represented by the general formula (C1) above and the oligomers thereof. These compounds may be used alone or in combination of two or more.

Among the concrete examples mentioned above, the tetraallylglycolurils are used preferably as the component (A), for example, from the viewpoint of the adhesiveness of the curable composition to the substrate when it is cured thereon, and also from the viewpoint of the balance between heat resistance and lightfastness and for effective reduction of heat stress.

Examples of the tetraallylglycolurils include:
1,3,4,6-tetraallylglycoluril,
1,3,4,6-tetraallyl-3a-methyl-glycoluril, 1,3,4,6-tetraallyl-3a,6a-dimethyl-glycoluril,
1,3,4,6-tetraallyl-3a,6a-diphenyl-glycoluril and the like.

Although the component (A) may have a functional group other than an alkenyl group bound to the skeleton, the functional group is preferably a less polar one, for example, a straight-chain aliphatic hydrocarbon group such as methyl, ethyl or propyl, from the viewpoint of compatibility with the component (B). When the functional group is a highly polar glycidyl, carboxyl or other group, there may result in deterioration in compatibility of the component (A) with the component (B), prohibiting preparation of transparent cured products.

The component (A) may be used alone or in combination of two or more; two or more components are preferably used in combination for control of the physical properties of the cured products; and the tetraallylglycolurils are used still more preferably from the viewpoint of the balance between heat resistance and lightfastness, as described above.

<(B) a Compound Having at Least Three Hydrosilyl Groups in the Molecule>

According to the invention, the component (B) is used mainly as a curing agent, and is not particularly limited, if it is an organosiloxane having at least three hydrosilyl groups in the molecule.

Examples of the component (B) include an organohydrogen organosiloxane, and an organic-modified silicone compound (component (B-3)) prepared by hydrosilylating an organic compound having at least two alkenyl groups (component (B-1)) with a linear and/or cyclic organohydrogen organosiloxane having at least two hydrosilyl group in the molecule (component (B-2)).

The organohydrogen organosiloxane refers to a siloxane compound having hydrocarbon groups or hydrogen atoms bound to the silicon atom.

Among the components (B) above, an organic-modified silicone compound (B-3) is used preferably from the viewpoint of the compatibility thereof with the organic compound or the component (A).

Examples of the organohydrogen organosiloxanes include the linear and cyclic compounds represented by the general formulae (1), (2) and (3) and hydrosilyl group-containing polyhedral polysiloxanes and the like.

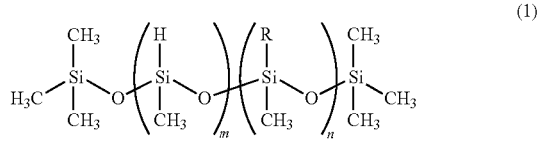

(1)

wherein 3<m+n≤50, 3<m, 0≤n, and R is a hydrocarbon group having 2 to 20 main-chain carbon atoms that may have one or more phenyl groups,

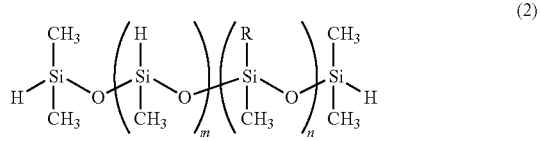

(2)

wherein 1<m+n≤50, 1<m, 0≤n, and R is a hydrocarbon group having 2 to 20 main-chain carbon atoms that may have one or more phenyl groups,

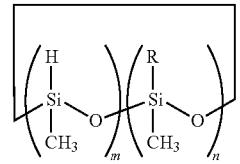

(3)

wherein 3≤m+n≤20, 3<m≤19, 0≤n<18, and R is a hydrocarbon group having 2 to 20 main-chain carbon atoms that may have one or more phenyl groups.

Various compounds obtained by reaction of different combinations of components (B-1) and (B2) can also be used as the organic-modified silicones of component (B-3).

The component (B-1) is not particularly limited, if it is an organic compound having at least two alkenyl groups. Concrete examples thereof include: diallyl phthalate, triallyl trimellitate, di(ethylene glycol) bis(allyl carbonate), trimethylolpropane diallyl ether, pentaerythritol triallyl ether, 1,1,2,2-tetraaryloxyethane, diallylidene pentaerythritol, triallyl cyanurate, triallyl isocyanurate, 1,2,4-trivinylcyclohexane, divinylbenzenes (those with a purity of 50 to 100%, preferably with a purity of 80 to 100%), divinylbiphenyl, 1,3-diisopropenylbenzene, 1,4-diisopropenylbenzene, diallyl monoglycidyl isocyanurate, diallyl monomethyl isocyanurate, bisphenol A diallyl ether, bisphenol S diallyl ether, tetraallylglycolurils and the oligomers thereof, 1,2-polybutadienes (those having a 1,2 ratio of to 100%, preferably having a 1,2 ratio of 50 to 100%), novolak phenol allyl ether, allylated polyphenyleneoxides, known epoxy resins having part or all of the glycidyl groups therein replaced with allyl groups, and the like.

The component (B-1) is preferably an organic compound having a heterocyclic ring skeleton for production of a cured product with favorable properties. The heterocyclic ring skeleton-containing organic compound is not particularly limited, if it is a compound having a hetero element in the cyclic skeleton, but those containing Si in the ring-forming atoms are excluded. The number of the ring-forming atoms is not particularly limited, and may be 3 or more, and preferably 10 or less from the point of commercial availability.

Concrete examples of the heterocyclic rings include epoxy, oxetane, furan, thiophene, pyrazole, oxazole, furazan, triazole, tetrazole, pyran, pyridine, oxazine, thiazine, pyridazine, pyrimidine, pyrazine, piperazine, glycoluril and the like. Glycoluril heterocyclic rings are preferable as the advantageous effects of the invention are shown significantly.

Thus, the glycoluril represented by the general formula (C2) above is preferably used, and the tetraallylglycoluril above is used more preferably as the component (B-1).

Examples of allylglycolurils including the tetraallylglycolurils include:
1-allylglycoluril,
1,3-diallylglycoluril,
1,4-diallylglycoluril,
1,6-diallylglycoluril,
1,3,4-triallylglycoluril,
1,3,4,6-tetraallylglycoluril,
1-allyl-3a-methyl-glycoluril,
1,3-diallyl-3a-methyl-glycoluril,
1,4-diallyl-3a-methyl-glycoluril,
1,6-diallyl-3a-methyl-glycoluril,
1,3,4-triallyl-3a-methyl-glycoluril, 1,3,4,6-tetraallyl-3a-methyl-glycoluril,
1-allyl-3a,6a-dimethyl-glycoluril,
1,3-diallyl-3a,6a-dimethyl-glycoluril,
1,4-diallyl-3a,6a-dimethyl-glycoluril,
1,6-diallyl-3a,6a-dimethyl-glycoluril,
1,3,4-triallyl-3a,6a-dimethyl-glycoluril,
1,3,4,6-tetraallyl-3a,6a-dimethyl-glycoluril,
1-allyl-3a,6a-diphenyl-glycoluril,
1,3-diallyl-3a,6a-diphenyl-glycoluril,
1,4-diallyl-3a,6a-diphenyl-glycoluril,
1,6-diallyl-3a,6a-diphenyl-glycoluril,
1,3,4-triallyl-3a,6a-diphenyl-glycoluril,
1,3,4,6-tetraallyl-3a,6a-diphenyl-glycoluril and the like.

According to the invention, the component (B-2) is not particularly limited, if it is an organohydrogen siloxane compound having at least two hydrosilyl group in the molecule and, for example, the compounds described in WO 96/15194 pamphlet that have at least two hydrosilyl groups in the molecule may be used. In particular, linear and/or cyclic organopolysiloxanes having at least two hydrosilyl groups in the molecule are preferable from the point of commercial availability, and cyclic organopolysiloxanes are preferable from the viewpoint of compatibility in the silicone-based curable composition.

Examples of the hydrosilyl group-containing cyclic siloxanes include: 1,3,5,7-tetramethylcyclotetrasiloxane, 1-propyl-3,5,7-trihydrogen-1,3,5,7-tetramethylcyclotetrasiloxane, 1,5-dihydrogen-3,7-dihexyl-1,3,5,7-tetramethylcyclotetrasiloxane, 1,3,5-trihydrogen-trimethylcyclosiloxane, 1,3,5,7,9-pentahydrogen-1,3,5,7,9-pentamethylcyclosiloxane, 1,3,5,7,9,11-hexahydrogen-1,3,5,7,9,11-hexamethylcyclosiloxane and the like. The hydrosilyl group-containing cyclic siloxane is preferably 1,3,5,7-tetramethylcyclotetrasiloxane from the viewpoint of commercial availability.

The molecular weight of the component (B-2) is not particularly limited, and any compound may be used, but a compound with low-molecular weight is preferable from the viewpoint of fluidity. The minimum molecular weight is 58 and the maximum molecular weight is 100,000, more preferably 1,000, and still more preferably 700.

<(C) a Hydrosilylation Catalyst>

According to the invention, the hydrosilylation catalyst of the component (C) is not particularly limited and any hydrosilylation catalyst may be used.

Examples thereof include: chloroplatinic acid, pure platinum, solid platinum supported on a carrier such as alumina, silica or carbon black; platinum-vinylsiloxane complexes {e.g., $Pt_n(ViMe_2SiOSiMe_2Vi)_n$ and $Pt[(MeViSiO)_4]_m$}; platinum-phosphine complexes (e.g., $Pt(PPh_3)_4$ and $Pt(PBu_3)_4$); platinum-phosphite complexes (e.g., $Pt[P(OPh)_3]_4$ and $Pt[P(OBu)_3]_4$) (wherein, Me represents a methyl group; Bu represents a butyl group; Vi represents a vinyl group; Ph represents a phenyl group; and n and m are integers), $Pt(acac)_2$, the platinum-hydrocarbon complexes described in U.S. Pat. Nos. 3,159,601 and 3,159,662 to Ashby et al., and the platinum alcoholate catalysts described in U.S. Pat. No. 3,220,972 to Lamoreaux et al.

Examples of the catalysts other than platinum compounds include $RhCl(PPh_3)_3$, $RhCl_3$, $Rh/Al_2O_3$, $RuCl_3$, $IrCl_3$, $FeCl_3$, $AlCl_3$, $PdCl_2 \cdot 2H_2O$, $NiCl_2$, $TiCl_4$ and the like.

These catalysts may be used alone or in combination of two or more. Chloroplatinic acid, platinum-olefin complexes, platinum-vinylsiloxane complexes, $Pt(acac)_2$ and the like are preferable from the viewpoint of catalytic activity.

The amount of the component (C) catalyst is not particularly limited, but the catalyst is preferably used in an amount in the range of $10^{-1}$ to $10^{-8}$ mole, and more preferably in the range of $10^{-2}$ to $10^{-6}$ mole with respect to 1 mole of the alkenyl group in the component (A). Hydrosilylation may not proceed sufficiently when the amount used is less than $10^{-8}$ mole, while the storage stability of the composition may be lowered when the amount used is more than $10^{-1}$ mole. The component (C) may be used alone or in combination of two or more.

<A Curable Composition>

The curable composition according to the invention is not particularly limited, if it is a composition that is cured by hydrosilylation reaction and comprises an alkenyl group-containing compound, a hydrosilyl group-containing compound and a hydrosilylation catalyst.

The molar ratio of component (A) to (B) in the curable composition is not particularly limited, but it is preferably in the range of 0.5 to 2.0, more preferably in the range of 0.7 to 1.5, and still more preferably in the range of 0.8 to 1.3 for efficient progress of the curing reaction (here, the molar ratio is (molar number of the hydrosilyl groups in the component (B))/(molar number of the alkenyl groups in the component (A))).

If the molar ratio is less than 0.5, for example, when the composition is cured, excess alkenyl groups may remain in the system, causing a problem in the heat resistance of the cured product. Alternatively, if the molar ratio is more than 1.3, excess hydrosilyl groups may remain in the system and condense with each other, for example, during long-term heat test, leading to deterioration of the properties of the cured product.

The viscosity of the curable composition is preferably 2000 cP or less, more preferably 1000 cP or less, and still more preferably 500 cP or less, from the viewpoint of handling efficiency.

When the viscosity is more than 2000 cP, the curable composition, when coated with a dispenser, may cause resin clogging or make it difficult to coat it uniformly.

<A Curing Retarder>

A curing retarder may be used for improvement of the storage stability of the curable composition according to the invention or for regulation of the reactivity of the hydrosilylation reaction in the production process. Examples of the curing retarders include aliphatic unsaturated bond-containing compounds, organic phosphorus compounds, organic sulfur compounds, nitrogen-containing compounds, tin compounds, organic peroxides and the like. These compounds may be used in combination.

Examples of the aliphatic unsaturated bond-containing compounds include propargyl alcohols, ene-yne compounds, maleic esters and the like. Examples of the organic phosphorus compounds include triorganophosphines, diorganophosphines, organophosphones, triorganophosphites and the like. Examples of the organic sulfur compounds include organomercaptans, diorganosulfides, hydrogen sulfide, benzothiazoles, benzothiazole disulfids and the like. Examples of the nitrogen-containing compounds include ammonia, primary to tertiary alkylamines, arylamines, ureas, hydrazines and the like. Examples of the tin compounds include stannous halide dihydrate, stannous carboxylates and the like. Examples of the organic peroxides include di-t-butyl peroxide, dicumyl peroxide, benzoyl peroxide, t-butyl perbenzoate and the like.

Among the curing retarders above, benzothiazole, thiazole, dimethyl malate and 3-hydroxy-3-methyl-1-butyne are favorable from the viewpoints of retarding activity and commercial availability of the material.

The storage stability-improving agent is used preferably in an amount of $10^1$ mole to $10^3$ moles, more preferably in an amount of 1 mole to 50 moles, with respect to 1 mole of the hydrosilylation catalyst used.

<An Adhesion Promoter>

The curable composition may comprise an adhesion promoter as an additive for improvement of adhesiveness to the substrate to be bonded. For example, a silane-coupling agent, a boron-based coupling agent, a titanium-based coupling agent, an aluminum-based coupling agent or the like may be used as the adhesion promoter.

The silane-coupling agents is preferably, for example, a silane-coupling agent having at least one functional group selected from epoxy, methacryl, acryl, isocyanate, isocyanurate, vinyl and carbamate and additionally silicon atom-bound alkoxy groups in the molecule. The functional group is more preferably an epoxy, methacryl or acryl group from the viewpoints of curability and adhesiveness.

Examples of the organic silicon compounds having an epoxy functional group and silicon atom-bound alkoxy groups include: 3-glycidoxypropyltrimethoxysilane, 3-glycidoxypropyltriethoxysilane, 2-(3,4-epoxycyclohexyl)ethyltrimethoxysilane and 2-(3,4-epoxycyclohexyl)ethyltriethoxysilane.

Examples of the organic silicon compound having a methacryl or acryl group and silicon atom-bound alkoxy groups include: 3-methacryloxypropyltrimethoxysilane, 3-methacryloxypropyltriethoxysilane, 3-acryloxypropyltrimethoxysilane, 3-acryloxypropyltriethoxysilane, methacryloxymethyltrimethoxysilane, methacryloxymethyltriethoxysilane, acryloxymethyltrimethoxysilane, and acryloxymethyltriethoxysilane.

Examples of the boron-based coupling agents include: trimethyl borate, triethyl borate, tri-2-ethylhexyl borate, tri-n-octadecyl borate, tri-n-octyl borate, triphenyl borate, trimethylene borate, tris(trimethylsilyl) borate, tri-n-butyl borate, tri-sec.-butyl borate, tri-tert.-butyl borate, triisopropyl borate, tri-n-propyl borate, triallyl borate and boron methoxyethoxide.

Examples of the titanium-based coupling agents include: tetra(n-butoxy)titanium, tetra(i-propoxy)titanium, tetra(stearoxy)titanium, titanium di-i-propoxybis(acetylacetonate), titanium i-propoxy(2-ethylhexane diolate), titanium di-i-propoxydiethylacetoacetate, titanium hydroxybis(lactate), i-propyl triisostearoyl titanate, i-propyltris(dioctyl pyrophosphate) titanate, tetra-(i-propyl)bis(dioctyl phosphite) titanate, tetraoctylbis(ditridecyl phosphite) titanate, bis(dioctylpyrophosphate)oxyacetate titanate, bis(dioctylpyrophosphate)ethylene titanate, i-propyltrioctanoyl titanate and i-propyldimethacryl-i-stearoyl titanate.

Examples of the aluminum-based coupling agents include: aluminum butoxide, aluminum isopropoxide, aluminum acetylacetonate, aluminum ethylacetoacetonate and acetoalkoxyaluminum diisopropylate.

These adhesiveness improvers may be used alone or in combination of two or more. The adhesiveness improver is used preferably in an amount of 5 parts or less by mass with respect to 100 parts by mass of the total amount of components (A) and (B).

<Other Additives>

An additive may be used for providing tackiness or adhesiveness to the cured product obtained by curing the curable composition of the invention, in an amount in the range that does not impair the advantageous effects of the invention. The additive used is not particularly limited, but a compound containing an alkenyl or hydrosilyl group, which can form chemical bond with the component (A) or (B) during curing by hydrosilylation, is preferably used for suppression of bleeding from the cured product.

Examples of the alkenyl group-containing compounds include: alkenyl group-containing dimethylpolysiloxanes blocked with dimethylvinylsiloxy groups at both chain terminals, dimethylpolysiloxanes blocked with methylphenylvinylsiloxy groups at both chain terminals, dimethylsiloxane-methylphenylsiloxane copolymers blocked with dimethylvinylsiloxy groups at both chain terminals, dimethylsiloxane-methylvinylsiloxane copolymers blocked with dimethylvinylsiloxy groups at both chain terminals, dimethylsiloxane-methylvinylsiloxane copolymers blocked with trimethylsiloxy groups at both chain terminals, methyl(3,3,3-trifluoropropyl)polysiloxanes blocked with dimethylvinylsiloxy groups at both chain terminals, dimethylsiloxane-methylvinylsiloxane copolymers blocked with silanol groups at both chain terminals, dimethylsiloxane-methylvinylsiloxane-methylphenylsiloxane copolymers blocked with silanol groups at both chain terminals, and the like.

These compounds may be used alone or in combination of two or more. These additives are used preferably in an amount of 5 parts or less by mass with respect to 100 parts by mass of the total amount of the components (A) and (B). Influence on hydrosilylation reaction should be taken into consideration, depending on the kind of the additives used and the addition amount thereof.

<A Cured Product Obtained by Curing the Curable Composition>

The cured product according to the invention is superior in heat resistance and lightfastness and also in adhesiveness to various substrates, and it also shows smaller curing shrinkage after curing. Thus, it is used suitably as a resin layer for various optical devices.

For reduction of heat stress, the cured product according to the invention preferably has a glass transition temperature of 150° C. or lower, and more preferably 145° C. or lower, still more preferably 140° C. or lower. If the cured product has a glass transition temperature of more than 150° C., heat stress applied thereto increases during curing or under high-temperature environments and the cured product may bend, for example, when cured on a substrate, and show smaller adhesiveness to the substrate.

Similarly as described above, the cured product according to the invention preferably has a storage elasticity of 500 MPa or less at 150° C., more preferably 200 MPa or less, and still more preferably 100 MPa or less, for reduction of heat stress. The cured product having a storage elasticity of 500 MPa or more may bend when cured on a substrate, as it receives larger heat stress and show smaller adhesiveness to the substrate.

The glass transition temperature can be determined by various methods, such as dynamic viscoelasticity measurement and thermomechanical measurement, and the storage elasticity can be determined by dynamic viscoelasticity measurement.

<An Optical Device>

Examples of the optical devices including the curable composition of the invention as resin layers include light-emitting diodes, various light-receiving devices, displays, solar cells and the like.

A light-emitting diode can be produced using the curable composition of the invention. In this case, the light-emitting element in the light-emitting diode can be covered with the curable composition of the invention.

The light-emitting element above refers to a light-emitting element used in known light-emitting diodes. Examples of such light-emitting elements include those prepared by laminating a semiconductor material on a substrate carrying, as needed, a buffer layer of GaN, AlN or the like by various methods including MOCVD method, HDVPE method and liquid-phase deposition. In this case, various materials can be used as the substrate. Examples thereof include sapphire, spinel, SiC, Si, ZnO, GaN single crystal and the like. In particular, the use of sapphire is preferable because it permits facile preparation of favorably crystalline GaN and is thus industrially valuable.

Examples of the semiconductor materials laminated thereon include GaAs, GaP, GaAlAs, GaAsP, AlGaInP, GaN, InN, AlN, InGaN, InGaAlN, SiC and the like. In particular, nitride compound semiconductors ($In_xGa_yAl_zN$) are preferable for high brightness. Such material may contain an activator or the like additionally.

The light-emitting element may comprise structures such as homo junction, hetero junction or double hetero structures containing MIS junction, pn junction or PIN junction. It may also have a single- or multiple-quantum well structure.

The light-emitting element may have or may not have a passivation layer. An electrode can be formed on the light-emitting element by a known method.

The electrode on the light-emitting element is electrically connected to lead terminals and the like by various methods. The material used for electrical connection is preferably a material that shows favorable ohmic characteristics in mechanical connection with the electrode of the light-emitting element and examples thereof include bonding wires such as of gold, silver, copper, platinum, aluminum and the alloys thereof. A conductive adhesive containing a conductive filler of silver, carbon or the like in resin may be used. In particular, aluminum or gold wire is favorably used, as they are favorably processable.

The light-emitting element is prepared as described above. Although the light-emitting element used in the light-emitting diode according to the invention may be any one, if it has a light intensity of 1 cd or more in the vertical direction. It is possible to have the advantageous effects of the invention significantly by using a light-emitting element having a light intensity of 2 cd or more in the vertical direction, and more significantly by using a light-emitting element having a light intensity of 3 cd or more in the vertical direction.

The emission output of the light-emitting element is not particularly limited and any emission output may be used. The emission wavelength of the light-emitting element may be any wavelength in the range from ultraviolet to infrared.

Monochromatic light may be emitted using one light-emitting element, or monochromatic or polychromatic light may be emitted using multiple light-emitting elements in combination.

The lead terminal connected to the light-emitting diode of the invention is preferably a lead terminal that is superior in adhesiveness and electrical conductivity to members electrically connected, such as bonding wires, and the electric resistivity of the lead terminal is preferably 300 µΩ-cm or less, more preferably 3 µΩ-cm or less. Examples of the materials for these lead terminals include iron, copper, iron copper alloy, tin copper alloy, those plated for example with silver or nickel, and the like. The glossiness of these lead terminals may be adjusted for favorable spread of the light.

The light-emitting diode of the invention is prepared by covering a light-emitting element with the curable composition of the invention. In this case, the covering is not limited to direct sealing, but includes indirect covering of the light-emitting element. Specifically, a light-emitting element may be sealed directly with the curable composition of the invention by one of various methods traditionally used. Alternatively, the light-emitting element may be first sealed with glass or a sealing resin traditionally used, such as an epoxy resin, a silicone resin, an acrylic resin, a urea resin or an imide resin, and then covered thereon or on the periphery with the curable composition of the invention. Yet alternatively, the light-emitting element may be sealed with the curable composition of the invention and then molded with a traditionally used resin such as an epoxy resin, a silicone resin, an acrylic resin, a urea resin or an imide resin. It is possible by the method mentioned above to provide a sealed product with various advantageous effects such as the lens effect, based on the difference in refractive index or specific density.

Various methods can be used also as the sealing methods. For example, a liquid composition may be injected into a cup, cavity or package dent having a light-emitting element placed on the bottom by a dispenser, and is cured by heating. Alternatively, a solid or high-viscosity liquid composition is fluidized by heating, and is injected similarly into a package dent or the like, and is then cured by heating. In this case, the package can be prepared with various materials and example of the materials include polycarbonate resins, polyphenylene sulfide resins, epoxy resins, acrylic resins, silicone resins, ABS resins, polybutylene terephthalate resins, polyphthalamide resins and the like.

Further, a method may be employed in which the composition is injected into a mold frame in advance; a lead frame having a light-emitting element connected thereto is immersed therein; and the resulting lead frame is cured. Alternatively, a method may also be employed in which a seal layer of the composition is molded by injecting the composition with a dispenser into a mold frame containing a light-emitting element placed therein or by transfer or injection molding, and is cured. Yet alternatively, a liquid or fluidized composition may simply be applied dropwise or coated on the light-emitting element and cured thereon.

The curable composition may be coated on a light-emitting element, for example, by stencil printing, screen printing or through-mask coating for molding, and cured. Alternatively, a partially or completely cured composition, for example, in the plate or lens shape, may be connected to a light-emitting element. Yet alternatively, the curable composition may be used as a die bonding agent used in connecting the light-emitting element to a lead terminal or a package or as a passivation film on the light-emitting element. The curable composition may also be used as a package substrate.

The shape of the covered region is also not particularly limited and may be variable. Examples of the shapes include lens shape, plate shape, thin film shape, the shapes described in JP-A No. 6-244458 and the like. These shapes may be formed by molding and curing the composition or by curing the composition and post-processing the cured composition.

The light-emitting diode of the invention may be one of any type, for example, a lamp-, SMD- or chip-type light-emitting diode. Various materials such as epoxy resins, BT resins, ceramics and the like are used for the SMD- and chip-type package substrates.

Any known traditional method may be applied to the light-emitting diode according to the invention. Examples of the methods include: a method of forming a light-reflecting or collecting layer on the rear face of a light-emitting element; a method of forming a complementary color-developing region on the bottom region for prevention of yellowing of the sealing resin; a method of forming a thin film absorbing light having a wavelength shorter than that of the main emission peak on a light-emitting element; a method of sealing a light-emitting element with a soft or liquid sealing material and molding the periphery thereof with a hard material; a method of sealing a light-emitting element with a material comprising a phosphor that absorbs the light from the light-emitting element and emits a fluorescence at a longer wavelength and then molding the periphery thereof; a method of molding a phosphor-containing material and then molding the product together with a light-emitting element; a method of molding a molding material in a special shape for improvement of luminous efficiency, as described in JP-A No. 6-244458; a method of forming two stages of dents in a package for reduction of irregularity in brightness; a method of inserting a light-emitting diode into a through-hole and immobilizing it therein; a method of forming a thin film absorbing a light having a wavelength shorter than that of main emission wavelength on the surface of a light-emitting element; a method of connecting a light-emitting element to a lead member, for example, by flip chip connection using, for example, a solder bump for emission of light in the substrate direction, and the like.

The light-emitting diode according to the invention can be used in various known applications. Concrete examples thereof include backlights, illuminations, light sources for sensors, light sources for vehicle instruments, signal lamps, indicating lamps, indicating devices, light sources for planarity light-emitting devices, displays, decorations, various lights and the like.

EXAMPLES

Hereinafter, the present invention will be described specifically with reference to Examples and Comparative Examples, but the invention is not limited thereto.
[Adhesiveness Test: Cross Cut Method]
3 cc of a curable composition was applied on a glass plate in the size of 10 cm×10 cm with a bar coater to give a coating film having a thickness of 40 to 60 μm and the coated film was cured in a convection oven at 150° C. for 1 hour to give a coating film test sample. The coating film obtained was subjected to the cross cut test according to JIS 5600-5-6 and the adhesiveness of the sample was evaluated according to the criteria specified in the specification and classified into 6 stages of 0 to 5.
[Heat-Resistance Test: Long-Term Heat Resistance Test]
A curable composition was fed into a mold prepared by holding a silicone rubber spacer having a thickness of 3 mm between two glass plates and was heated stepwise at 60° C. for 6 hours, at 70° C. for 1 hour, at 80° C. for 1 hour, at 120° C. for 1 hour and at 150° C. for 1 hours, to give a cured product test sample (3 mm in thickness). It was then cured in a convection oven at 120° C. for 100 hours; the color of the cured product was examined by visual observation and the sample without any coloring was designated as ⊙, the sample with slight surface coloring as ◯.
[Lightfastness Test]
A test sample was irradiated at a black panel temperature of 120° C. and an irradiance of 0.53 kW/m² to an integrated irradiance of 50 MJ/m², using a Metering Weather Meter manufactured by Suga Test Instrument Co., Ltd. and the change in appearance before and after irradiation was examined. The sample without change was designated as ◯, and that with change such as discoloration as x.

Preparative Example 1

In a 5-L two-necked flask equipped with a stirrer, a condenser tube and a dropping funnel, toluene (1800 g) and 1,3,5,7-tetramethylcyclotetrasiloxane (1440 g) were placed and stirred under heat in an oil bath at 120° C. A liquid mixture of 1,3,4,6-tetraallylglycoluril (240 g), toluene (200 g) and a xylene solution containing platinum vinylsiloxane complex (3% by weight as platinum, 1.44 ml) was added dropwise to the solution over 50 minutes. The solution obtained was stirred as it was under heat for 6 hours. 1-Ethynyl-1-cyclohexanol (2.95 mg) was added thereto and unreacted 1,3,5,7-tetramethylcyclotetrasiloxane and toluene were removed by distillation under reduced pressure to give a product (720 g).

$^1$H-NMR showed that the product is 1,3,5,7-tetramethylcyclotetrasiloxane, some of the hydrosilyl groups of which are bound to 1,3,4,6-tetraallylglycoluril. The modified product thus obtained was used as the component (A) in Examples and Comparative Example.

Preparative Example 2

Toluene (1380 g) and 1,3,5,7-tetramethylcyclotetrasiloxane (1360 g) were placed in a 5-L separable flask and heated to an internal temperature of 100° C. A mixture of 1,3,4,6-tetraallylglycoluril (330 g), a xylene solution of platinum vinylsiloxane complex (3% by weight as platinum, 1.36 mL) and toluene (300 g) was added thereto dropwise over a period of 30 minutes. During the dropwise addition, the internal temperature rose to 109° C. Unreacted 1,3,5,7-tetramethylcyclotetrasiloxane and toluene were removed by distillation under reduced pressure.

$^1$H-NMR showed that the product obtained was 1,3,5,7-tetramethylcyclotetrasiloxane some of the hydrosilyl groups of which are bound to 1,3,4,6-tetraallylglycoluril. The modified product thus obtained was used as the component (B) in Examples and Comparative Example.

Preparative Example 3

In a 5-L two-necked flask equipped with a stirrer, a condenser tube and a dropping funnel, toluene (1800 g) and 1,3,5,7-tetramethylcyclotetrasiloxane (1440 g) were placed and stirred under heat in an oil bath at 120° C. A liquid mixture of triallyl isocyanurate (200 g), toluene (200 g) and a xylene solution of platinum vinylsiloxane complex (3% by weight as platinum, 1.44 ml) was added dropwise to the solution over a period of 50 minutes. The solution obtained was stirred as it was under heat for 6 hours. 1-Ethynyl-1-cyclohexanol (2.95 mg) was added thereto and unreacted 1,3,5,7-tetramethylcyclotetrasiloxane and toluene were removed by distillation under reduced pressure to give a product (710 g).

$^1$H-NMR showed that the product is 1,3,5,7-tetramethylcyclotetrasiloxane, some of the hydrosilyl groups of which are bound to triallyl isocyanurate. The modified product thus obtained was used as component (A) in Comparative Example.

Examples 1 to 3 and Comparative Example 1

Each component was blended at the blending rate (parts by mass) shown in Table 7 to give a curable composition. The cured products for various tests were prepared under particular curing conditions and used in various tests.

The cured products obtained in Examples showed superior adhesiveness without deterioration in heat resistance and lightfastness, while those obtained in Comparative Example were insufficient in adhesiveness, heat resistance and lightfastness because the reduction in heat stress was insufficient.

The results above show that the curable composition according to the invention gives a cured product superior in heat resistance and lightfastness to various substrates without deterioration in adhesiveness.

TABLE 7

|  |  |  | Example | Comparative Example |
|---|---|---|---|---|
| Composition (parts by mass) | Component A | Preparative Example 1 | 50 |  |
|  |  | Preparative Example 3 |  | 40 |
|  | Component B | Preparative Example 2 | 50 | 60 |
|  | Component C | 3 wt % xylene solution of platinum-vinylsiloxane complex | 0.3 | 0.3 |

TABLE 7-continued

|  |  | Example | Comparative Example |
|---|---|---|---|
| Results of tests | Adhesiveness | Stage 1 | Stage 5 |
|  | Heat resistance | ◉ | ○ |
|  | Tg (° C.) | 150 | ND |
|  | Light fastness | ○ | X |

(4) A Thermosetting Resin Composition for Use in Sealing of Semiconductors, Comprising an Organopolysiloxane-Modified Allylglycoluril The thermosetting resin composition according to the invention comprises:

(A) an organopolysiloxane polymer represented by the general formula (C3):

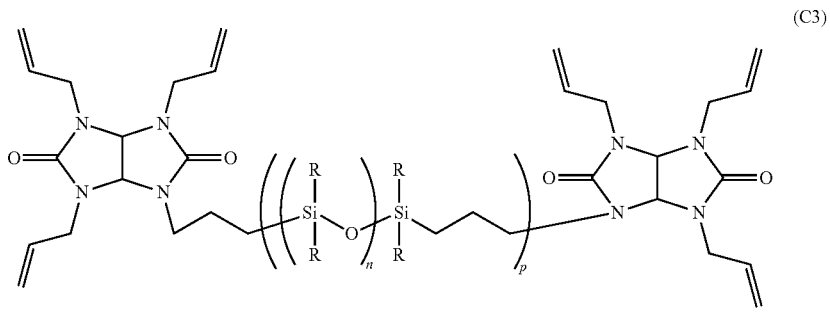

wherein each R independently represents an alkyl or a phenyl group; n is an integer of 1 to 50 and p is an integer of 1 to 30, as an alkenyl group-containing organopolysiloxane;

(B) a glycoluril ring-containing organohydrogen polysiloxane polymer represented by the general formula (C4):

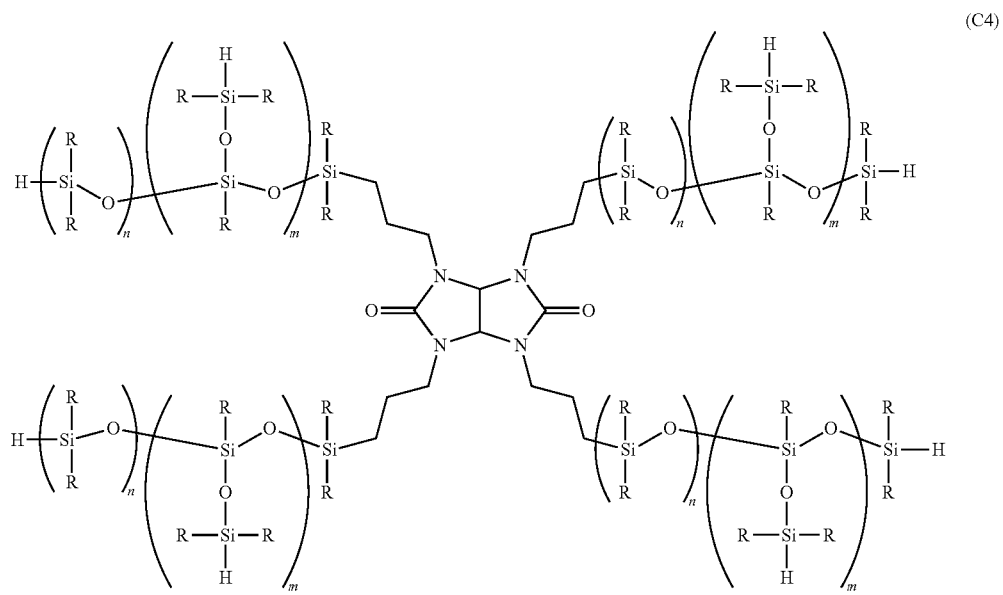

wherein each R independently represents an alkyl or a phenyl group; n is an integer of 1 to 50; m is an integer of 0 to 5; and siloxane recurring units in the general formula above may be bound to each other at random, as an organohydrogen polysiloxane; and (C) a curing accelerator.

The thermosetting resin composition of the invention comprises an organopolysiloxane polymer blocked with allylglycoluril rings at both chain terminals represented by the general formula (C3) above, i.e., an organopolysiloxane polymer having alkenyl groups (allyl groups) at both chain terminals, as the main agent (base polymer), and a glycoluril ring-containing organohydrogen polysiloxane polymer having at least two hydrogen atoms each bound to silicon atoms (Si—H groups) at the siloxane chain terminals represented by the general formula (C4) above as the curing agent (crosslinking agent). Thus, it gives a cured product with favorable properties provided by hydrosilylation (addition reaction).

The component (A) is an organopolysiloxane polymer having allylglycoluril ring structures at both chain terminals shown in the general formula (C3) above.

The composition of the invention comprises the organopolysiloxane polymer represented by the general formula (C3) above as the main agent (base polymer), that is, the alkenyl group-containing organopolysiloxane.

In the general formula (C3) above, the groups R each independently represents an alkyl group having 1 to 10 carbon atoms, such as methyl, ethyl or propyl, or a phenyl group, and the groups R are preferably methyl groups from the viewpoints of the curing properties and flexibility of the composition and easiness in preparing the same. It is preferred that 50 mol % or more (50 to 100 mol %) of all groups R are methyl groups.

In addition, p is an integer of 1 to 30, preferably an integer of 1 to 10, and more preferably an integer of 1 to 8.

The weight-average molecular weight of the organopolysiloxane polymer is normally 500 to 10,000, and preferably 600 to 5,000.

The viscosity of the organopolysiloxane polymer at 25° C. is normally 0.5 to 1,000 Pa·s, and preferably 1 to 100 Pa·s.

The weight-average molecular weight is determined, for example, by gel-permeation chromatography analysis, using, for example, THF as the developing solvent, while the viscosity is determined, using, for example, a rotating viscometer (BL-, BH-, BS- or cone plate-type viscometer) (the same shall apply hereinafter).

The component (A), i.e., the glycoluril ring-containing organopolysiloxane polymer is obtained, for example, by a known hydrosilylation addition reaction of a tetraallylglycoluril represented by the following chemical formula (1) and a terminal hydrogensiloxy group-blocked organopolysiloxane (hereinafter, referred to as the first terminal hydrogensiloxy group-blocked organopolysiloxane) represented by the following general formula (2).

The reaction temperature is normally from room temperature (25° C.) to 250° C., and preferably in the range of 50° C. to 180° C. The reaction time is normally in the range of 0.1 to 120 hours, and preferably in the range of 1 to 10 hours.

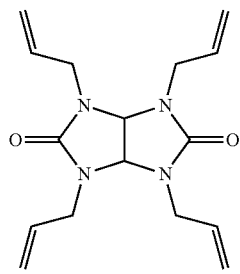

(1)

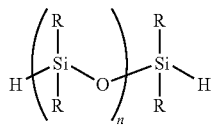

(2)

wherein R and n are the same as those described above.

The tetraallylglycoluril and the first terminal hydrogensiloxy group-blocked organopolysiloxane are reacted with each other so that the amount of the Si—H groups in the first terminal hydrogensiloxy group-blocked organopolysiloxane molecule is in the range of 0.1 to 0.9 equivalents, preferably in the range of 0.4 to 0.7 equivalents in relation to 1 equivalent of the allyl groups in the tetraallylglycoluril molecule (i.e., the allyl groups in excess). The reaction in this way provides an organopolysiloxane polymer having diallylglycoluril rings at both terminals (which may be hereinafter referred to as glycoluril ring-containing organopolysiloxane polymer).

The reaction may use a platinum group metal compound such as platinum, rhodium and palladium as the catalyst. Among the catalysts, in particular, a platinum-containing compound is preferred, and examples thereof include hexachloroplatinic (IV) acid hexahydrate, platinum-carbonylvinylmethyl complexes, platinum-divinyltetramethyldisiloxane complexes, platinum-cyclovinylmethylsiloxane complexes, platinum-octyl aldehyde/octanol complexes, activated carbon-supported platinum and the like.

The catalyst is used preferably in an amount of 0.01 to 10,000 ppm, more preferably 0.1 to 100 ppm (as metal by mass), in relation to the tetraallylglycoluril (mass).

A solvent may be used, as needed, in preparation of the glycoluril ring-containing organopolysiloxane polymer. Examples of the solvents for use include toluene, xylene, mesitylene, diethylbenzene, tetrahydrofuran, diethylether, 1,4-dioxane, diphenylether and the like.

The component (B) is a glycoluril ring-containing organohydrogen polysiloxane polymer having at least two hydrogen atoms respectively bound to silicon atoms (Si—H groups) at the siloxane chain terminals represented by the general formula (C4) above.

The thermosetting resin composition of the invention comprises the glycoluril ring-containing organohydrogen polysiloxane polymer represented by the general formula (C4) above, as a curing agent (crosslinking agent).

The component (B) is characteristically an organohydrogen polysiloxane having at least two hydrogen atoms bound to the silicon atoms (Si—H groups) at the siloxane chain terminals (i.e., in monofunctional siloxy unit) (hereinafter, referred to as the glycoluril ring-containing terminal hydrogen polysiloxane polymer). Because the organohydrogen polysiloxane has at least two, and preferably 2 to 50 highly reactive hydrogen atoms bound to the silicon atoms at the siloxane chain terminals (Si—H group in $(H)(R)_2SiO_{1/2}$ unit), it binds to the alkenyl groups (allyl groups) at both chain terminals of the component (A) rapidly in hydrosilylation addition reaction.

In the general formula (C4), the groups R each independently represents an alkyl group having 1 to 10 carbon atoms, such as methyl, ethyl or propyl, or a phenyl group; they are preferably methyl groups from the viewpoints of the curing properties and flexibility of the composition and easiness in preparing the same. In particular, it is preferred that 50 mol % or more (50 to 100 mol %) of all groups R are methyl groups.

The component (B) or the organohydrogen polysiloxane polymer has a weight-average molecular weight usually in the range of 500 to 10,000, and preferably in the range of 600 to 5,000.

Further, the organohydrogen polysiloxane polymer has a viscosity in the range of 0.1 to 100 Pa·s, preferably in the range of 0.5 to 10 Pa·s at 25° C.

The component (B) or the glycoluril ring-containing terminal hydrogen polysiloxane polymer is prepared, for example, by a known hydrosilylation addition reaction of the tetraallylglycoluril represented by the chemical formula (1) above and a terminal hydrogensiloxy group-blocked organopolysiloxane represented by the general formula (3) below (which may be hereinafter referred to as the second terminal hydrogensiloxy group-blocked organopolysiloxane). The reaction temperature is from normally room temperature (25° C.) to 250° C., and preferably, in the range of 50° C. to 180° C. The reaction time is normally 0.1 to 120 hours, and preferably 1 to 10 hours.

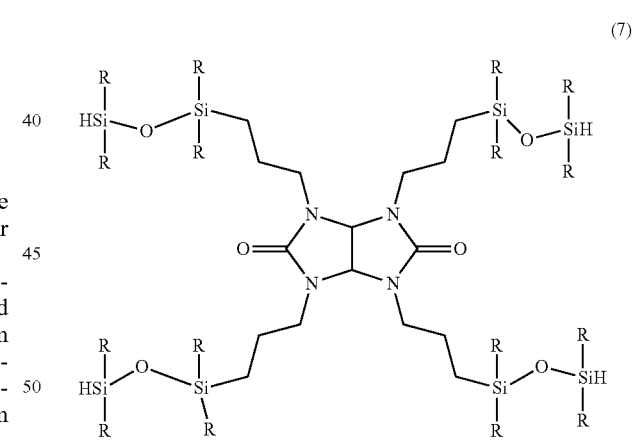

wherein R, m and n are the same as those described above and the siloxane recurring units may be bound to each other at random.

The tetraallylglycoluril and the second terminal hydrogensiloxy group-blocked organopolysiloxane are reacted with each other so that the amount of the Si—H groups in the second terminal hydrogensiloxy group-blocked organopolysiloxane molecule is in the range of 1.1 to 5.0 equivalents, and preferably in the range of 1.1 to 3.5 equivalents in relation to 1 equivalent of the allyl groups in the tetraallylglycoluril (i.e., the Si—H groups in excess).

The reaction in this way provides the glycoluril ring-containing organohydrogen polysiloxane polymer having at least two hydrogensiloxy groups at siloxane chain terminals.

Examples of the second terminal hydrogensiloxy group-blocked organopolysiloxanes include those represented by the chemical or general formulae (4) to (6):

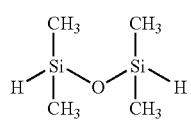

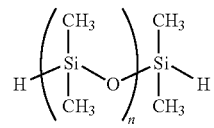

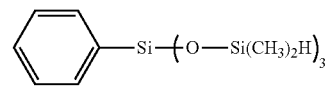

The reaction may use a platinum group metal compound such as platinum, rhodium and palladium as the catalyst. Among the catalysts, in particular, a platinum-containing compound is preferred, and examples thereof include hexachloroplatinic (IV) acid hexahydrate, platinum-carbonylvinylmethyl complexes, platinum-divinyltetramethyldisiloxane complexes, platinum-cyclovinylmethylsiloxane complexes, platinum-octyl aldehyde/octanol complexes, activated carbon-supported platinum and the like.

The catalyst is used preferably in an amount of 0.01 to 10,000 ppm, more preferably 0.1 to 100 ppm (as metal by mass) with respect to the tetraallylglycoluril represented by the chemical formula (1) (mass).

A solvent may be used, as needed, in preparation of the organohydrogen polysiloxane polymer. Examples of the solvents used include toluene, xylene, mesitylene, diethylbenzene, tetrahydrofuran, diethyl ether, 1,4-dioxane, diphenyl ether and the like.

Examples of the organohydrogen polysiloxane polymers obtained by the method described above include those represented by the following general formula (7).

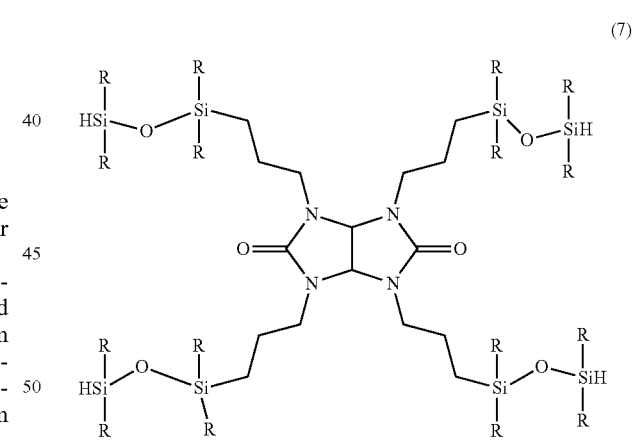

wherein R is the same as that described above.

The thermosetting resin composition of the invention comprises the component (B) or the glycoluril ring-containing terminal hydrogen polysiloxane polymer so that the amount of Si—H groups in the component (B) is in the range of 0.8 to 4.0 moles in relation to 1 mole of the allyl groups in the component (A) or the both-terminal allylglycoluril ring-blocked organopolysiloxane polymer. That is, the "Si—H group/allyl group" ratio is in the range of 0.8 to 4.0, and preferably in the range of 1.0 to 3.0

When the "Si—H group/allyl group" ratio is less than 0.8 or more than 4.0, the thermosetting resin composition may be cured insufficiently and generate surface irregularity on the resin surface after compression molding.

Crosslinking between the glycoluril ring-containing organopolysiloxane polymers of the components (A) and (B) gives a cured product superior in low elasticity, mechanical properties, heat resistance, electric insulating properties, chemical resistance, water resistance and gas permeability.

Because the organopolysiloxane polymer represented by the general formula (C3) as the main agent (base polymer) and the organohydrogen polysiloxane polymer represented by the general formula (C4) as the curing agent (crosslinking agent) are used for sealing a semiconductor element, they preferably contain halide ions such as chlorine and alkali ions such as sodium in amounts as small as possible, and in general, the content of any ions is desirably 10 ppm or less when it is determined by extraction at 120° C.

As the component (C) or the curing accelerators (curing catalyst), a hydrosilylation addition reaction catalyst may be used, preferably a platinum group metal catalyst such as a platinum- and palladium-based catalyst, iron oxide and the like. A patinum group metal catalyst is particularly preferable. Examples of the platinum group metal catalysts include platinum-, palladium-, rhodium- and other catalysts. Favorable among them from the viewpoint of cost are platinum-based catalysts such as platinum, platinum black and chloroplatinic acid (for example, $H_2PtCl-xH_2O$, $K_2PtCl_6$, $KHPtCl_{6-x}H_2O$, $K_2PtCl_4$, $K_2PtCl_4-xH_2O$, $PtO_{2-x}H_2O$ (x is a positive integer)), the complexes thereof with a hydrocarbon such as olefin, an alcohol or a vinyl group-containing organopolysiloxanes, and the like. These catalysts may be used alone or in combination of two or more.

The amount of the curing accelerator used is a catalytic amount (amount effectively accelerating curing). The amount of the platinum group metal catalyst used is preferably about 0.1 to 500 ppm, as platinum group metal by mass, with respect to the total amount of the components (A) and (B). When the amount used is not within the range above, the thermosetting resin composition may be cured insufficiently or show rapid increase in viscosity by excessively rapid curing, causing deterioration in processability.

The component (D) or the inorganic filler is not particularly limited in kind. However, it is preferred that the amount of the component (D) or the inorganic filler, such as silica, used in the thermosetting resin composition of the invention is in the range of 30 to 900 parts by mass, preferably in the range of 40 to 600 parts by mass with respect to 100 parts by mass of the total amount of the component (A), the both-terminal allylglycoluril ring-blocked organopolysiloxane polymer as the main agent and the component (B), the glycoluril ring-containing terminal hydrogen polysiloxane polymer as the curing agent.

When the amount is less than 30 parts by mass with respect to the total amount of the components (A) and (B) (i.e., the resin components), the thermosetting resin composition fails to give a cured product with sufficient strength. On the other hand, when it is more than 900 parts by mass, the composition may become less fluidal by thickening, making it difficult to seal semiconductor elements placed on a submount due to unfavorable filling efficiency.

The thermosetting resin composition of the invention may comprise various additives, as needed. Examples of the additives include epoxy group-containing organic silicon-based adhesiveness improvers; curing inhibitors such as ethynylmethyldecylcarbinol, organic phosphorus-containing compounds (such as triphenylphosphine), and organic nitrogen-containing compounds (such as tributylamine, tetramethylethylenediamine and benzotriazole); and colorants for example of various carbon blacks such as acetylene black and furnace black. These additives may be used in the range that does not impair the advantageous effects of the invention.

The thermosetting resin composition of the invention is prepared by mixing the components above uniformly.

The thermosetting resin composition obtained cures when heated. The curing condition may be 110 to 200° C., particularly 120 to 180° C. for 1 to 6 hours, in particular 2 to 3 hours.

The thermosetting resin composition may become solid, depending on the polymerization degree of the polysiloxane and the polysiloxane selected, but can be used for sealing semiconductors similarly by a method such as transfer molding.

The thermosetting resin composition of the invention gives a cured product superior in low elasticity, mechanical properties, heat resistance, electric insulating properties, chemical resistance, water resistance, gas permeability and others, and is thus a material suitable as a semiconductor sealer.

The thermosetting resin composition of the invention, when used for sealing a semiconductor element, gives a semiconductor device superior in heat resistance and moisture resistance and yet resistant to warping.

In the invention, the method of producing a semiconductor device is not particularly limited.

EXAMPLES

Hereinafter, the present invention will be described specifically with reference to Examples and Comparative Examples, but the invention is not limited thereto. In the following Examples, the room temperature is 25° C. and the "parts" is "parts by mass".

Preparative Example 1

Tetraallylglycoluril (400 g, 1.79 mole), toluene (400 g) and a toluene solution of chloroplatinic acid (0.32 g, containing 0.5 mass % of platinum) were placed in a 2-L separable flask; the mixture was heated at 100° C.; 1,1,3,3-tetramethyldisiloxane (120 g, 0.89 mole) was added thereto dropwise; the mixture was stirred at 100° C. for 8 hours; and toluene was removed by distillation under reduced pressure, to give a transparent and colorless liquid.

The results of $^1$H-NMR spectrum measurement showed that part of the allyl groups of tetraallylglycoluril reacted with 1,1,3,3-tetramethyl disiloxane.

Preparative Example 2

Tris(dimethyl hydrogen siloxy)phenylsilane (900 g, 2.73 mole) and toluene (900 g) were placed in a 3-L separable flask; the mixture was heated to 100° C.; a toluene solution of chloroplatinic acid (0.71 g, containing 0.5 mass % of platinum) was added dropwise; and then, tetraallylglycoluril (300 g, 1.34 mole) and toluene (300 g) were added dropwise. After the mixture was stirred at 100° C. for 8 hours, toluene was removed by distillation under reduced pressure, to give a transparent and colorless liquid.

The results of $^1$H-NMR spectrum measurement showed that tetraallylglycoluril was consumed completely and it was confirmed that the allyl groups of tetraallylglycoluril reacted with the terminal Si—H groups at one terminal of the terminal hydrogen siloxane.

Example 1

A resin composition having a proportion of the main agent to the curing agent of 1.0 as the ratio of Si—H group/allyl group and containing a silica filler in an amount of 60 mass % was prepared to have a composition shown below.
(1) Main agent: (Preparative Example 1), 58.0 parts by mass
(2) Curing agent: (Preparative Example 2), 37.0 parts by mass
(3) Curing accelerator: chloroplatinic acid (octyl alcohol-modified solution of chloroplatinic acid (platinum concentration: 2 mass %)), 0.5 part by mass
(4) Inorganic filler: silica filler, 157.8 parts by mass
(5) Curing inhibitor: (ethynylmethyldecylcarbinol), 0.5 part by mass
(6) Colorant: acetylene black (Denka Black, manufactured by Denka Company), 3.0 parts by mass These components (1) to (6) were stirred and mixed in a planetary mixer, kneaded thrice with three rolls arranged to have a pitch of 80 μm and mixed additionally under vacuum in the planetary mixer, to give a liquid thermosetting resin composition.

Example 2

A resin composition having a proportion of the main agent to the curing agent of 1.8 as the ratio of Si—H group/allyl group and containing a silica filler in an amount of 60 mass % was prepared to have a composition shown below.
(1) Main agent: (Preparative Example 1), 43.9 parts by mass
(2) Curing agent: (Preparative Example 2), 51.1 parts by mass
(3) Curing accelerator: chloroplatinic acid (octyl alcohol-modified solution of chloroplatinic acid (platinum concentration: 2 mass %)) 0.5 parts by mass
(4) Silica filler, 157.8 parts by mass
(5) Curing inhibitor: (ethynylmethyldecylcarbinol), 0.5 part by mass
(6) Colorant: acetylene black (Denka Black, produced by Denka Company Limited), 3.0 parts by mass These components (1) to (6) were stirred and mixed in a planetary mixer, kneaded thrice with three rolls arranged to have a pitch of 80 μm and mixed additionally under vacuum in the planetary mixer, to give a liquid thermosetting resin composition.

Example 3

A resin composition having a proportion of the main agent to the curing agent of 2.2 as the ratio of Si—H group/allyl group and containing a silica filler in an amount of 60 mass % was prepared to have a composition shown below.
(1) Main agent: (Preparative Example 1), 39.1 parts by mass
(2) Curing agent: (Preparative Example 2), 55.9 parts by mass
(3) Curing accelerator: chloroplatinic acid (octyl alcohol-modified solution of chloroplatinic acid (platinum concentration: 2 mass %), 0.5 part by mass
(4) Inorganic filler: silica filler, 157.8 parts by mass
(5) Curing inhibitor: (ethynylmethyldecyl carbinol), 0.5 part by mass
(6) Colorant: acetylene black (Denka Black, produced by Denka Company), 3.0 parts by mass These components (1) to (6) were stirred and mixed in a planetary mixer, kneaded thrice with three rolls arranged to have a pitch of 80 μm and mixed additionally under vacuum in the planetary mixer, to give a liquid thermosetting resin composition.

Comparative Example 1

Vinyl polysiloxane was used as the main agent and branched-chain organohydrogen polysiloxane was used as a curing agent. A resin composition having a proportion of the main agent to the curing agent of 2.0 as the ratio of Si—H group/Si-vinyl groups and containing a silica filler in an amount as much as of 80 mass % was prepared to have a composition shown below.
(1) Main agent-1: vinyl group-containing straight-chain dimethyl-polysiloxane, 87.2 parts by mass
(2) Curing agent-2: branched-chain organohydrogen polysiloxane, 2.8 parts by mass
(3) Curing accelerator: chloroplatinic acid (octyl alcohol-modified solution of chloroplatinic acid (platinum concentration: 2 mass %)) 0.5 parts by mass
(4) Inorganic filler: silica filler, 465.7 parts by mass
(5) Curing inhibitor: (ethynylmethyldecylcarbinol), 0.5 part by mass
(6) Colorant: acetylene black (Denka Black, produced by Denka Company), 3.0 parts by mass These components (1) to (6) were stirred and mixed in a planetary mixer, kneaded thrice with three rolls arranged to have a pitch of 80 μm and mixed additionally under vacuum in the planetary mixer, to give a liquid thermosetting resin composition.

[Test Methods]

The resin compositions obtained in Examples and Comparative Examples were subjected to evaluation tests (viscosity, DSC analysis and tensile strength) by the method described below.

The results of the test are summarized in Table 8.

(i) Viscosity

The viscosity was determined at room temperature using a Brookfield-programmable rheometer, (type: DV-III Ultra-viscometer, cone spindle CP-51/1.0 rpm).

(ii) DSC Analysis

The DSC analysis was performed using a METTLER's Model DSC821e analyzer.

(iii) Tensile Strength

After a No. 2 dumbbell-shaped sample of 1.0 mm-thickness was prepared from a molded article prepared by molding the cured product of a thermosetting resin composition (heat curing, 150° C.×2 hours), the tensile strength of the sample was determined using an AUTOGRAPH manufactured by Shimadzu Corp. Load cell type SBL-5KN (chuck distance: 100.0 mm, tension speed: 2.0 mm/minute).

[Table 8]

TABLE 8

|  | Examples | | | Comparative |
| --- | --- | --- | --- | --- |
|  | 1 | 2 | 3 | Example 1 |
| Viscosity (Pa · s) | 30 | 30 | 30 | — |
| DSC (° C.) | 121 | 122 | 120 | 120 |
| Tensile strength (N) | 40 | 45 | 50 | 17 |

The resin compositions of Examples 1 to 3 using only the both-terminal allylglycoluril ring-blocked organopolysiloxane polymer (compound A) and the glycoluril ring-containing terminal hydrogen polysiloxane polymer (compound B) as the main agent (base polymer) and the curing agent (crosslinking agent), respectively, gave a cured product superior both in heat resistance and tensile shear bond strength, even when the ratio of Si—H group/allyl group in the resin is altered to 1.0, 1.8 or 2.2.

In contrast, the resin composition of Comparative Example did not give a cured product superior both in heat resistance and tensile shear bond strength.

(5) An Electron Beam-Curable Resin Composition

The invention provides an electron beam-curable resin composition comprising a polyolefin resin and a crosslinking agent, wherein the crosslinking agent is an isocyanurate compound represented by the general formula (C5):

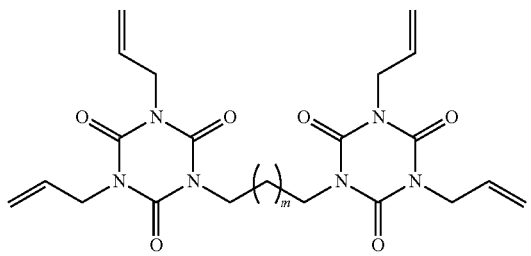

(C5)

wherein m is an integer of 0 to 16,
or by the general formula (C6):

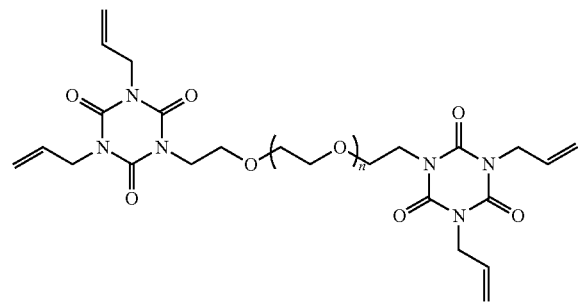

(C6)

wherein n is 0 or 1.

The invention provides a further electron beam-curable resin composition comprising a polyolefin resin and a crosslinking agent, wherein the crosslinking agent is an allylglycoluril represented by the general formula (C):

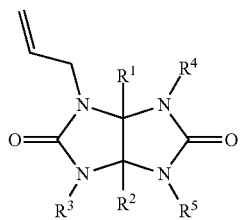

(C)

wherein $R^1$ and $R^2$ each independently represents a hydrogen atom, a lower alkyl or a phenyl group; and $R^3$, $R^4$ and $R^5$ each independently represents a hydrogen atom or an allyl group).

Thus, the electron beam-curable resin composition according to the invention comprises a polyolefin resin and a particular crosslinking agent.

The polyolefin resin used in practice of the invention is a polymer of olefin monomers, a polymer of polar monomers, or a copolymer of olefin and polar monomers.

Examples of the olefin monomers include α-olefin compounds having 2 to 20 carbon atoms such as ethylene, propylene, 1-butene, 1-pentene, 1-hexene, 3-methyl-1-butene, 3-methyl-1-pentene, 3-ethyl-1-pentene, 4-methyl-1-pentene, 4,4-dimethyl-1-pentene, 4-methyl-1-hexene, 4,4-dimethyl-1-hexene, 4-ethyl-1-hexene, 3-ethyl-1-hexene, 1-octene, 1-decene, 1-dodecene, 1-tetradecene, 1-hexadecene, 1-octadecene and 1-eicosene; cyclic olefin compounds having 3 to 20 carbon atoms such as cyclopentene, cycloheptene, 2-norbornene, 5-methyl-2-norbornene, 5,6-dimethyl-2-norbornene, 5-ethyl-2-norbornene, 5-butyl-2-norbornene, 5-ethylidene-2-norbornene, 5-methoxycarbonyl-2-norbornene, 5-cyano-2-norbornene, 5-methyl-5-methoxycarbonyl-2-norbornene, 5-hexyl-2-norbornene, 5-octyl-2-norbornene, 5-octadecyl-2-norbornene, tetracyclododecene, 1,4:5,8-dimethano-1,2,3,4,4a,5,8,8a-2,3-cyclopentadienonaphthalene, 6-methyl-1,4:5,8-dimethano-1,4,4a,5,6,7,8,8a-octahydronaphthalene, 1,4:5,10:6,9-trimethano-1,2,3,4,4a,5,5a,6,9,9a and 10,10a-dodecahydro-2,3-cyclopentadienoanthracene; aromatic vinyl compounds such as styrene, substituted styrenes, allylbenzene, substituted allylbenzenes, vinylnaphthalenes, substituted vinylnaphthalenes, allylnaphthalenes, and substituted allylnaphthalenes; alicyclic vinyl compounds such as vinylcyclopentane, substituted vinylcyclopentanes, vinylcyclohexane, substituted vinylcyclohexanes, vinylcycloheptane, substituted vinylcycloheptanes and allyl norbornanes; silane-based unsaturated compounds such as allyltrimethylsilane, allyltriethylsilane, 4-trimethylsilyl-1-butene, 6-trimethylsilyl-1-hexene, 8-trimethylsilyl-1-octene and 10-trimethylsilyl-1-decene; conjugated or non-conjugated diene compounds such as butadiene, 1,4-hexadiene, 7-methyl-1,6-octadiene, 1,8-nonadiene, 1,9-decadiene, norbornadiene and dicyclopentadiene; and the like.

Examples of the polar monomers include:

α,β-unsaturated carboxylic acids such as acrylic acid, methacrylic acid, fumaric acid, maleic anhydride, itaconic acid, itaconic anhydride and bicyclo[2.2.1]-5-heptene-2,3-dicarboxylic acid;

the metal salt compounds thereof such as of sodium, potassium, lithium, zinc, magnesium and calcium;

α,β-unsaturated carboxylic ester compounds such as methyl acrylate, ethyl acrylate, n-propyl acrylate, isopropyl acrylate, n-butyl acrylate, isobutyl acrylate, t-butyl acrylate, 2-ethylhexyl acrylate, methyl methacrylate, ethyl methacrylate, n-propyl methacrylate, isopropyl methacrylate, n-butyl methacrylate and isobutyl methacrylate;

unsaturated dicarboxylic acids such as maleic acid and itaconic acid; vinyl ester compounds such as vinyl acetate, vinyl propionate, vinyl caproate, vinyl caprate, vinyl laurate, vinyl stearate and vinyl trifluoroacetate;

unsaturated glycidyl group-containing monomers such as glycidyl acrylate, glycidyl methacrylate and monoglycidyl itaconate; and the like.

In practice of the invention, the polymers of olefin monomers, the polymers of polar monomers, or the copolymers of olefin and polar monomers may be used alone or in combination of two or more.

In particular, among the polyolefin resins mentioned above, a homopolymer of 4-methyl-1-pentene, or a copolymer of 4-methyl-1-pentene with another olefin monomer containing 4-methyl-1-pentene in an amount of 90 mol % or more (polymethylpentene) has a refractive index of 1.46, which is similar to the refractive index of silica particle, so that it can suppress inhibition of optical properties such as reflectance, when blended, and is thus suitable for use as a reflector for semiconductor luminescent devices.

However, the above-mentioned polymers are not sufficiently heat-resistant in the reflow process and thus, the use of the polymers in such an application was difficult. As a measure to overcome this disadvantage, according to the invention, the polymethylpentene is blended with the isocyanurate compound or the glycoluril as a crosslinking agent to provide an electron beam-curable resin composition, which is irradiated with electron beam having sufficient heat resistance even in the reflow process. As a result, the invention has made it possible to use the polymers as a reflector for semiconductor luminescent devices.

The crosslinking agent used in practice of the invention is either the isocyanurate compound represented by the general formula (C5) or (C6), or the glycoluril represented by the general formula (C) above.

Examples of the isocyanurate compounds represented by the general formula (C5) above include:
ethylene bis(diallyl isocyanurate),
trimethylene bis(diallyl isocyanurate),
tetramethylene bis(diallyl isocyanurate),
pentamethylene bis(diallyl isocyanurate),
hexamethylene bis(diallyl isocyanurate),
heptamethylene bis(diallyl isocyanurate),
octamethylene bis(diallyl isocyanurate),
nonamethylene bis(diallyl isocyanurate),
decamethylene bis(diallyl isocyanurate),
dodecamethylene bis(diallyl isocyanurate) and the like.
    These compounds may be used alone or in combination of two or more.
    Examples of the isocyanurate compound represented by the general formula (C6) include:
        oxydiethylene bis(diallyl isocyanurate), 1,2-bis(3,5-diallyl isocyanurylethoxy)ethane, and the like. These compounds may be used alone or in combination.
    Examples of the allylglycolurils represented by general formula (C) above include:
1-allylglycoluril,
1,3-diallylglycoluril,
1,4-diallylglycoluril,
1,6-diallylglycoluril,
1,3,4-triallylglycoluril,
1,3,4,6-tetraallylglycoluril,
1-allyl-3a-methylglycoluril,
1,3-diallyl-3a-methylglycoluril,
1,4-diallyl-3a-methylglycoluril,
1,6-diallyl-3a-methylglycoluril,
1,3,4-triallyl-3a-methylglycoluril,
1,3,4,6-tetraallyl-3a-methylglycoluril,
1-allyl-3a,6a-dimethylglycoluril,
1,3-diallyl-3a,6a-dimethylglycoluril,
1,4-diallyl-3a,6a-dimethylglycoluril,
1,6-diallyl-3a,6a-dimethylglycoluril,
1,3,4-triallyl-3a,6a-dimethylglycoluril,
1,3,4,6-tetraallyl-3a,6a-dimethylglycoluril,
1-allyl-3a,6a-diphenylglycoluril,
1,3-diallyl-3a,6a-diphenylglycoluril,
1,4-diallyl-3a,6a-diphenylglycoluril,
1,6-diallyl-3a,6a-diphenylglycoluril,
1,3,4-triallyl-3a,6a-diphenylglycoluril,
1,3,4,6-tetraallyl-3a,6a-diphenylglycoluril and the like.
    These compounds may be used alone or in combination of two or more.

The electron beam-curable resin composition of the invention comprises the crosslinking agent in an amount preferably in the range of 0.1 to 50 parts by mass, and more preferably in the range of 0.5 to 20 parts by mass, with respect to 100 parts by mass of the polyolefin resin.

The electron beam-curable resin composition of the invention may comprise an unsaturated compound having an allyl, (meth)acryloxy or other groups in combination as other crosslinking agent in the range that does not impair the advantageous effects of the present invention.

Examples of the unsaturated compounds include: polyallyl compounds such as triallyl isocyanurate, triallyl cyanurate, diallyl glycidyl isocyanurate, diallyl phthalate, diallyl fumarate, diallyl maleate and tetraallylglycoluril; poly(meth)acryloxy compounds such as ethylene glycol diacrylate, ethylene glycol dimethacrylate and trimethylolpropane trimethacrylate; divinylbenzene and the like.

The electron beam-curable resin composition of the invention preferably contains a white pigment or other inorganic particles.

One or more of titanium oxide, zinc sulfide, zinc oxide, barium sulfide and others may be used as the white pigment and in particular, titanium oxide is preferable. The amount of the white pigment used is preferably 1 to 500 parts by mass, and more preferably 5 to 300 parts by mass, with respect to 100 parts by mass of the polyolefin resin. The average diameter of the white pigment is preferably 0.10 to 1.00 µm, and more preferably 0.10 to 0.50 µm, as primary particle size distribution from the viewpoint of moldability and for preparation of high-reflectance products. The average diameter can be determined as a mass average D50 by the particle size distribution measurement by a laser diffraction method.

Examples of the other inorganic particles include spherical fused silica particles, modified cross-section glass fibers, other glass fibers and the like, and spherical fused silica particles and/or modified cross-section glass fibers are preferable.

The spherical fused silica particles and the modified cross-section glass fibers are used in common thermoplastic resin compositions or in common thermosetting resin compositions such as epoxy resins, acrylic resins and silicone resins, and such particles or fibers may be used alone or in combination of two or more in the electron beam-curable resin composition of the invention.

The spherical fused silica particles are prepared, for example, by a process in which a raw material for silicon dioxide powder such as silica is fed in the powder state with a carrier gas such as air into the flame generated in the melting zone in a furnace, and is then injected with a burner. Generally, a commercially available product may be used.

The volume average diameter of the spherical fused silica particles is preferably 0.1 to 500 µm, and more preferably 1 to 300 µm. The volume average diameter is determined as a mass average D50 by particle size distribution measurement by a laser diffraction method.

The modified cross-section glass fiber refers to a fiber having an uneven crossectional shape with different major and minor axis lengths, can reinforce the molded product mostly evenly in the machine direction (MD) and the transverse direction (TD) and is thus effective in preventing warping of the molded product.

According to the invention, the modified cross-section glass preferably has an average fiber length 0.75 to 300 µm and has a crossectional shape of a crossectional minor axis length (D1) of 0.5 to 25 µm and a major axis length (D2) of 0.6 to 300 µm, wherein the D2/D1 ratio is 1.2 to 30. The fiber diameter and length can be determined by sampling a certain amount of glass fiber at random from an arbitrary point of a glass fiber-laminated film, pulverizing the resulting fiber with a mortar and analyzing them with an image processing device.

The content of the spherical fused silica particles and/or the modified cross-section glass fiber is preferably 1 to 500 parts by mass, and more preferably 10 to 300 parts by mass, with respect to 100 parts by mass of the polyolefin resin.

The electron beam-curable resin composition of the invention is prepared by blending a polyolefin resin, a crosslinking agent and, as needed, a white pigment or other inorganic particles at the predetermined ratio as described above. The electron beam-curable resin composition comprising a white pigment or other inorganic particles is particularly suitable for use in reflectors.

The electron beam-curable resin composition of the invention comprises various additives in the range that does not impair the advantageous effects of the invention. For example, additives such as internal release agents such as various whiskers, silicone powders, organic synthetic rubbers, thermoplastic elastomers, fatty acid esters, zinc stearate, calcium stearate and glyceric esters; antioxidants such as benzophenone-, isocyanurate-, phenol-, salicylic acid-, oxalic acid anilide-, benzoate-, hindered amine-, and benzotriazole-based antioxidants; and photostabilizers such as hindered amine- and benzoate-based photostabilizers may be added for improvement of the properties of the resin composition.

The electron beam-curable resin composition of the invention is prepared by mixing the raw materials described above by a known means, for example with a stirrer such as three- or two-roll mill, homogenizer or planetary mixer or a melt-extruder such as Polylab System or Labo Plastmill. The mixing may be carried out either at normal, cooled or heated temperature under normal, reduced, or higher pressure.

Various molded products are obtained by using the electron beam-curable resin composition of the invention as raw material. Thinner molded articles such as reflectors are also obtained.

Such a molded article is preferably prepared by a molding method including an injection molding process of the electron beam-curable resin composition of the invention as raw material at a cylinder temperature of 200 to 400° C. and a mold temperature of 20 to 100° C., and then an electron beam-irradiating process of irradiating the molded product with electron beam before or after the injection molding process. The crosslinking reaction by irradiation with electron beam irradiation can be carried out before molding, if the moldability is not inhibited.

The voltage for acceleration of electron beam can be selected appropriately according to the resin and the layer thickness used. For example, in the case of a molded article having a thickness of about 1 mm, the uncured resin layer is preferably cured normally at an accelerating voltage of about 250 to 2000 kV. In irradiation of electron beam, the degree of penetration increases as the accelerating voltage is increased. Thus when a substrate labile to electron beam is used, it is possible by adjusting the accelerating voltage suitably to make the electron beam penetration depth identical with the thickness of the resin layer to prevent excessive irradiation of electric beam to the substrate, and to suppress the degradation of the substrate by excess electron beam to the minimum.

The amount of the radiation absorbed during irradiation of electron beam is adjusted appropriately according to the composition of the resin composition, but it is preferably the amount at which the crosslinking density of the resin layer becomes saturated, preferably 10 to 400 kGy, and more preferably 50 to 200 kGy. The source of the electron beam is not particularly limited, and various electron beam accelerators including Cockcroft Walton-, resonant transformer-, insulated core transformer-, Van de Graft-, straight line-, dynamitron- and high-frequency-type accelerators can be used.

As described above, the cured product of the electron beam-curable resin composition of the invention can be used in various applications including heat-resistant insulation films, heat-resistant release sheets, heat-resistant transparent substrates, solar cell photoreflection sheets, LED illuminations, and reflectors to the light source of television.

Hereinafter, the reflector resin frame according to the invention will be described.

The reflector resin frame according to the invention is made of a cured product from the electron beam-curable resin composition described above. Specifically, the electron beam-curable resin composition of the invention is pelletized, and then the resulting pellets are injection-molded into a resin frame according to the invention. The thickness of the reflector resin frame is preferably 0.1 to 5.0 mm, and more preferably 0.1 to 2.0 mm.

The use of the electron beam-curable resin composition of the invention makes it possible to produce a resin frame thinner than that obtained by using an anisotropically shaped glass fiber. Specifically, a resin frame having a thickness of 0.1 to 3.0 mm can be produced. The reflector resin frame of the invention is resistant to warping due to the anisotropic filler contained therein such as glass fiber even when the thickness thereof is lowered and thus, superior in handleability and dimensional stability.

A semiconductor luminescent device is produced from the reflector resin frame of the invention by placing an LED element on the reflector resin frame, sealing the resultant with a known sealing agent, and then converting the sealed product into a desired shape by die bonding. The reflector resin frame of the invention functions as a reflector and also as a package for immobilization of semiconductor luminescent devices.

The reflector resin frame of the invention contains spherical fused silica particles, unlike the case wherein porous silica particles are contained, and thus, foaming by water is suppressed in production of the reflector resin frame, and there are generated no micropores that leads to defects. Thus, products prepared by using the frame, such as semiconductor light-emitting elements, have a reduced traditional problem of micropore-derived defects and show improved durability as product.

Hereinafter, the reflector according to the invention will be described.

The reflector according to the invention is made of a cured product of the electron beam-curable resin composition described above.

The reflector of the invention may be used in a semiconductor luminescent device described below or in combination with a semiconductor luminescent device of other material such as a substrate for mounting LED.

The reflector of the invention has a main function of reflecting the light from the LED element in a semiconductor luminescent device to the lens of the light-emitting unit. The reflector is the same as that applied to the semiconductor luminescent device of the invention and thus detailed description thereof is omitted.

The reflector of the invention contains spherical fused silica particles, unlike the case when porous silica particles are contained, and thus, foaming by water is suppressed in production of the reflector, and there are generated no micropores that leads to defects. Thus, the products prepared by using the reflector, such as semiconductor light-emitting elements, have a reduced traditional problem of micropore-derived defects and show improved durability as product.

As described above, a semiconductor luminescent device having a reflector that is prepared by using the electron beam-curable resin composition containing spherical fused silica particles does not have micropores that leads to defects of the reflector, thus has a reduced traditional problem of micropore-derived defects and show improved durability as product.

Hereinafter, the semiconductor luminescent device according to the invention will be described.

The semiconductor luminescent device of the invention has a substrate, an optical semiconductor element such as LED element and a reflector at least partially made of a cured product of the electron beam-curable resin composition described above, which reflects the light from the optical semiconductor element to a predetermined direction, and is immobilized around the optical semiconductor element, formed on the substrate.

In the case of a white light LED, the optical semiconductor element is a semiconductor chip (light-emitting body) in a double hetero structure wherein an active layer such as of AlGaAs, AlGaInP, GaP or GaN that emits a radiation light such as UV or blue light is sandwiched with hexagonal n-type and p-type cladding layers having a side length of about 0.5 mm, and the optical semiconductor element is connected to a connection terminal electrode via a lead wire in the case of a wire-bonding mounting system.

The shape of the reflector is designed according to the shape of the lens junction unit and may be cylindrical or ring-shaped (such as circular, square or elliptical). The reflector is generally a cylindrical body (ring-shaped body) and all edge face of the reflector is in contact with and connected to the surface of the substrate.

The internal surface of the reflector may be widened gradually upward for improvement of light directivity from the optical semiconductor element. The reflector can also function as a lens holder when the lens-sided terminal is processed to be compatible with the shape of the lens.

Only the light-reflecting side of the reflector may be a light-reflectance layer prepared with the cured product of the electron beam-curable resin composition of the invention. In this case, the thickness of the light-reflectance layer is preferably 500 μm or less, and more preferably 300 μm or less, for example, for reduction of thermal resistance. The substrate on which the light-reflectance layer is formed may be made of any known heat-resistant resin.

As described above, a lens is formed on the reflector and it is normally made of a resin. Lenses in various structures and colors are used, for example, according to the object and application thereof.

The space between the substrate, the reflector, and the lens may be vacant or sealed with a transparent sealing agent, but it is generally a transparent sealed region filled with a transparent and insulating material. The space reduces the electrical troubles by short circuiting, removal or breakage of the lead wire from the connecting unit to optical semiconductor element and/or the connecting unit to electrode, for example, caused by the pressure by direct contact to the lead wire and the vibration and impact indirectly applied thereto during wire-bonding packaging. The space also protects the optical semiconductor element from dusts, humidity and others and preserves its reliability over an extended period of time.

Examples of the transparent sealing agents used normally include epoxy resins, silicone resins, epoxy silicone resins, acrylic resins, polyimide resins, polycarbonate resins and the like. Among the resins above, silicone resins are preferable from the viewpoints of discoloration resistance, heat resistance, weather resistance and low shrinkage.

EXAMPLES

Hereinafter, the present invention will be described specifically with reference to Examples and Comparative Examples, but the invention is not limited thereto.

<Preparation of an Electron Beam-Curable Resin Composition>

An electron beam-curable resin composition formed of the isocyanurate compound or the glycoluril shown in Table 9 as a crosslinking agent (2 parts by mass), a polymethylpentene resin (product name: TPX RT18, produced by Mitsui Chemicals, molecular weight MW: 500,000 to 600,000) as a resin (100 parts by mass), a modified cross-section glass fiber (CSG3PA-820 produced by Nitto Boseki Co., Ltd.) as inorganic particles (60 parts by mass), titanium oxide particles (PF-691 produced by Ishihara Sangyo Kaisha, Ltd.) as a white pigment (45 parts by mass), a silane coupling agent (KBM-303, produced by Shin-Etsu Chemical, 1.5 parts by mass), an antioxidant (IRGANOX 1010 produced by BASF, 1 part by mass), a processing stabilizer (IRGAFOS 168, 0.5 part by mass), and a release agent (SZ-2000 produced by Sakai Chemical Industry, 0.5 part by mass) as an additive was press-molded into a shape of 750 mm×750 mm×thickness 0.2 mm under a condition of 250° C./30 seconds/20 MPa, to give a molded article. Electron beam was irradiated to the molded article at an accelerating voltage of 250 kV and an absorbed dose of 100 kGy and the resulting molded article was used as a test sample.

<Long-Term Heat Resistance Test>

First, the initial reflection of light in the wavelength range of 230 to 780 nm of the test sample obtained above was determined using a spectrophotometer (UV-2550, manufactured by Shimadzu Corp.). Subsequently, the test sample was left at 150° C. for 500 hours and the reflection of light thereof was determined in the same manner as the method above. The results of the test obtained using a light at a wavelength of 450 nm are shown in Table 9.

<Reflow Heat Resistance Test>

The test sample obtained above was first placed in a small nitrogen-atmosphere reflow apparatus (RN-S, manufactured by Panasonic Corporation) adjusted to heat the test sample at a highest temperature of 260° C. for 10 seconds and the dimensional change of the test sample (sum of the changes in crosswise and lengthwise directions) was determined. The results of the test obtained are shown in Table 9.

TABLE 9

| | Crosslinking agent | Long-term heat resistance test Reflection of light (%) | | Reflow heat resistance test |
|---|---|---|---|---|
| | | Initial | After 500 hours | Dimensional change (%) |
| Example 1 | Tetramethylene bis(diallyl isocyanurate) | 98 | 90 | 0.1 |
| Example 2 | Oxydiethylene bis(diallyl isocyanurate) | 98 | 89 | 0.2 |
| Example 3 | 1,2-Bis(3,5-diallyl iscyanur-ethoxy)ethane | 97 | 89 | 0.1 |

TABLE 9-continued

| | Crosslinking agent | Long-term heat resistance test Reflection of light (%) | | Reflow heat resistance test |
| | | Initial | After 500 hours | Dimensional change (%) |
| --- | --- | --- | --- | --- |
| Example 4 | 1,3,4,6-Tetraallyl-glycoluril | 97 | 89 | 0.2 |
| Comparative Example 1 | 1,3,5-triallyl isocyanurate | 94 | 82 | 0.7 |

The results shown in Table 9 demonstrate that the electron beam-curable resin composition of the invention is superior in long-term heat resistance and significantly resistant to the shape change by reflow heating. Thus, the electron beam-curable resin composition of the invention is useful as a reflector or as a reflecting material for semiconductor luminescent devices.

(6) A Silicone Resin Composition

The silicone resin composition of the invention comprises:

component (A): a polysiloxane having at least two silicon-bound alkenyl groups, component (B): a polysiloxane having at least two silicon-bound hydrogen groups as a crosslinking agent, component (C): a hydrosilylation reaction catalyst, and component (D): an allylglycoluril represented by the general formula (C):

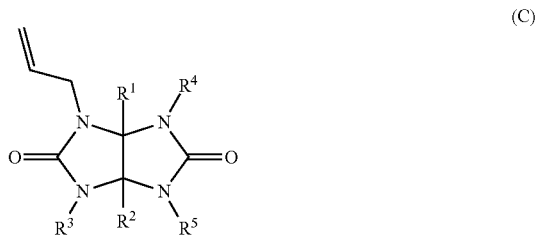

(C)

wherein $R^1$ and $R^2$ each independently represents a hydrogen atom, a lower alkyl or a phenyl group; and $R^3$, $R^4$ and $R^5$ each independently represents a hydrogen atom or an allyl group, and wherein the component (D) is contained in an amount of 0.1 to 10 parts by mass with respect to 100 parts by mass of the total amount of the components (A) and (B).

The component (A) for use in practice of the invention is not particularly limited, if it is an organopolysiloxane having at least two alkenyl groups bound to silicon atoms in the molecule and having a polysiloxane structure as the main chain.

The component (A) is the main agent (base polymer) of the silicone resin composition of the invention. The component (A) preferably has at least two or more, more preferably 2 to 20, and still more preferably 2 to 10 alkenyl groups bound to silicon atoms in the molecule from the viewpoints of favorable toughness and elongation.

The component (A) may be a polysiloxane having one vinyl group and/or one hydrosilyl group in the molecule so that the resulting composition has a low viscosity.

The alkenyl group may bind to a silicon atom via an organic group. The organic group is not particularly limited and may have a hetero atom such as an oxygen, nitrogen or sulfur atom.

Examples of the alkenyl groups include unsaturated hydrocarbon groups having 2 to 8 carbon atoms such as vinyl, allyl, butenyl, pentenyl, hexenyl and heptenyl; and a (meth)acryloyl group. In particular, it is preferably a vinyl or (meth)acryloyl group, and more preferably a vinyl group as the resulting composition is superior in curability.

The (meth)acryloyl group, as used in the invention, means one or both of acryloyl and methacryloyl groups.

The binding sites of the alkenyl group are one or both of the chain terminals and molecular side chains of polysiloxane. The alkenyl group may bind to one or both terminals of the polysiloxane chain.

Examples of the organic groups bound to the silicon atom other than the alkenyl group include alkyl groups such as methyl, ethyl, propyl, butyl, pentyl, hexyl and heptyl; aryl groups such as phenyl, tolyl, xylyl and naphthyl; aralkyl groups such as benzyl and phenethyl; halogenated alkyl groups such as chloromethyl, 3-chloropropyl and 3,3,3-trifluoropropyl; cycloalkyl groups such as cyclopentyl and cyclohexyl and the like. In particular, it is preferably a methyl or phenyl group from the viewpoint of heat resistance.

The component (A) polysiloxane may have a hydrosilyl group.

The main chain of the component (A) is, for example, an organopolysiloxane. Concrete examples thereof include polydimethylsiloxane, methylphenylpolysiloxane and diphenylpolysiloxane. In particular, polydimethylsiloxane is preferable from the viewpoints of heat resistance and lightfastness. The lightfastness, as used in the invention, means durability against the light emitted from LED (for example, resistance to discoloration or burning).

The component (A) is not particularly limited in its molecular structure. The molecular structure may be, for example, linear, partially branched linear, cyclic, branched, three-dimensional network-shaped or the like. One of the favorable embodiments is linear.

As a preferred embodiment, the component (A) has a main chain of repeated diorganosiloxane units in its molecular structure.

When the component (A) used is a vinyl group-containing polysiloxane and/or a hydrosilyl group-containing polysiloxane, it may have an alkylene group and/or a phenylene skeleton in the structure of component (A).

The molecular terminal of the component (A) may be a silanol group (hydroxyl group bound to silicon atom) or an alkoxysilyl group, or may be blocked with a triorganosiloxy group (such as trimethylsiloxy group) or a vinyl group.

Examples of the components (A) include those represented by the following general formula (1):

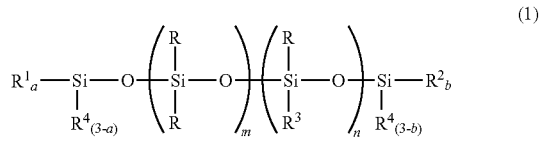

(1)

wherein $R^1$, $R^2$ and $R^3$ each independently represents an alkenyl group; groups $R^4$ each independently represents a monovalent hydrocarbon group other than alkenyl group, a hydroxy group or an alkoxy group; groups R each independently represent an organic group; a+b+n is an integer of 2 or more; a and b each independently is an integer of 0 to 3; and m and n each independently is an integer of 0 or more.

When the polysiloxane is a polysiloxane having an unsaturated hydrocarbon group as the alkenyl group, the composition containing the polysiloxane is further superior in curability.

Examples of the polysiloxane having an unsaturated hydrocarbon group as the alkenyl group include organosiloxane copolymers having a siloxane unit represented by the formula: $(R^1)_3SiO_{1/2}$, a siloxane unit represented by the formula: $(R^1)_2R^2SiO_{1/2}$, a siloxane unit represented by the formula: $(R^1)_2SiO_{2/2}$ and a siloxane unit represented by the formula: $SiO_{4/2}$; organosiloxane copolymers having a siloxane unit represented by the formula: $(R^1)_3SiO_{1/2}$, a siloxane unit represented by the formula: $(R^1)_2R^2SiO_{1/2}$ and a siloxane unit represented by the formula: $SiO_{4/2}$; organosiloxane copolymers having a siloxane unit represented by the formula: $(R^1)_2R^2SiO_{1/2}$, a siloxane unit represented by the formula: $(R^1)_2SiO_{2/2}$, and a siloxane unit represented by the formula: $SiO_{4/2}$; and organosiloxane copolymers having a siloxane unit represented by the formula: $(R^1)_2R^2SiO_{1/2}$ and a siloxane unit represented by the formula: $R^1SiO_{3/2}$; or a siloxane unit represented by the formula: $R^2SiO_{3/2}$.

When the polysiloxane contains an unsaturated hydrocarbon group as the alkenyl group, it may have an alkylene group and/or a phenylene skeleton in the polysiloxane structure.

The group $R^1$ in the formula above is a monovalent hydrocarbon group other than the alkenyl group. Examples of the monovalent hydrocarbon groups other than the alkenyl group include: alkyl groups such as methyl, ethyl, propyl, butyl, pentyl, hexyl and heptyl; aryl groups such as phenyl, tolyl, xylyl and naphthyl; aralkyl groups such as benzyl and phenethyl; halogenated alkyl groups such as chloromethyl, 3-chloropropyl and 3,3,3-trifluoropropyl and the like.

The group $R^2$ in the formula above is an unsaturated hydrocarbon group. Examples of the unsaturated hydrocarbon groups include vinyl, allyl, butenyl, pentenyl, hexenyl and heptenyl.

When the component (A) has a vinyl group as the alkenyl group, the composition is further superior in curability. The polysiloxane having a vinyl group as the alkenyl group may be referred to hereinafter as a "vinyl group-containing polysiloxane".

When the component (A) contains a (meth)acryloyl group as the alkenyl group, the composition is further superior in curability. The polysiloxane having a (meth)acryloyl group as the alkenyl group may be referred to hereinafter as a "(meth)acryloyl group-containing polysiloxane."

Examples of the (meth)acryloyl group-containing polysiloxanes include those represented by the following average composition formula (2):

$$R^1_a R^2_b SiO_{(4-a-b)/2} \qquad (2)$$

wherein $R^1$ represents a hydrogen atom, a hydroxy, an alkyl or an aryl group having 1 to 10 carbon atoms; $R^2$ represents a (meth)acryloxyalkyl group represented by $CH_2=CR^3-CO-O-(CH_2)_c-$; $R^3$ in $CH_2=CR^3-CO-O-(CH_2)_c-$ represents a hydrogen atom or a methyl group; c is an integer of 2 to 6, more preferably 2, 3 or 4; a is 0.8 to 2.4, more preferably 1 to 1.8; b is 0.1 to 1.2, more preferably 0.2 to 1, still more preferably 0.4 to 1; a+b is 2 to 2.5, more preferably 2 to 2.2.

Examples of the alkyl groups of $R^1$ in the formula above include methyl, ethyl, propyl, butyl, pentyl, hexyl, heptyl and the like. Examples of the aryl groups of $R^1$ include phenyl, tolyl, xylyl, naphthyl and the like. In particular, methyl, ethyl, propyl and phenyl groups are preferable, and a methyl group is more preferable.

The molecular weight (weight-average molecular weight) of the component (A) is preferably 500 to 100,000, more preferably 1,000 to 100,000, and still more preferably 5,000 to 50,000, from the viewpoints of curable, toughness, elongation and processability. In the present specification, the weight-average molecular weight is that converted to polystyrene, as determined by GPC (gel permeation chromatography).

The viscosity of the component (A) at 23° C. is preferably 5 to 10,000 mPa·s, and more preferably 10 to 1,000 mPa·s so that the silicone resin obtained is superior in physical properties and the silicone resin composition obtained is superior in handling efficiency. In the invention, the viscosity is determined using a type-E viscometer at a temperature of 23° C.

The components (A) may be used alone or in combination of two or more. Method for producing the component (A) is not particularly limited, and a known method may be used.

The component (B) used in practice of the invention is not particularly limited, if it is an organohydrogen polysiloxane having at least two hydrogen groups bound to silicone atoms (i.e., SiH groups) in the molecule and having a polysiloxane structure as the main chain.

The component (B) preferably has 2 to 300, and more preferably 3 to 150 hydrogen groups bound to silicon atoms in the molecule. The molecular structure of the component (B) is, for example, linear, branched, cyclic, three-dimensional network-shaped or the like.

The binding sites of the hydrogen groups bound to silicon atoms in the component (B) are, for example, one or both of the chain terminals and molecular side chains of the polysiloxane. The hydrogen groups bound to silicon atoms may bind to one terminal or both terminals of polysiloxane chain.

Examples of the component (B) include the organohydrogen polysiloxanes represented by the following average composition formula (3).

$$H_a R^3_b SiO_{(4-a-b)/2} \qquad (3)$$

wherein $R^3$ each independently represents an unsubstituted or substituted monovalent hydrocarbon group having no aliphatic unsaturated bond; a and b are each a number satisfying the conditions: $0<a<2$, $0.8 \le b \le 2$ and $0.8<a+b \le 3$, more preferably those satisfying the conditions: $0.05 \le a \le 1$, $0.9 \le b \le 2$ and $1.0 \le a+b \le 2.7$; and the number of silicon atoms in the molecule is 2 to 300, and more preferably 3 to 200.

Examples of the unsubstituted or substituted monovalent hydrocarbon group $R^3$ having no aliphatic unsaturated bond include alkyl groups such as methyl, ethyl, propyl, butyl, pentyl, hexyl and heptyl; aryl groups such as phenyl, tolyl, xylyl and naphthyl; aralkyl groups such as benzyl and phenethyl; halogenated alkyl groups such as chloromethyl, 3-chloropropyl and 3,3,3-trifluoropropyl and the like.

In particular, lower alkyl groups having 1 to 3 carbon atoms such as methyl, a phenyl group or a 3,3,3-trifluoropropyl group are preferable from the viewpoints of heat resistance and lightfastness.

Examples of the component (B) include: methyl hydrogenpolysiloxane blocked with trimethylsiloxy groups at both chain terminals, dimethylsiloxane-methyl hydrogensiloxane copolymers blocked with trimethylsiloxy groups at both chain terminals, methyl hydrogenpolysiloxane blocked with silanol groups at both chain terminals, dimethylsiloxane-methyl hydrogensiloxane copolymers blocked with silanol groups at both chain terminals, dimethylpolysiloxane blocked with dimethyl hydrogen siloxy groups at both chain terminals, methyl hydrogenpolysiloxane blocked with dimethyl hydrogen siloxy groups at both chain terminals, dimethylsiloxane-methyl hydrogensiloxane copolymers blocked with dimethyl hydrogen siloxy groups at both chain terminals and the like; silicone resins having a $(R^3)_2HSiO_{1/2}$ unit and a $SiO_{4/2}$ unit and, as needed, a $(R^3)_3SiO_{1/2}$ unit, a $(R^3)_2SiO_{2/2}$ unit, a $R^3HSiO_{2/2}$ unit, a $(H)SiO_{3/2}$ unit or a $R^3SiO_{3/2}$ unit (wherein, $R^3$ is the same as the unsubstituted or substituted monovalent hydrocarbon group having no aliphatic unsaturated bond described above) and the like; derivatives of these exemplary compounds wherein part or all of the methyl groups are replaced with other alkyl groups such as ethyl and propyl, a phenyl group or a hydrosilyl group and the like.

Examples of the component (B) include those represented by the following general formulae (4) to (7):

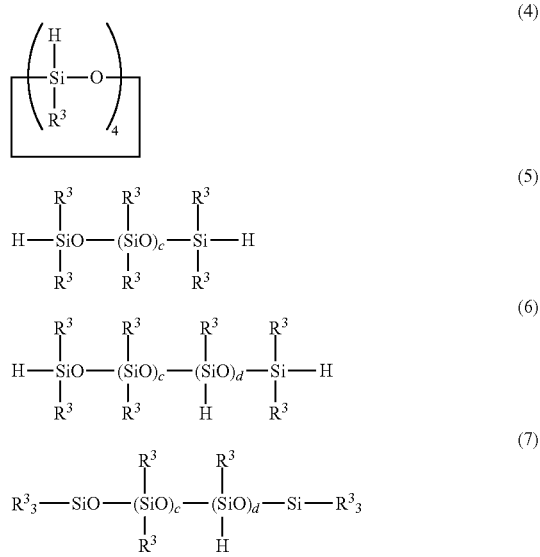

wherein $R^3$ each independently represents an unsubstituted or substituted monovalent hydrocarbon group having no aliphatic unsaturated bond; c is an integer of 0 or 1 or more; and d is an integer of 1 or more. The component (B) may be used alone or in combination of two or more.

The component (B) is prepared by a known method. Specifically, it is prepared, for example, by co-hydrolyzing at least one chlorosilane selected from those represented by the following chemical formula: $R^3SiHCl_2$ and $(R^3)_2SiHCl$ (wherein $R^3$ is the same as the unsubstituted or substituted monovalent hydrocarbon group having no aliphatic unsaturated bond described above), or co-hydrolyzing the chlorosilane above with at least one chlorosilane selected from those represented by the following chemical formula: $(R^3)_3SiCl$ and $(R^3)_2SiCl_2$ (wherein $R^3$ is the same as the unsubstituted or substituted monovalent hydrocarbon group having no aliphatic unsaturated bond described above).

A polysiloxane obtained after co-hydrolysis and equilibration may be also used as the component (B).

The component (B) is preferably used in such a way that the amount of the hydrogen atoms bound to silicon atoms (SiH groups) in the component (B) is 0.1 to 5 moles, more preferably 0.5 to 2.5 moles, and still more preferably 1.0 to 2.0 moles with respect to 1 mole of the alkenyl groups in the component (A) from the viewpoint of the properties of the resulting silicone resin or the rubber (toughness and elongation) after curing.

When the SiH group content is 0.1 moles or more, a sufficiently cured high-strength rubber (silicone resin) is obtained. When the SiH group content is 5 moles or less, a less brittle high-strength cured rubber product is obtained.

In the invention, the components (A) and (B) may be used as a mixture of the components (A) and (B).

The component (C) used in practice of the invention is a reaction catalyst for acceleration of the addition reaction between the alkenyl group in the component (A) and the hydrogen atoms bound to silicon atoms (i.e., SiH groups) in the component (B). The silicone resin composition of the invention gives a composition superior in curability as it comprises the component (C).

The component (C) is not particularly limited, and any known compounds may be used. Examples thereof include: pure platinum group metals such as platinum (including platinum black), rhodium, palladium and the like; platinum chloride, chloroplatinic acid and chloroplatinate salts such as $H_2PtCl_{4-n}H_2O$, $H_2PtCl_{6-n}H_2O$, $NaHPtCl_{6-n}H_2O$, $KHPtCl_{6-n}H_2O$, $Na_2PtCl_{6-n}H_2O$, $K_2PtCl_{4-n}H_2O$, $PtCl_{4-n}H_2O$, $PtCl_2$, and $Na_2HPtCl_{4-n}H_2O$ (wherein, n is an integer of 0 to 6, preferably 0 or 6); alcohol-modified chloroplatinic acids (see U.S. Pat. No. 3,220,972); chloroplatinic acid-olefin complexes (see U.S. Pat. Nos. 3,159,601, 3,159,662 and 3,775,452); platinum group metals such as platinum black and palladium supported on a carrier such as alumina, silica or carbon; rhodium-olefin complexes; chlorotris(triphenylphosphine)rhodium (Wilkinson catalyst); and platinum family metal-based catalysts such as the complexes of platinum chloride, chloroplatinic acid or a chloroplatinate salt with a vinyl group-containing siloxane, in particular, a vinyl group-containing cyclic siloxane.

The component (C) is used preferably in an amount of 0.1 to 500 ppm, and more preferably in an amount of 10 to 100 ppm, in terms of platinum group metal by mass, with respect to the total amount of the components (A) and (B) from the viewpoint of the curability of the composition.

The component (D) used in practice of the invention is the allylglycoluril represented by the general formula (C) above. Concrete examples thereof include:
1-allylglycoluril,
1,3-diallylglycoluril,
1,4-diallylglycoluril,
1,6-diallylglycoluril,
1,3,4-triallylglycoluril,
1,3,4,6-tetraallylglycoluril,
1-allyl-3a-methyl-glycoluril,
1,3-diallyl-3a-methyl-glycoluril,
1,4-diallyl-3a-methyl-glycoluril,
1,6-diallyl-3a-methyl-glycoluril,
1,3,4-triallyl-3a-methyl-glycoluril,
1,3,4,6-tetraallyl-3a-methyl-glycoluril,
1-allyl-3a,6a-dimethyl-glycoluril,
1,3-diallyl-3a,6a-dimethyl-glycoluril,
1,4-diallyl-3a,6a-dimethyl-glycoluril,
1,6-diallyl-3a,6a-dimethyl-glycoluril,
1,3,4-triallyl-3a,6a-dimethyl-glycoluril,
1,3,4,6-tetraallyl-3a,6a-dimethyl-glycoluril,
1-allyl-3a,6a-diphenyl-glycoluril,
1,3-diallyl-3a,6a-diphenyl-glycoluril,
1,4-diallyl-3a,6a-diphenyl-glycoluril,
1,6-diallyl-3a,6a-diphenyl-glycoluril,
1,3,4-triallyl-3a,6a-diphenyl-glycoluril,
1,3,4,6-tetraallyl-3a,6a-diphenyl-glycoluril and the like.

The silicone resin composition of the invention comprises the component (D) in an amount of 0.1 to 10 parts by mass with respect to 100 parts by mass of the total amount of the components (A) and (B). Thus, it provides a cured product with sulfur resistance, and hence, it prevents discoloration (corrosion) of silver and preserves the transparency of the cured product.

The cured product of the silicone resin composition of the invention is superior in sulfur resistance even when the cured product is not hard, so that it gives a cured product resistant to cracking. Accordingly, when the cured product is used as a sealing agent for optical semiconductor elements, the wires contained in the sealed product is prevented from breaking.

The silicone resin composition of the invention comprises the component (D) preferably in an amount of 0.1 to 10 parts by mass with respect to 100 parts by mass of the total amounts of the components (A) and (B) to suppress discoloration of the obtained cured product by heat thereby to provide the obtained cured product with superior transparency and sulfur resistance. When the content of the component (D) is less than 0.1 parts by mass with respect to 100 parts by mass of the total amounts of the components (A) and (B), the obtained cured product may not have a sufficient sulfur resistance. On the other hand, when it is more than 10 parts by mass, the obtained cure product may be discolored easily by heat and have a reduced transparency.

The components (D) may be used alone or in combination of two or more.

Further, in addition to the components above, the silicone resin composition of the invention comprises any additives in an amount in the range that does not impair the advantageous effects of the invention.

Examples of the additives include inorganic fillers, antioxidants, lubricants, ultraviolet absorbents, heat and light stabilizers, dispersants, antistatic agents, polymerization inhibitors, antifoams, curing accelerators, solvents, inorganic phosphors, aging inhibitors, radical inhibitors, adhesiveness improvers, flame retardants, surfactants, storage stability-improving agents, ozone aging inhibitors, thickeners, plasticizers, radiation ray-screening agents, nucleating agents, coupling agents, conductivity-enhancing agents, phosphorus-based peroxide decomposing agents, pigments, metal deactivators, physical property adjustors, adhesion promoters, adhesion assistants and the like and the additives for use may be known products.

Examples of the adhesion promoters or the adhesion assistants include known epoxy-based silane-coupling agents, bis(alkoxy)alkanes, isocyanurate derivatives and the like, and bis(alkoxy)alkanes and/or isocyanurate derivatives are preferable.

The bis(alkoxy)alkane is preferably, for example, at least one selected from the group consisting of 1,2-bis(triethoxysilyl)ethane, 1,6-bis(trimethoxysilyl)hexane, 1,7-bis(trimethoxysilyl)heptane, 1,8-bis(trimethoxysilyl)octane, 1,9-bis(trimethoxysilyl)nonane and 1,10-bis(trimethoxysilyl)decane. Among these is particularly preferred 1,6-bis(trimethoxysilyl)hexane.

The method for producing the silicone resin composition of the invention is not particularly limited. For instance, it is prepared by mixing the components (A), (B), (C) and (D), and additives, as needed. The silicone resin composition of the invention may be a one component or a two component composition.

When the silicone resin composition of the invention is to be a two component composition, it may be composed of a first component (liquid) containing the components (B) and (C) and a second component (liquid) containing components (A) and (D). The additives may be added to one or both of the first and second components (liquids).

The silicone resin composition of the invention has preferably a viscosity of 5 to 10,000 mPa·s, more preferably 5 to 5,000 mPa·s, at a temperature of 23° C. after 24 hours from the time when the component (B) has been mixed with a liquid containing components other than the component (B) so that the composition has an adequate pot life.

The measurement of the viscosity of the silicone resin composition of the invention mentioned above is performed using a type-E viscometer under a condition of a temperature of 23° C. and a humidity of 55%.

As applications of the silicone resin composition of the invention, there may be mentioned, for example, such an application in which it is applied on a substrate (for example, optical semiconductor element), and cured.

The method of coating and curing the silicone resin composition of the invention is not particularly limited. Examples thereof include dispense-using methods, potting, screen printing, transfer molding, injection molding and the like.

The silicone resin composition of the invention is cured by heating. The heating temperature at which the silicone resin composition of the invention is cured is normally 100° C. or higher, and it is preferably 120° C. or higher, more preferably 120° C. to 200° C., and still more preferably 120° C. to 180° C., from the viewpoint of curing efficiency.

The applications of the silicone resin composition of the invention are not particularly limited. Examples thereof include sealing agent compositions for electronic materials, sealing agent compositions for construction, sealing agent compositions for automobiles, adhesive compositions and the like.

Examples of the electronic materials include supporting materials such as lead frames, wired tape carriers, wiring boards, glass and silicon wafer; optical semiconductor elements; active elements such as semiconductor chips, transistors, diodes and thyristors; and passive elements such as capacitors, resistors and coils.

In addition, the silicone resin composition of the invention may be used, for example, in applications such as display materials, optical recording medium materials, optical device materials, optical component materials, optical fiber materials, photoelectronic functional organic materials, and semiconductor integrated circuit-related materials.

The silicone resin composition of the invention may not substantially contain a silanol group-containing silicon compound from the viewpoint of storage stability.

The silicone resin composition of the invention may be used in the presence of silver. The silicone resin composition may be cured in the presence of silver to provide a silicone resin, and in this way, discoloration (corrosion) of silver is prevented and the transparency of the silicone resin is preserved.

Hereinafter, the silicone resin will be described.

The silicone resin of the invention is prepared by curing the silicone resin composition described above. The silicone resin composition of the invention provides a silicone resin superior, for example, in sulfur resistance.

The silicone resin of the invention is produced by curing the silicone resin composition by heating.

According to the invention, it is preferred that the silicone resin composition is heated at a temperature in the range of 120° C. to 180° C. (preferably 150° C.) to cure within 20 hours (preferably 12 hours) so that it has an adequate curing period and a pot life, and it cures favorably, while the foaming of the composition and cracking of the resulting silicone resin is prevented, thereby to provide a silicone resin superior in smoothness, moldability and physical properties.

The silicone resin of the invention is used as a sealing agent for LED chips, for example. The emission color of the LED chip is not particularly limited. The color may be, for example, blue, red, yellow, green or white. The LED chips may be used alone or in combination of two or more.

Hereinafter, the sealed optical semiconductor element will be described.

The sealed optical semiconductor element according to the present invention is an optical semiconductor element wherein an LED chip is sealed with the silicone resin described above.

The silicone resin used in the sealed optical semiconductor element according to the invention is not particularly limited, if it is a silicone resin according to the present invention.

Because the sealed optical semiconductor element of the invention makes use of the silicone resin composition above, it has properties superior in sulfur resistance, rubber elasticity and flexibility.

The emission color of the LED chip used in the sealed optical semiconductor element of the invention is not particularly limited. For example, a white LED is prepared by coating a blue LED chip with the composition containing a fluorescent material such as yttrium-aluminum-garnet.

When a white emission color is to be prepared by using a red, a green and a blue LED chip, each of these three LED chips may be sealed with the silicone resin composition of the invention and these sealed products of LED chips of three colors may be used in combination. Alternatively, LED chips of three colors are integrated and sealed with the silicone resin composition of the invention to give a single light source.

The size and the shape of the LED chip are not particularly limited.

The kind of the LED chip is not particularly limited. Thus, the LED chip may be, for example, a high-power LED, a high-brightness LED, a common-brightness LED, a white LED, a blue LED or the like.

Examples of the optical semiconductor elements used in the sealed optical semiconductor element of the invention include, in addition to LEDs, organic electroluminescent elements (organic ELs), laser diodes and light emitting diode arrays.

For example, the optical semiconductor element described above may be such that it is adhered to a substrate such as a lead frame by die bonding and connected to a substrate or the like by chip bonding, wire bonding or wireless bonding.

The cured product used in the sealed optical semiconductor element of the invention seals the optical semiconductor element. Examples of the sealed optical semiconductor elements according to the invention include optical semiconductor elements directly sealed with the cured product, cannonball-type optical semiconductor elements, surface-mounted optical semiconductor elements, and sealed optical semiconductor elements wherein the space among the multiple optical semiconductor elements are sealed.

The sealed optical semiconductor element of the invention is prepared by a coating process of coating an LED chip with the silicone resin composition of the invention and a curing process of curing the silicone resin composition by heating the LED chip coated with the silicone resin composition.

The application method in the coating process is not particularly limited and, for example, a potting method, transfer molding, injection molding or screen printing.

In the curing process described above, a cured product is prepared by heating the LED chip coated with the silicone resin composition and curing the silicone resin composition. The heating temperature of the silicone resin composition then is identical with the condition described in the process of producing the silicone resin.

The method of producing the sealed optical semiconductor element according to the present invention is not particularly limited, except that the silicone resin of the invention is used as the silicone resin. Thus, for example, any known optical semiconductor element may be used. The heating temperature when the sealed optical semiconductor element of the invention is prepared is preferably the same as the heating temperature used in curing the silicone resin composition of the invention so that it cures favorably.

Examples of the applications of the sealed optical semiconductor element of the invention include, but are not limited to, automobile lamps (head lamps, tail lamps, direction lamps, etc.), home illumination apparatuses, industrial illumination apparatuses, stage illumination apparatuses, displays, signals, projectors and the like.

EXAMPLES

Hereinafter, the present invention will be described specifically with reference to Examples and Comparative Examples, but the invention is not limited thereto. Raw materials used in Examples and Comparative Examples below are as follows:

Component (A): dimethylpolysiloxane blocked with vinyl groups at both terminals ("DMS-V31" produced by Gelest, Inc., hereinafter abbreviated to (A))

Component (B): hydrogenpolysiloxane ("KF-9901" produced by Shin-Etsu Chemical Co., Ltd., hereinafter abbreviated to (B))

Component (C): platinum-cyclovinylmethylsiloxane complex ("SIP6832.2" produced by Gelest, Inc., hereinafter abbreviated to (C))

component (D): 1,3,4,6-tetraallylglycoluril ("TA-G" produced by Shikoku Chemicals Corporation, hereinafter abbreviated to (D))

The evaluation test methods used in Examples and Comparative Examples are as follows:

[Transmittance Test]

The silicone resin composition obtained was held between two glass plates (10 cm in length, 10 cm in width and 4 mm in thickness) and cured at 150° C. for 12 hours to give an initial cured product having a thickness of 2 mm. The initial cured product was additionally heated at 150° C. for 10 days as a heat resistance test to prove a cured product after the heat resistance test.

The transmittances at a wavelength of 400 nm of the initial cured product and the cured product after the heat resistance test were determined according to JIS K0115: 2004 using an ultraviolet-visible absorption spectra analyzer (manufactured by Shimadzu Corp.).

The transmission retention rate was calculated from the obtained transmittances according to the following calculation formula:

Transmittance retention rate (%)=(Transmittance of post-heat resistance test cured product)/(Transmittance of initial cured product)×100

[Heat Discoloration Resistance Test]

The silicone resin composition obtained was held between two glass plates (10 cm in length, 10 cm in width and 4 mm in thickness) and cured at 150° C. for 4 hours as a heat resistance test to give a cured product after the heat resistance test.

The initial cured product and the cured product after heat resistance test were examined by visual observation to determine whether the cured product after the heat resistance test showed yellowing as compared to the initial cured product.

[Sulfur Resistance Test]

The silicone resin composition obtained was applied on a silver-plated substrate to a thickness of about 1 mm and cured at 150° C. for 3 hours, to give a test sample.

Subsequently, pulverized iron sulfide powder (10 g, in large excess to hydrochloric acid (0.5 mmol)) was placed on the bottom of a 10-L desiccator; a perforated plate (with through-holes) was placed above the iron sulfide so that the perforated plate is not in contact with the iron sulfide powder in the desiccator; and a test sample was placed on the perforated plate. Then, hydrochloric acid (0.5 mmol) was added dropwise to the iron sulfide powder to generate hydrogen sulfide (0.25 mmol) (theoretical value of concentration: 560 ppm). (Reaction formula: $FeS+2HCl \rightarrow FeCl_2+H_2S$)

Discoloration of the silver of the test sample after 24 hours from the start of generation of hydrogen sulfide was examined by visual observation and evaluated according to the following evaluation criteria:

○: no discoloration observed x: discoloration observed

[Adhesiveness Test]

The silicone resin composition obtained was poured into a package for LED and cured by heating it at 150° C. for 3 hours to give a test sample.

The cured product, i.e., the test sample obtained, was then rubbed with a spatula and the adhesiveness thereof was evaluated according to the following evaluation criteria:

○: cured product not easily exfoliated x: cured product easily exfoliated

Examples 1 to 3 and Comparative Example 1

Respective raw materials were mixed uniformly at the blending rate shown in Table 10 in a vacuum mixer, to give a silicone resin composition.

The silicone resin composition obtained was subjected to the transmittance test, heat discoloration resistance test, sulfur resistance test and adhesiveness test and the test results obtained are summarized in Table 10.

TABLE 10

|  | Examples | | | Comparative |
| --- | --- | --- | --- | --- |
|  | 1 | 2 | 3 | Example 1 |
| Composition (parts by mass) | | | | |
| (A) | 90 | 90 | 90 | 90 |
| (B) | 10 | 10 | 10 | 10 |
| (C) | 0.05 | 0.05 | 0.05 | 0.05 |
| (D) | 1 | 5 | 10 |  |
| Results of evaluation Transmittance test (%) | | | | |
| Initial cured product | 89 | 89 | 89 | 88 |
| Cured product after heat resistance test | 87 | 87 | 87 | 80 |
| Transmittance retention rate | 98 | 98 | 98 | 91 |
| Heat discoloration test | no yellowing | no yellowing | no yellowing | yellowing |
| Sulfur resistance test | ○ | ○ | ○ | X |
| Adhesiveness test | ○ | ○ | ○ | X |

The results of the test shown in Table 10 show that the silicone resin composition of the invention provides a cured product superior not only in sulfur resistance and transparency, but also in adhesiveness.

The invention claimed is:

1. An epoxy resin composition comprising an epoxy resin and a tetraglycidylglycoluril represented by formula (B),

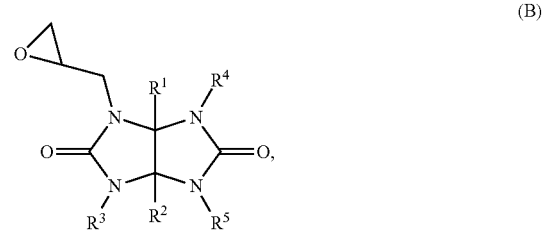

(B)

wherein $R^1$ and $R^2$ each independently represents a hydrogen atom, a lower alkyl or a phenyl group; and $R^3$, $R^4$ and $R^5$ each represents a glycidyl group, as a cross-linking agent.

2. An epoxy resin composition comprising an epoxy resin, wherein at least one component of the epoxy resin is a tetraglycidylglycoluril represented by formula (B),

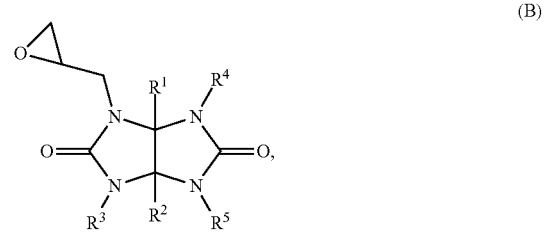

(B)

wherein $R^1$ and $R^2$ each independently represents a hydrogen atom, a lower alkyl or a phenyl group; and $R^3$, $R^4$ and $R^5$ each represents a glycidyl group.

3. The epoxy resin composition according to claim 2, further comprising at least one component selected from the group consisting of a glass filler, a curing agent that is an acid anhydride liquid at room temperature, a curing accelerator, a curing catalyst that is a cationic catalyst generating cationic species by UV radiation, a curing catalyst that is a catalyst generating cationic species by a heat treatment, a polyester resin, an organosiloxane and a rubber particle.

4. A curable composition comprising:
(A) an alkenyl group-containing organic compound;
(B) a compound having at least three hydrosilyl groups in the molecule; and
(C) a hydrosilylation catalyst,
wherein the component (A) comprises a tetraallylglycoluril represented by formula (C1):

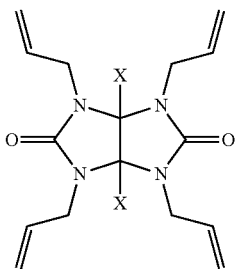
(C1)

wherein X represents a hydrogen atom, a lower alkyl or an aryl group.

5. The curable composition according to claim 4 wherein the component (B) is:
(B-3) an organic-modified silicone compound obtained by hydrosilylation reaction of (B-1) an organic compound having at least two alkenyl groups with (B-2) a linear and/or cyclic organohydrogen siloxane having at least two hydrosilyl groups in the molecule.

6. The curable composition according to claim 5 wherein the component (B-1) is at least one compound selected from the group consisting of polybutadiene, vinylcyclohexane, cyclopentadiene, divinylbiphenyl, bisphenol A diacrylate, trivinylcyclohexane, triallyl isocyanurate, methyl diallyl isocyanurate and a glycoluril represented by formula (C2):

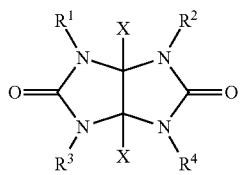
(C2)

wherein $R^1$, $R^2$, $R^3$ and $R^4$ each represents an organic group; at least two of them are alkenyl groups; and X represents a hydrogen atom, a lower alkyl or an aryl group.

7. The curable composition according to claim 5, wherein the component (B-1) is a glycoluril represented by formula (C2),

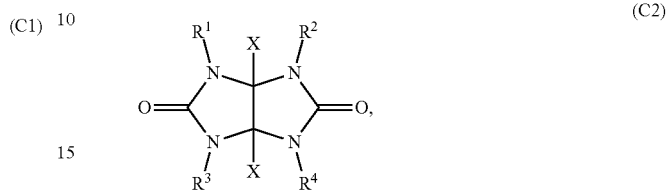
(C2)

wherein $R^1$, $R^2$, $R^3$ and $R^4$ each represents an organic group; at least two of them are alkenyl groups; and X represents a hydrogen atom, a lower alkyl or an aryl group.

8. The curable composition according to claim 5, wherein the component (B-1) is a tetraallylglycoluril represented by formula (C1),

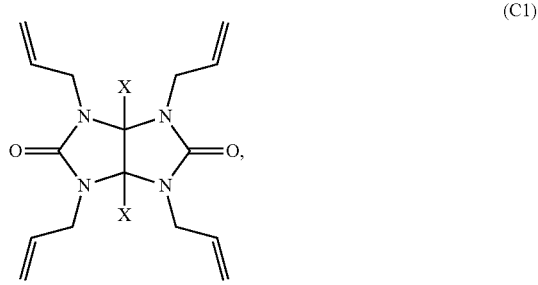
(C1)

wherein X represents a hydrogen atom, a lower alkyl or an aryl group.

9. A cured product obtained by curing the curable composition according to claim 4.

10. A thermosetting resin composition comprising:
(A) an organopolysiloxane polymer represented by formula (C3):

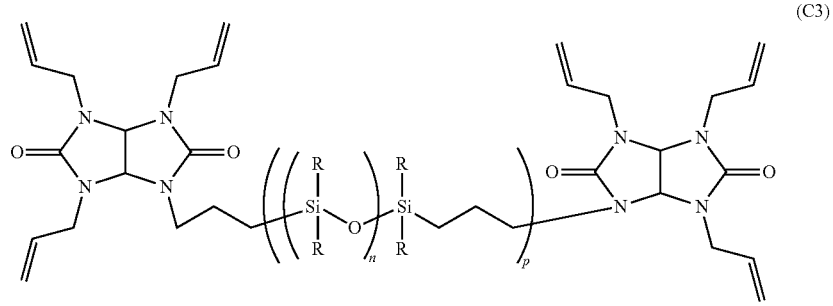
(C3)

wherein each R independently represents an alkyl or a phenyl group: n is an integer of 1 to 50;
and p is an integer of 1 to 30, as an alkenyl group-containing organopolysiloxane;
(B) a glycoluril ring-containing organohydrogen polysiloxane polymer represented by formula (C4):

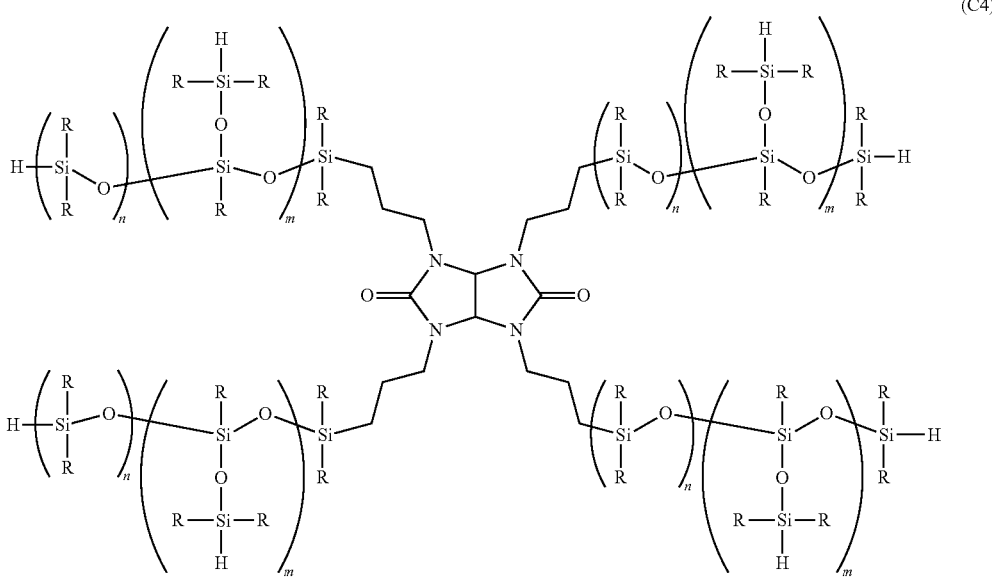

wherein each R independently represents an alkyl or a phenyl group; n is an integer of 1 to 50; m is an integer of 0 to 5; and respective siloxane recurring units in the formula above may be bound to each other at random, as an organohydrogen polysiloxane; and
(C) a curing accelerator.

11. The thermosetting resin composition according to claim 10, further comprising (D) an inorganic filler.

12. The thermosetting resin composition according to claim 10, wherein the amount of the Si—H groups in the component (B) is 0.8 to 4.0 mole per 1 mole of the allyl groups in the component (A).

13. An electron beam-curable resin composition comprising a polyolefin resin and a crosslinking agent,
wherein the crosslinking agent is an allylglycoluril group represented by formula (C):

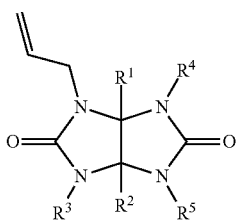

wherein $R^1$ and $R^2$ each independently represents a hydrogen atom, a lower alkyl or a phenyl group; and $R^3$, $R^4$ and $R^5$ each independently represents a hydrogen atom or an allyl group.

14. A silicone resin composition comprising:
component (A): a polysiloxane having at least two silicon-bound alkenyl groups,
component (B): a polysiloxane crosslinking agent having at least two silicon-bound hydrogen groups,
component (C): a hydrosilylation reaction catalyst, and
component (D): an allylglycoluril represented by formula (C):

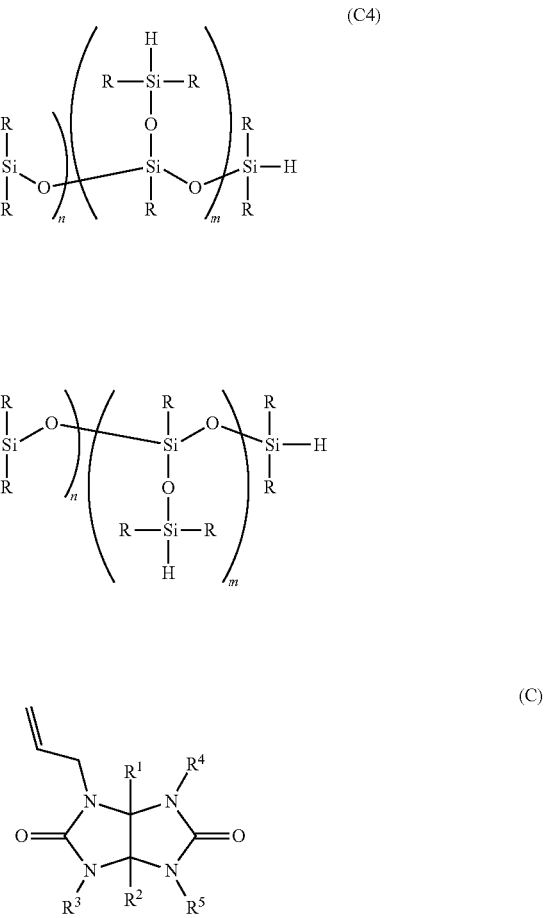

wherein $R^1$ and $R^2$ each independently represents a hydrogen atom, a lower alkyl or a phenyl group; and $R^3$, $R^4$ and $R^5$ each independently represents a hydrogen atom or an allyl group, and wherein the component (D) is contained in an amount of 0.1 to 10 parts by mass with respect to 100 parts by mass of the total amount of the components (A) and (B).

15. The silicone resin composition according to claim 14, comprising substantially no silicon compound containing a silanol group.

16. The silicone resin composition according to claim 14, wherein the alkenyl group is a vinyl or (meth)acryloyl group.

17. The silicone resin composition according to claim 14, for use in sealing of optical semiconductor elements.

* * * * *